United States Patent
Mousa et al.

(10) Patent No.: US 11,186,551 B2
(45) Date of Patent: *Nov. 30, 2021

(54) COMPOSITION OF SCALABLE THYROINTEGRIN ANTAGONISTS WITH IMPROVED RETENTION IN TUMORS

(71) Applicant: NanoPharmaceuticals, LLC, Rensselaer, NY (US)

(72) Inventors: Shaker A. Mousa, Wynantskill, NY (US); Bruce A. Hay, Niskayuna, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/173,561

(22) Filed: Feb. 11, 2021

(65) Prior Publication Data

US 2021/0340111 A1    Nov. 4, 2021

Related U.S. Application Data

(63) Continuation of application No. 16/862,076, filed on Apr. 29, 2020, now Pat. No. 10,961,204.

(51) Int. Cl.
*C07D 249/04* (2006.01)
*A61P 35/00* (2006.01)

(52) U.S. Cl.
CPC ............ *C07D 249/04* (2013.01); *A61P 35/00* (2018.01)

(58) Field of Classification Search
CPC .................................................... C07D 249/04
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,208,483 A | 6/1980 | Lee |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,596,712 B2 | 7/2003 | Zasloff et al. |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Renato |
| 6,936,274 B2 | 8/2005 | Hanshew, Jr. |

(Continued)

FOREIGN PATENT DOCUMENTS

| | | |
|---|---|---|
| CA | 2673133 | 11/2008 |
| CN | 1126589 | 7/1996 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
J. M. Keith, et al. Bioorg. Med. Chem. Lett. 26 (2016) 3109-3114.*
Faden et al., "Endogenous Opioid Immunoreactivity in Rat Spinal Cord Following Traumatic Injury", Ann. Neurol., 17 (4):386-390 (1985) 5 pages. (NPL101).
Faden, A.I., "Experimental Neurobiology of Central Nervous System Trauma", Crit. Rev. Neurobiol., 7(3-4): 175-186 (1993) 13 pages. (NPL102).
Feeney et al., "Amphetamine, Haloperidol, and Experience Interact to Affect Rate of Recovery After Motor Cortex Injury", Science, 217(4562):855-857 (1982) 4 pages. (NPL103).

(Continued)

*Primary Examiner* — Shawquia Jackson
(74) *Attorney, Agent, or Firm* — Schmeiser, Olsen & Watts, LLP

(57) ABSTRACT

Chemical compounds/compositions, methods of synthesis, and methods of use. The compounds/compositions are directed toward thyrointegrin antagonists conjugated to a polymer. The compounds/compositions further comprise an additional substituent also conjugated to the polymer. The compounds/compositions demonstrate increased uptake across the blood brain barrier along with increased retention therein and retention within tumor. The compounds/compositions may also include improved synthesis scalability, improved purity, improved aqueous solubility, and a solid product or intermediate. The compounds/compositions may demonstrate improved antiangiogenic effect and improved efficacy against conditions, particularly cancers, requiring blood brain barrier permeability, for example, glioblastoma (GBM).

12 Claims, 33 Drawing Sheets

(16 of 33 Drawing Sheet(s) Filed in Color)

(56) References Cited

U.S. PATENT DOCUMENTS

| | | |
|---|---|---|
| 7,166,155 B2 | 1/2007 | Takeshi |
| 7,358,085 B2 | 4/2008 | Zhang et al. |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Davis et al. |
| 8,802,240 B2 | 8/2014 | Davis et al. |
| 9,180,107 B2 | 11/2015 | Mousa et al. |
| 9,198,887 B2 | 12/2015 | Mousa et al. |
| 9,220,788 B2 | 12/2015 | Davis et al. |
| 9,272,049 B2 | 3/2016 | Alexander-Bridges et al. |
| 9,289,395 B2 | 3/2016 | Davis et al. |
| 9,498,536 B2 | 11/2016 | Mousa et al. |
| 9,539,345 B2 | 1/2017 | Kim et al. |
| 9,579,300 B2 | 2/2017 | Mousa et al. |
| 9,750,709 B2 | 9/2017 | Mousa et al. |
| 9,839,614 B2 | 12/2017 | Mousa et al. |
| 10,130,686 B2 | 11/2018 | Mousa et al. |
| 10,201,616 B2 | 2/2019 | Mousa et al. |
| 10,328,043 B1 | 6/2019 | Mousa et al. |
| 2001/0021763 A1 | 9/2001 | Harris |
| 2001/0023254 A1 | 9/2001 | McElroy |
| 2001/0046521 A1 | 11/2001 | Zasloff et al. |
| 2002/0049247 A1 | 4/2002 | Chen |
| 2002/0132205 A1 | 9/2002 | Faour |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0104999 A1 | 6/2003 | Iozzo |
| 2003/0138557 A1 | 7/2003 | Allison |
| 2003/0143727 A1 | 7/2003 | Chang |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |
| 2004/0033259 A1 | 2/2004 | Hanshew, Jr. et al. |
| 2004/0208844 A1 | 10/2004 | Ignatious |
| 2004/0219668 A1 | 11/2004 | Frei et al. |
| 2005/0124862 A1 | 6/2005 | Mousa et al. |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0266393 A1 | 12/2005 | Baxter et al. |
| 2005/0272817 A1 | 12/2005 | Heino |
| 2006/0166303 A1 | 7/2006 | Spanuth |
| 2006/0210539 A1 | 9/2006 | Zhang |
| 2006/0216251 A1 | 9/2006 | Morariu |
| 2007/0117841 A1 | 5/2007 | Ozes et al. |
| 2007/0190160 A1 | 8/2007 | Turos et al. |
| 2008/0081074 A1 | 4/2008 | Gu et al. |
| 2008/0124280 A1 | 5/2008 | Mousa et al. |
| 2008/0193377 A1 | 8/2008 | Line et al. |
| 2008/0199850 A1 | 8/2008 | Sutter et al. |
| 2009/0022806 A1 | 1/2009 | Mousa et al. |
| 2009/0175862 A1 | 7/2009 | Silverio et al. |
| 2009/0197240 A1 | 8/2009 | Fishman et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0112079 A1 | 5/2011 | Thomas et al. |
| 2011/0142941 A1 | 6/2011 | Davis et al. |
| 2012/0258069 A1 | 10/2012 | Alexander-Bridges et al. |
| 2012/0315320 A1 | 12/2012 | Davis et al. |
| 2013/0224115 A1 | 8/2013 | Wang et al. |
| 2014/0044646 A1 | 2/2014 | Li et al. |
| 2014/0072635 A1 | 3/2014 | Mousa et al. |
| 2014/0072646 A1 | 3/2014 | Mousa et al. |
| 2014/0170066 A1 | 6/2014 | Rajopadhye et al. |
| 2014/0199375 A1 | 7/2014 | Mousa et al. |
| 2014/0294931 A1 | 10/2014 | Mousa et al. |
| 2015/0139934 A1 | 5/2015 | Mousa et al. |
| 2015/0238631 A1 | 8/2015 | Kim et al. |
| 2016/0178615 A1 | 6/2016 | Alexander-Bridges et al. |
| 2016/0348052 A1 | 12/2016 | Lin et al. |
| 2017/0080058 A1 | 3/2017 | Mousa et al. |
| 2017/0348425 A1 | 12/2017 | Mousa et al. |
| 2017/0348428 A1 | 12/2017 | Mousa et al. |
| 2019/0111145 A1 | 4/2019 | Mousa et al. |
| 2019/0314314 A1 | 10/2019 | Mousa et al. |

FOREIGN PATENT DOCUMENTS

| | | |
|---|---|---|
| CN | 104530417 A | 4/2015 |
| EP | 2954933 A1 | 12/2015 |
| JP | 04356184 A | 12/1992 |
| JP | 2010513526 A | 4/2010 |
| KR | 100830889 B1 | 5/2008 |
| WO | 9500135 | 1/1995 |
| WO | 9640048 | 12/1996 |
| WO | 9833942 | 8/1998 |
| WO | 9856771 | 12/1998 |
| WO | 9951638 | 10/1999 |
| WO | 9958119 A1 | 11/1999 |
| WO | 9959548 A1 | 11/1999 |
| WO | 9962549 | 12/1999 |
| WO | 0064431 A1 | 11/2000 |
| WO | 0078815 A1 | 12/2000 |
| WO | 0113031 A2 | 2/2001 |
| WO | 0113936 A1 | 3/2001 |
| WO | 0176589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031922 A2 | 3/2006 |
| WO | 200735612 A2 | 3/2007 |
| WO | 2008051291 A2 | 5/2008 |
| WO | 2008140507 A2 | 11/2008 |
| WO | 2010075332 A1 | 7/2010 |
| WO | 2010120506 A1 | 10/2010 |
| WO | 2010148007 A2 | 12/2010 |
| WO | 2012009425 A2 | 1/2012 |
| WO | 2015074050 A1 | 5/2015 |
| WO | 2016004043 | 1/2016 |
| WO | 2017214299 | 12/2017 |

OTHER PUBLICATIONS

Fei et al., "P53 and radiation responses", Oncogene, 22:5774-5783 (2003) 10 pages (NPL104).

Felding-Habermann et al., "Integrin activation controls metastasis in human breast cancer", Proc. Natl. Acad. Sci. U.S.A, 98(4):1853-1858 (2001) 6 pages. (NPL105).

Feng et al., "Fibrin and Collagen Differentially Regulate Human Dermal Microfascular Endothelial Cell Integrins: Stablization of $\alpha v/\beta 3$ mRNA by Fibrin", J. Invest. Dermatol., 113(6):913-919 (1999) 7 pages. (NPL106).

Fife et al., "Effects of tetracyclines on angiogenesis in vitro", Cancer Letters, 153:75-78 (2000) 4 pages. (NPL107).

Folkman, J., "Angiogenesis in cancer, vascular, rheumatoid and other disease", Nat. Med., 1(1):27-31 (1995) 5 pages. (NPL108).

Freese et al., "Characterization and mechanism of glutamate neurotoxicity in primary striatal cultures", Brain Res., 521 (1-2):254-264 (1990) 12 pages. (NPL109).

Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages. (NPL110).

Fujii et al., "Crystal Structure of Trimestatin, a Disintegrin Containing a Cell Adhesion Recognition Motif RGD", J. Mol. Biol., 332:1115-1122 (2003) 8 pages. (NPL111).

(56) References Cited

OTHER PUBLICATIONS

Gavrieli et al., "Identification of Programmed Cell Death In Situ via Specific Labeling of Nuclear DNA Fragmentation", J. Cell. Biol., 119(3):493-501 (1992) 9 pages. (NPL112).
GenBank Accession No. AF083106, Apr. 14, 2000 5 pages. (NPL113).
GenBank Accession No. AF083107, Mar. 21, 2001. 3 pages. (NPL114).
GenBank Accession No. NM_002210, Jun. 15, 2008 8 pages. (NPL115).
GenBank Accession No. NM_012238, Apr. 25, 2010. 8 pages. (NPL116).
GenBank Accession No. NM_030593, Mar. 14, 2010. 8 pages. (NPL117).
GenBank Accession No. NP_036370, Apr. 25, 2010. 6 pages. (NPL118).
GenBank Accession No. NP_501912, Nov. 13, 2008. 4 pages. (NPL119).
GenBank Accession No. P53685, Apr. 20, 2010. 8 pages. (NPL120).
Geng et al., "A Specific Antagonist of the p110δ Catalytic Component of Phosphatidylinositol 3'-Kinase, IC486068, Enhances Radiation-Induced Tumor Vascular Destruction", Cancer Res., 64:4893-4899 (2004) 7 pages. (NPL121).
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages. (NPL122).
Gladson, C.L., "Expression of integrin αv-β3 in Small Blood Vessels of Glioblastoma Tumors", J. Neuropath. Exp. Neurol., 55(11): 1143-1149(1996) 7 pages. (NPL123).
Glinskii et al., "Modification of survival pathway gene expression in human breast cancer cells by tetraiodothyroacetic acid (tetrac)", Cell Cycle, 8(21):3562-3570 (2009) 9 pages. (NPL124).
Glinsky et al., "Classification of Human Breast Cancer Using Gene Expression Profiling as a Component of the Survival Predictor Algorithm", Clin. Cancer Res., 10:2272-2283 (2004) 12 pages. (NPL125).
Glinsky et al., "Gene expression profiling predicts clinical outcome of prostate cancer", J. Clin. Invest., 113(6):913-923 (2004) 11 pages. (NPL126).
Glinsky et al., "Microarray analysis identifies a death-from-cancer signature predicting therapy failure in patients with multiple types of cancer", J. Clin. Invest., 115(6):1503-1521 (2005) 19 pages. (NPL127).
Glinsky et al., "Microarray Analysis of Xenograft-Derived Cancer Cell Lines Representing Multiple Experimental Models of Human Prostate Cancer", Mol. Carcinog., 37:209-221 (2003) 13 pages. (NPL128).
Goldstein et al., "Influence of Lesion Size and Location on Amphetamine-Facilitated Recovery of Beam-Walking in Rats", Behav. Neurosci., 104(2):320-327 (1990) 9 pages. (NPL129).
Goldstein, A., "Estimating the Error Variance and the Confidence Interval for a Regression Line", in Biostatistics, The MacMillan Co., New York, pp. 139-146 (1964) 10 pages. (NPL130).
Goodman, M.M., "Automated Synthesis of Radiotracers for PET Applications", in Clinical Positron Emission Tomography, Mosby Yearbook, K.F. Hubner et al., Chapter 14, pp. 110-122(1992) 13 pages. (NPL131).
Grant, D.B., "Monitoring TSH concentrations during treatment for congenital hypothyroidism", Arch. Disease Childhood, 66:669-670 (1991) 2 pages. (NPL132).
Gregoriadis, "Liposomes", in Drug Carriers in Biology and Medicine, Chapter 14, pp. 287-341, Academic Press (1979) 57 pages. (NPL133).
Guigon et al., "Regulation of β-Catenin by a Novel Nongenomic Action of Thyroid Hormone β Receptor", Mol. Cell. Biol., 28(14);4598-4608 (2008) 11 pages. (NPL134).
Hahn et al., "Plateau-phase cultures of mammalian cells: An in vitro model for human cancer", Curr. Top. Radiat. Res. Q., 8:39-83 (1972) 45 pages. (NPL135).
Halks-Miller et al., "CCR1 Immunoreactivity in Alzheimer's Disease Brains", Society for Neuroscience Meeting, Abstract #787.6, vol. 24 (1998) Abstract Only. 1 page. (NPL136).
Hansebout, R.R., "A Comprehensive Review of Methods of Improving Cord Recovery After Acute Spinal Cord Injury", in Early Management of Acute Spinal Cord Injury, pp. 181-196 (1982) 16 pages. (NPL137).
Hartert, H., "Blutgerinnungsstud Mit Der Thrombelastogeraphie, Einem Neuen Untersuchungsverfahren", Klinische Wochenschrift 26(37/38):577-583 (1948) German Language Only. 9 pages. (NPL138).
Hashimoto et al., "Matrix Metalloproteinases Cleave Connective Tissue Growth Factor Reactivate Angiogenic Activity of Vascular Endothelial Growth Factor 165", J. Biol. Chern. 277(39):36288-36295 (2002) 8 pages. (NPL139).
Heller et al., "Inhibition of potentially lethal damage recovery by altered pH, glucose utilization and proliferation in plateau growth phase human glioma cells", Int. J. Radiat. Biol., 66(1):41-47 (1994) 7 pages. (NPL140).
Hercbergs et al., "GL261 brain tumor cells: responses to single or fractionated x-irradiation with the αvβ3 integrin thyroxine receptor antagonist tetrac (tetraiodothyroacetic acid)", 20th EORTC-NCI-AACR Symposium on Molecular Targets and Cancer Therapeutics, Geneva, Switzerland, Oct. 2008 (NPL141).
Hercbergs et al., "GL261 brain tumor cells: responses to single or fractionated x-irradiation with the αvβ3 integrin thyroxine receptor antagonist tetrac (tetraiodothyroacetic acid)", Euro. J. Cancer, 6(12):172 (Abstract Only) 4 pages (NPL142).
Hercbergs et al., "Propylthiouracil-induced Chemical Hypothyroidism with High-Dose Tamoxifen Prolongs Survival in Recurrent High Grade Glioma: A Phase I/II Study", Anticancer Res., 23:617-626 (2003) 10 pages. (NPL143).
Hercbergs, A., "The Thyroid Gland as an Intrinsic Biologic Response-Modifier in Advanced Neoplasia—A Novel Paradigm", in vivo, 10:245-247 (1996) 3 pages. (NPL144).
Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages. (NPL145).
Hercbergs, et al., "Radiosensitization of GL261 glioma cells by tetraiodothyroacetic acid (tetrac)", Cell Cycle, 8(16):2586-2591 (2009) 6 pages. (NPL146).
Hermanson, "Modification with Synthetic Polymers", in Bioconjugate Tech., Ch. 15, Academic Press, San Diego, CA, pp. 617-618 (1996) 4 pages. (NPL147).
Hoff et al., "Medullary Thyroid Carcinoma", Hematol. Oncol. Cin. North Am., 21(3):475-488 (2007) 14 pages. (NPL148).
Horuk et al., "Expression of Chemokine Receptors by Subsets of Neurons in the Central Nervous System", J. Immunol., 158:2882-2890 (1997) 9 pages. (NPL149).
Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages. (NPL150).
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages. (NPL301).
Utsumi et al., "Potentially Lethal Damage Versus Sublethal Damage: Independent Repair Processes in Actively Growing Chinese Hamster Cells", Radial. Res., 77:346-360 (1979) 9 pages. (NPL302).
Van Waes et al., "Effects of the novel αv integrin antagonist SM256 and cis-platinum on growth of murine squamous cell carcinoma PAM LY8", Int. J. Oncol., 16(6):1189-1195 (2000) 8 pages. (NPL303).
VanCutsem et al., "Cetuximab and Chemotherapy as Initial Treatment for Metastatic Colorectal Cancer", N. Engl. J. Med., 360:1408-1417 (2009) 10 pages. (NPL304).
Varnes et al., "The Effect of pH on Potentially Lethal Damage Recovery in A549 Cells", Radiat. Res., 108:80-90 (1986) 11 pages. (NPL305).
Velasco et al., "Dermatological Aspects of Angiogenesis." Brit. J. Dermatol. 147(2002):841-852 12 pages. (NPL306).
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages. (NPL307) (50199PCT IPRP Mar. 16, 2006).

(56) References Cited

OTHER PUBLICATIONS

Wang et al., "Integrin-associated Protein Stimulates α2β1-dependent Chemotaxis via Gi-mediated inhibition of Adenylate Cyclase and Extracellular-regulated Kinases", J. Cell. Biol., 147:389-399 (1999) 11 pages. (NPL308).

Wen et al., "Prognostic Value of EGFR and TGF-α in Early Laryngeal Cancer Treated With Radiotherapy", Laryngoscope, 106(7):884-888 (1996) 6 pages. (NPL309).

Werdelin et al., "Neuropeptides and neural cell adhesion molecule (NCAM) in CSF from patients with ALS", Acta Neurol. Scand., 79(3):177-181 (1989) (NPL310).

Wilkinson, J.H., "Synthesis of some Possible Metabolites of Thyroxine and Triiodothyronine", Biochem. J., 63:601-605 (1956) 5 pages. (NPL311).

Xia et al., "Chemokines/chemokine receptors in the central nervous system and Alzheimer's disease", J. NeuroVirol., 5:32-41 (1999) 11 pages. (NPL312).

Yalcin et al., "Tetraidodothyroacetic Acid (Tetrac) and Tetrac Nanoparticles Inhibit Growth of Human Renal Cell Carcinoma Xenografts", Anticancer Res., 29:3825-3832 (2009) 7 pages. (NPL313).

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages. (NPL314).

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages. (NPL315).

Yanase et al., "Role of N-methyl-D-aspartate receptor in acute spinal cord injury", J. Neurosurg., 83:884-888 (1995) 6 pages. (NPL316).

Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages. (NPL317).

Yang, et al., "Enhanced inhibition of adipogenesis and induction of apoptosis in 3T3-L1 adipocytes with combinations of resveratrol and quercetin", Life Sci., 82:1032-1039 (2008) 8 pages. (NPL318).

Yonkers et al., "Sensory Neuron Sodium Current Requires Nongenomic Actions of Thyroid Hormone During Development", J. Neurophysiol., 100:2719-2725 (2008) 7 pages. (NPL319).

Young, W., "Role of Calcium in Central Nervous System Injuries", J. Neurotrauma, 9(Suppl. 1): S9-S25(1992) 18 pages. (NPL320).

Young, W., "Secondary injury mechanisms in acute spinal cord injury", J. Emerg. Med., 11:13-22 (1993) 11 pages. (NPL321).

Yu et al., "Osteopontin Gene is Expressed in the Dermal Papilla of Pelage Follicles in a Hair-Cycle-Dependent Manner", J. Invest. Dermatol., 117:1554-1558 (2001) 5 pages. (NPL322).

Yu, et al., "The Corepressor Silencing Mediator for Retinoid and Thyroid Hormone Receptor Facilitates Cellular Recovery from DNA Double-Strand Breaks", Cancer Res., 66(18):9316-9322 (2006) 7 pages. (NPL323).

Zhang et al., "Oestrogen inhibits resveratrol-induced post-translational modification of p53 and apoptosis in breast cancer cells", Br. J. Cancer, 91:178-185 (2004) 8 pages. (NPL324).

Zhang et al., "Quantitative PET Imaging of Tumor Integrin αvβ3 Expression with 18F-FRGD2", J. Nucl. Med., 47:113-121 (2006) 9 pages. (NPL325).

Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages. (NPL326).

Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages. (NPL327).

Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages. (NPL328).

NCI Cancer Drug Information, Cetuximab, 2006,http://www.cancer.gov/cancertopics/druginfo/cetuximab,downloaded Jul. 18, 2014. (NPL329).

Gu et al. 2007, Nanotoday 2:14-21. (NPL330).

Wood, J. et al. "Novel Antiangiogenic Effects of the u Bisphosphonate Compound Zoledronic Acid." The Journal of Pharmacology and Experimental Therapeutics, vol. 302, No. 3, 2002, pp. 1055-1061. (NPL331).

Park, T.G., "Bioconjugation of Biodegradable Poly (lactic'glycolic acid) to Protein, Peptide, and Anti-Cancer Drug: An Alternative Pathway for Achieving Controlled Release from Micro- and Nanoparticles." in Polymeric Drugs and Drug Delivery Systems, Ottenbrite R.M. and Kim S.W., eds., Ch. 7, pp. 101-114 (2001) (NPL332).

Oh, Jong Eun, et al., "Conjugation of drug to poly (D,L-lacitic-co-glycoli acid) for controlled release from biodegradable microspheres." Journal of Controlled Release 57, 269-280 (1999). (NPL333).

Ditsch, Nina, et al., "Thyroid Function in Breast Cancer Patients." Anticancer Research 30:1713-1718 (2010). (NPL334).

Webmd.com (http://www.webmd.com/women/news/20030410/underactive-thyroid-lowers-breast-cancer). Dated Apr. 10, 2003. (NPL335).

Mousa, Shaker A., et al., "Tetraiodothyroacetic acid and its nanoformulation inhibit thyroid hormone stimulation of non-small cell lung cancer cells in vitro and its growth in xenografts." Lung Cancer 76; 39-45 (2012). (NPL336).

Leuthy,A.; et al. "autologous stem cell transplantation: leukapheresis product has anti-angiogenic effects in vivo correlating with neutrophil-derived 'VEGFR1" Anticancer Research, 2001, v.31, 9.3115-3124. (NPL337).

Mythyroid.com. "Blood tests" (Http://222.mythyroid.com/bloodtests.html) cached 2005 wayback machine. (NPL338).

Huang, Kuo-Shiang, et al. "Combination of Baculovirus-Mediated Gene Delivery and Packed-Bed Reactor for Scalable Production of Adeno-Associated Virus", Human Gene Therapy, Mary Ann Liebert, Inc., Publishers, US., vol. 18, No. 11. 2007, pp. 1161-1170 (NPL339).

Lin, Hung-Yun, et al. "Pharmacodynamic Modeling of Anti-Cancer Activity of Tetraiodotheyroacetic Acid In a Perfused Cell Culture System" Plos Computational Biology, vol. 7, N.2, 2011, p.e1001073 (NPL340).

Veronese, "Peptide and protein PEGylation: a review of problems and solutions" Biomaterials 22 (2001) 405-417 (NPL341).

Oshaghi, Ebrahim Abbasi, et al., "Role of resveratrol in the management of insulin resistance and related conditions Mechanism of action," Critical Reviews in Clinical Laboratory Sciences, 2017. vol. 54, No. 4, pp. 27-293 (NPL342).

Mayo Clinic, "Multiple sclerosis—Diagnosis and treatment," URL: https://www.mayoclinic.org/diseases-conditions/multiple-sclerosis/diagnosis-treatment/drc-20350274 accessed Dec. 21, 217, 12 printed pages. (Year: 2017) (NPL343).

Susman, E., "Beware of Non-Aspirin NSAIDs for Kidney Cancer Patients." Genitourinary Cancers Symposium, oncology-times.com, 2016, p. 21. (Year: 2016) (NPL344).

European Examination Report for EP Application No. 07867073.4, dated Jul. 16, 2015. (50199CIP2EP). (NPL345).

Application No. PCT/US04/030583, International Preliminary Report on Patentability dated Mar. 16, 2006, 9 pates. (50199PCT) (NPL346).

Lane, N.E., et al., "Osteoarthritis year in review 2016: clinical," Osteoarthritis and Cartilage, vol. 25, 2017, pp. 209-215 (Year: 2017). (NPL347).

*Kennecott Corporation*, Plaintiff-Appellant v. *Kyocera International, Inc.*, and *Kyoto Ceramic Co., Ltd.*, Defendant-Appellee. Case Decided Dec. 22, 1987. (https://law.resource.org/pub/us/case/reporterF2/835/835.F2d.1419.871151.html), accessed Jan. 15, 2016, 5 printed pages. (NPL348).

Application No. PCT/US11/043837, International Preliminary Report on Patentability dated Jan. 15, 2013. 5 pages. (50996PCT) (NPL349).

Tetraiodothyroacetic Acid-Tagged Liposomes for Enhanced Delivery of Anticancer Drug to Tumor Tissue Via Integrin Receptor http://www.sciencedirect.com/sciencearticle/pii/S0168365912004567 (51647SEAR) (NPL350).

Office Action (dated Mar. 30, 2020) for U.S. Appl. No. 15/056,522, filed Feb. 29, 2016.

(56) References Cited

OTHER PUBLICATIONS

Restriction Requirement (dated Jul. 30, 2020) for U.S. Appl. No. 16/398,342, filed Apr. 30, 2019.
Li, Biomacromolecules 2003, 4, 1055-1067. (Year: 2003).
Ulbrich, Chem. Rev. 2016, 116, 5338-5431, published Apr. 25, 2016. (Year: 2016).
"Bertolla, Monofunctionalizations of beta-cyclodextrin, conjugation with recognition patterns, and biological evaluation, Thesis, 2010.(Year: 2010)".
Japanese Office Action (dated Mar. 23, 2021) for Patent Application No. JP20190513717—Filing Date May 20, 2016.
Notice of Allowance (dated Mar. 31, 2021) for U.S. Appl. No. 16/398,342, filed Apr. 30, 2019.
Final Office Action (dated Dec. 30, 2020) for U.S. Appl. No. 15/056,522, filed Feb. 29, 2016.
Office Action (dated Oct. 31, 2019) for U.S. Appl. No. 16/223,176, filed Dec. 18, 2018.
JP Office Action (dated Mar. 23, 2021) for Patent Application No. JP20190513717—Filing Date May 20, 2016.
Office Action (dated Nov. 30, 2020) for U.S. Appl. No. 16/398,342, filed Apr. 30, 2019.
U.S. Appl. No. 16/862,076, filed Apr. 29, 2020; GAU 1626; Confirmation No. 3113; Customer No. 05409.
Notice of Allowance (dated Nov. 13, 2020) for U.S. Appl. No. 16/862,076, filed Apr. 29, 2020.
Pujol et al., "Letter to the editors: Prevention of thyroid neoplasm recurrence with Triac and levothyroxine", Clin. Endocrinol., 46(1):121-122 (1997) 2 pages. (NPL251).
Raue et al., "Multiple Endocrine Neoplasia Type 2", Horm. Res., 68(Suppl.5): 101-104 (2007) 4 pages. (NPL252).
Rayalam et al., "Resvelalrol induces apoptosis and inhibits adipogenesis in 3T3-L1 adipocytes", Phytother. Res., 22:1367-1371 (2008) 5 pages. (NPL253).
Rebbaa et al., "Novel function of the thyroid hormone analog tetraiodothyroacetic acid: a cancer chemosensitizing and anticancer agent", Angiogenesis, 11(3):269-276 (2008) 8 pages. (NPL254).
Reinholt et al., "Osteopontin—a possible anchor of osteoclasts to bone", Proc. Natl. Acad. Sci. U.S.A., 87:4473-4475 (1990) 3 pages. (NPL255).
Remsen et al., "Antibodies to the Neural Cell Adhesion Molecule Disrupt Functional Recovery in Injured Nerves", Exp. Neurol., 110:268-273 (1990) 6 pages. (NPL256).
Ren et al., "Regulation of tumor angiogenesis by thrombospondin-1", Biochim. Biophys. Acta. 1765:178-188 (2006) 11 pages. (NPL257).
Risau, W., "Mechanisims of angiogenesis", Nature, 386:671-674 (1997) 4 pages. (NPL258).
Sahni et al., "Stimulation of endothelial cell proliferation by FGF-2 in the presence of fibrinogen requires $\alpha v \beta 3$". Blood, 104(12):3635-3641 (2004) 7 pages. (NPL259).
Saito et al., "Vector-mediated delivery of 125I-labeled β-amyloid peptide Aβ1-40 through the blood-brain barrier and binding to Alzheimer disease of the Aβ1 -40/vector complex". Proc. Natl. Acad. Sci. US, 92:10227-10231 (1995) 5 pages. (NPL260).
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages. (NPL261).
SAS/STAT Guide for Personal Computers, Version 6 Edition, p. 717 (1987) 3 pages. (NPL262).
Sato et al., "Neovascularization: General Remarks", Biotherapy, 15(6):631-636 (2001) (English Abstract) 6 pages. (NPL263).
Scanlan et al., "3-Iodothyronamine is an endogenous and rapid-acting derivative of thyroid hormone", Nat. Med., 10(6):638-642 (2004) 5 pages. (NPL264).
Scanlan et al., "Selective thyromimetics: Tissue-selective thyroid hormone analogs", Curr. Opin. Drug Discov. Dev., 4(5):614-622 (2001) 9 pages. (NPL265).
Schlange et al., "Autocrine WNT signaling contributes to breast cancer cell proliferation via the canonical WNT pathway and EGFR transactivation", Breast Cancer Res., 9:R63 (2007) 15 pages. (NPL266).

Schlumberger et al., "New therapeutic approaches to treat medullary thyroid carcinoma", Nat. Clin. Prac. Endocrinol. Metab., 4(10):22-32 (2008) 11 pages. (NPL267).
Schnell et al., "Expression of alpha v beta 3 integrin in patients with high and low grade glioma", Proc. Amer. Assoc. Cancer Res., 47:226 (2006) Abstract Only. 5 pages. (NPL268).
Schnell et al., "Expression of Integrin $\alpha v \beta 3$ in Gliomas Correlates with Tumor Grade and Is not Restricted to Tumor Vasculature", Brain Pathol., 18:378-386 (2008) 9 pages. (NPL269).
Schreiber et al., "Hormone delivery systems to the brain-transthyretin", Exp. Clin. Endocrinol. Diabetes, 103(2): 75-80 (1995) 7 pages. (NPL270).
Schueneman et al., "SU11248 Maintenance Therapy Prevents Tumor Regrowth after Fractionated Irradiation of Murine Tumor Models", Cancer Res., 63:4009-4016 (2003) 8 pages. (NPL271).
Shih et al., "Thyroid Hormone Promotes Serine Phosphorylation of p53 by Mitogen-Activated Protein Kinase", Biochem., 40:2870-2878 (2001) 10 pages. (NPL272).
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4):1708-1717 (2004) 10 pages. (NPL273).
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages. (NPL274).
Shinohara et al., "Enhanced radiation damage of tumor vasculature by mTOR inhibitors", Oncogene, 24:5414-5422 (2005) 9 pages. (NPL275).
Skrovronsky et al., "In vivo detection of amyloid plaques in a mouse model of Alzheimer's disease", Proc. Natl. Acad. Sci US, 97(13):7609-7614 (2000) 6 pages. (NPL276).
Skuli et al., "$\alpha \sqrt{}\beta 3/\alpha \sqrt{}\beta 5$ integrins-FAK-RhoB: A Novel Pathway for Hypoxia Regulation in Glioblastoma", Cancer Res., 69(8):3308-3316 (2009) 9 pages. (NPL277).
Song et al., "Formulation and characterization of biodegradable nanoparticles for intravascular local drug delivery", J. Controlled Rel., 43:197-212 (1997) 16 pages. (NPL278).
Stefani et al., "The Effect of Resveralrol on a Cell Model of Human Aging", Ann. NY Acad. Sci., 1114:407-418 (2007) 12 pages. (NPL279).
Strieth, et al., "Antiangiogenic combination tumor therapy blocking αv-integrins and VEGF-receptor-2 increases therapeutic effects in vivo", Int. J. Cancer, 119:423-431 (2006) 9 pages. (NPL280).
Sumi et al., "Wound healing using regenerative medicine", Surg. Front., 10(2):162-165 (2003) 4 pages. (NPL281).
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages. (NPL282).
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231. (NPL283).
Szatmari et al., "Detailed characterization of the mouse glioma 261 tumor model for experimental glioblastoma therapy", Cancer Sci., 97(6):546-553 (2006) 8 pages. (NPL284).
Szumiel, I., "Ca2+, Mg2+ and (Adenosine Diphosphate Ribose)n in Cellular Response to Irradiation", J. Theor. Biol., 101:441-451 (1983) 11 pages. (NPL285).
Takemaru et al., "Chibby, a nuclear β-catenin-associated antagonist of the Wnt/Wingless pathway", Nature, 422:905-909 (2003) 5 pages. (NPL286).
Tanaka et al., J. Soc. Gastroenterological Surgery, 27(2):360 (1996) 3 pages. (NPL287).
Tang et al., "Resvelalrol-induced Cyclooxygenase-2 facilitates p53-dependent apoptosis in human breast cancer cells", Mol. Cancer Ther., 5(8):2034-2042 (2006) 9 pages. (NPL288).
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages. (NPL289).

(56) References Cited

OTHER PUBLICATIONS

Tator et al., "Review of the secondary injury theory of acute spinal cord trauma with emphasis on vascular mechanisms", J. Neurosurg., 75(1):15-26 (1991) 13 pages. (NPL290).

Theodossiou et al., "Propylthiouracil-induced Hypothyroidism Reduces Xenograft Tumor Growth in Athymic Nude Mice", Cancer, 86:1596-1601 (1999) 6 pages. (NPL291).

Thompson et al., "The Clinical Manipulation of Angiogenesis: Pathology, Side-Effects, Surprises, and Opportunites with Novel Human Therapies." J. Pathol. 190(2000):330-337 8 pages. (NPL292).

Thraves et al., "Radiosensitization of Human Fibroblasts by 3-Aminobenzamide: An Inhibitor of Poly(ADP-Ribosylation)", Radiat Res., 104:119-127 (1985) 9 pages. (NPL293).

Tol et al., "Chemotherapy, Bevacizumab, and Cetuximab in Metastatic Colorectal Cancer", N. Engl. J. Med., 360(6):563-572 (2009) 10 pages. (NPL294).

Tomanek et al., "A Thyroid Hormone Analog Stimulates Angiogenesis in the Post-infarcted Rat Heart", J. Mol. Cell Cardiol., 30(5):923-932 (1998) 10 pages. (NPL295) (50199PCT IPRP Mar. 16, 2006).

Tomanek et al., "Angiogenesis: New Insights and Therapeutic Potential", Anatomical Record (New Anat.), 261:126-135 (2000) 10 pages. (NPL296).

Tomanek et al., "Early Coronary Angiogenesis in Response to Thyroxine: Growth Characteristics and Upregulation of Basic Fibroblast Growth Factor", Circ. Res., 82(5):587-593 (1998) 8 pages. (NPL297) (50199PCT IPRP Mar. 16, 2006).

Tomanek et al., "Growth of the Coronary Vasculature in Hypertrophy: Mechanisms and Model Dependence", Cell. Mol. Bio. Res., 40(2):129-136 (1994) 8 pages. (NPL298) (50199PCT IPRP Mar. 16, 2006).

Toms et al., "Thyroid Hormone Depletion Inhibits Astrocytoma Proliferation via a p53-Independent Induction of p21 (WAF/1CIP1)", Anticancer Res., 18:289-293 (1998) 5 pages. (NPL299).

Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages. (NPL300).

Mandelin et al., "Extracellular and Intracellular Mechanisms That Mediate the Metastatic Activity of Exogenous Osteopontin", Cancer, 115:1753-1764 (2009) 12 pages. (NPL201).

Mangale et al., "Identification of genes regulated by an interaction between $\alpha v \beta 3$ integrin and vitronectin in murine decidua", Reprod. Fertil. Dev., 20:311-319 (2008) 10 pages. (NPL202).

Markgraf et al., "Sensorimotor and cognitive consequences of middle cerebral artery occlusion in rats", Brain Res., 575 (2):238-246 (1992) 10 pages. (NPL203).

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages. (NPL204).

Masson-Gadais et al., "Integrin $\alpha v \beta 3$ requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages. (NPL205).

McCarty et al., "Promises and Pitfalls of Anti-Angiogenic Therapy in Clinical Trials." Trends Mol. Med. 9.2(2003):53-58 6 pages. (NPL206).

Meneses et al., "Recombinant angiostatin prevents retinal neovascularization in a murine proliferative retinopathy model", Gene Therapy, 8(8):646-648 (2011) 3 pages. (NPL207).

Mezosi et al., "Nongenomic effect of thyroid hormone on free-radical production in human polymorphonuclear eukocytes", J. Endocrinol., 185:121-129 (2005) 9 pages. (NPL208).

Mishkin et al., "Increased Survival of Rats Bearing Morris Hepatoma 7800 after Induction of Hypothyroidism", Cancer Res., 39:2371-2375 (1979) 5 pages. (NPL209).

Miyaguchi et al., "Correlation of Epidermal Growth Factor Receptor and Radiosensitivity in Human Maxillary Carcinoma Cell Lines", ActaOtolaryngol., 118:428-431 (1998) 4 pages. (NPL210).

Moeller et al., "Cytosolic Action of Thyroid Hormone Leads to Induction of Hypoxia-inducible Factor-$1\alpha$ and Glycolytic Genes", Molec. Endo., 19(12):2955-2963 (2005) 9 pages. (NPL211).

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4:E020 (2006) 4 pages. (NPL212).

Mohamed et al., "Wound healing properties of cimetidine in vitro", Drug Intell. Clin. Pharm., 20(12):973-975 (1986) 4 pages. (NPL213).

Monferran et al., "$\alpha v \beta 3$ and $\alpha v \beta 5$ integrins control glioma cell response to ionising radiation through ILK and RhoB", Int. J. Cancer, 123:357-364 (2008) 8 pages. (NPL214).

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages. (NPL215).

Moreno et al., "Metabolic Effects of Thyroid Hormone Derivatives", Thyroid, 18(2):239-253 (2008) 15 pages. (NPL216).

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18(2):239-253 (2008) 15 pages. (NPL217).

Mousa et al., "Cellular and Molecular Mechanisms of Nicotine's Pro-Angiogenesis Activity and Its Potential Impact on Cancer", J. Cell. Biochem., 97:1370-1378 (2006) 9 pages. (NPL218).

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages. (NPL219).

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages. (NPL220).

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages. (NPL221).

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages. (NPL222).

Mousa et al., "The Proangiogenic Action of Thyroid Hormone Analogue GC-1 Is Initiated at an Integrin", J. Cardiovasc. Pharmacol., 46(3):356-360 (2005) 6 pages. (NPL223).

Mousa, et al., "Pro-angiogenesis action of thyroid hormone and analogs in a three-dimensional in vitro microvascular endothelial sprouting model", Int. Angiol., 25(4):407-413 (2006) (NPL224).

Mousa, S.A., "Mechanisms of Angiogenesis: Potential Therapeutic Targets", in Angiogenesis Inhibitors and Stimulators: Potential Therapeutic Implications, Landes Bioscience, Georgetown, Texas, Chapter I, pp. 1-12 (2000) 14 pages. (NPL225).

Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages. (NPL226).

Muller et al., "The Double Life of the Ku Protein: Facing the DNA Breaks and the Extracellular Environment", Cell Cycle, 4(3);438-441 (2005) 4 pages. (NPL227).

Ndiaye et al., "Red wine polyphenol-induced, endothelium-dependent NO-mediated relaxation is due to the redoxsensitive PI3-kinase / Akt-dependent phosphorylation of endothelial NO-synthase in the isolated porcine coronary artery", FASEB J., 19(3);455-457 (2005) 3 pages. (NPL228).

Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages. (NPL229).

(56) References Cited

OTHER PUBLICATIONS

Nehls et al., "A Novel Micorcarrier-Based in Vitro Assay for Rapid and Reliable Quantification of Three-Dimensional Cell Migration and Angiogenesis", Microvasc. Res., 50(3):311-322 (1995) 12 pages. (NPL230).

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages. (NPL231).

Newcomb et al., "Radiation Sensitivity of GL261 Murine Glioma Model and Enhanced Radiation Response by Flavopiridol", Cell Cycle., 5(1):93-99 (2006) 7 pages. (NPL232).

Nickoloff et al., "Aberrant Production of Interieukin-8 and Thrombospondin-1 by Psoriatic Keratinocytes Mediates Angiogenesis." Am. J. Pathol. 144.4(1994):820-828 9 pages. (NPL233).

Nilsson et al., "Evidence for Multiple Thyroxine-binding Sites in Human Prealbumin", J. Biol. Chem., 246(19) 5098-6105 (1971) 8 pages. (NPL234).

Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages. (NPL235).

Oak et al., "Antiangiogenic properties of natural polyphenols from red wine and green tea", J. Nutr. Biochem., 16:1-8 (2005) 8 pages. (NPL236).

Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages (NPL237).

Pages et al., "Signaling Angiogenesis via p42/p44 MAP Kinase Cascade", Ann. N.Y. Acad., Sci., 902:187-200 (2000) 14 pages. (NPL238).

Painter et al., "Membrane initiation of DNA synthesis", Nature, 270:543 (1977) 1 page. (NPL239).

Panter et al., "Pretrealment with NMDA antagonists limits release of excitatory amino acids following traumatic brain injury", Neurosci. Lett., 136(2): 165-168 (1992) 4 pages. (NPL240).

Panyam, et al., "Biodegradable nanoparticles for drug and gene delivery to cells and tissues", Advanced Drug Delivery Reviews, 55: 329-347 (2009) 19 pages. (NPL241).

Pardridge, W.M., "Receptor-Mediated Peptide Transport through the Blood-Brain Barrier", Endocrine Rev., 7 (3):314-330 (1986) 18 pages. (NPL242).

Park et al., "Effects of Tetramethoxystilbene on Hormone-Resistant Breast Cancer Cells: Biological and Biochemical Mechanisms of Action", Cancer Res., 67:5717-5726 (2007) 10 pages. (NPL243).

Parveen, et al., "Polymeric nanoparticles for cancer therapy", Journal of Drug Targeting, 16(2): 108-123, Feb. 2008. 16 pages. (NPL244).

Patel, D.K., "Clinical Use of Anti-Epidermal Growth Factor Receptor Monoclonal Antibodies in Metastatic Colorectal Cancer", Pharmacotherapy, 28(11 Pt.2):31S-41S (2008) 12 pages. (NPL245).

Penno et al., "Rapid and quantitative in vitro measurement of cellular chemotaxis and invasion", Meth. Cell Sci., 19:189-195 (1997) 7 pages. (NPL246).

Pirola, et al., "Resvelalrol: One Molecule, Many Targets", IUBMB Life, vol. 60, Issue 5, pp. 323-332. 10 pages. (NPL247).

Plow et al., "Ligand Binding to Integrins", J. Biol. Chem., 275(29):21785-21788 (2000) 4 pages. (NPL248).

Powell, J., "The Serial Analysis of Gene Expression", in Meth. Mol. Biol., Chapter 20, 99:297-319 (2000) 23 pages. (NPL249).

Prichard et al., "Concurrent Cetuximab and Bevacizumab Therapy in a Murine Orthotopic Model of Anaplastic Thyroid Carcinoma", Laryngoscope, 117:674-679 (2007) 7 pages. (NPL250).

64Cu-Labeled Tetraiodothyroacetic Acid-Conjugated Liposomes for PET Imaging of Tumor Angiogenesis http://www.sciencedirect.con/science/article/pii/S969805113001704 (51647SEAR) (NPL351).

European Patent Application No. 10 790 068.0, Office Action dated Jul. 11, 2018. 4 pages (50198EP) (NPL352).

Estrada-Ortiz, Natalia, et al. "Artificial Macrocycles as Potent p53-MDM2 Inhibitors," ACS Med. Chem. Lett. 2017, 8, 1025-1030, 6 pages. (NPL353).

Surmiak, Ewa, et al. "Rational design and synthesis of 1,5-disubstituted tetrazoles as potent inhibitors of the MDM2-p53 interaction," European Journal of Medicinal Chemistry, 126, (2017) 384-407, 24 pages. (NPL354).

Suryakiran, N., et al. "Facile N-tert-butoxycarbonylation of amines using $La(NO3)3 \cdot 6H2O$ as a mild and efficient catalyst under solvent-free conditions," Tetrahedron Letters, 47 (2006), 8039-8042; 4 pages. (NPL355).

Lin, H., et al. "L-Thyroxine vs. 3,5,3'-triiodo-L-thyronine and cell proliferation: activation of mitogen-activated protein kinase and phosphatidylinositol 3-kinase," Am. J. Physiol Cell Physiol 296 (2009): C980-C991; 12 pages. (NPL356).

Office Action (dated Jul. 21, 2010) for U.S. Appl. No. 12/004,979, filed Dec. 21, 2007.

Office Action (dated Jun. 21, 2011) for U.S. Appl. No. 12/947,389, filed Nov. 16, 2010.

Office Action (dated Apr. 4, 2012) for U.S. Appl. No. 12/947,389, filed Nov. 16, 2010.

Office Action (dated Oct. 17, 2012) for U.S. Appl. No. 12/947,389, filed Nov. 16, 2010.

Office Action (dated Mar. 12, 2014) for U.S. Appl. No. 12/947,389, filed Nov. 16, 2010.

Office Action (dated Sep. 4, 2014) for U.S. Appl. No. 12/947,389, filed Nov. 16, 2010.

Notice of Allowance (dated Nov. 16, 2015) for U.S. Appl. No. 12/947,389, filed Nov. 16, 2010.

Office Action (dated May 23, 2012) for U.S. Appl. No. 12/816,287, filed Jun. 15, 2010.

Office Action (dated Apr. 11, 2013) for U.S. Appl. No. 12/816,287, filed Jun. 15, 2010.

Office Action (dated Oct. 24, 2013) for U.S. Appl. No. 12/816,287, filed Jun. 15, 2010.

Office Action (dated May 8, 2014) for U.S. Appl. No. 12/816,287, filed Jun. 15, 2010.

Notice of Allowance (dated May 12, 2015) for U.S. Appl. No. 12/816,287.

Restriction Requirement (dated May 5, 2016) for U.S. Appl. No. 14/977,776.

Office Action (dated Nov. 4, 2016) for U.S. Appl. No. 14/977,776.

Restriction Requirment (dated Sep. 14, 2012) for U.S. Appl. No. 12/626,068, filed Nov. 25, 2009.

Office Action (dated Jan. 4, 2013) for U.S. Appl. No. 12/626,068, filed Nov. 25, 2009.

Notice of Allowance (dated Apr. 29, 2013) for U.S. Appl. No. 12/626,068, filed Nov. 25, 2009.

Office Action (dated Mar. 16, 2011) for U.S. Appl. No. 11/663,047, filed Oct. 9, 2007.

Notice of Allowance (dated Aug. 22, 2011) for U.S. Appl. No. 11/663,047, filed Oct. 9, 2007.

Office Action (dated Apr. 8, 2013) for U.S. Appl. No. 11/786,723, filed Apr. 11, 2007.

Office Action (dated Oct. 5, 2012) for U.S. Appl. No. 12/644,493, filed Dec. 22, 2009.

Office Action (dated Oct. 16, 2014) for U.S. Appl. No. 12/644,493, filed Dec. 22, 2009.

Office Action (dated Oct. 12, 2016) for U.S. Appl. No. 12/644,493, filed Dec. 22, 2009.

Office Action (dated Apr. 24, 2017) for U.S. Appl. No. 12/644,493, filed Dec. 22, 2009.

Restriction Requirement (dated Oct. 8, 2010) for U.S. Appl. No. 11/992,152, filed Nov. 3, 2009.

Office Action (dated Dec. 10, 2010) for U.S. Appl. No. 11/992,152, filed Nov. 3, 2009.

Office Action (dated Apr. 2, 2013) for U.S. Appl. No. 13/156,047, filed Jun. 8, 2011.

Office Action (dated Feb. 25, 2014) for U.S. Appl. No. 13/156,047, filed Jun. 8, 2011.

Office Action (dated Apr. 16, 2015) for U.S. Appl. No. 13/156,047, filed Jun. 8, 2011.

(56) References Cited

OTHER PUBLICATIONS

Notice of Allowance (dated Nov. 2, 2015) for U.S. Appl. No. 13/156,047, filed Jun. 8, 2011.
Restriction Requirement (dated Feb. 7, 2013) for U.S. Appl. No. 13/345,194, filed Jan. 6, 2012.
Offce Action (dated Apr. 29, 2013) for U.S. Appl. No. 13/345,194, filed Jan. 6, 2012.
Office Action (dated Oct. 15, 2013) for U.S. Appl. No. 13/345,194, filed Jan. 6, 2012.
Notice of Allowance (dated Feb. 6, 2014) for U.S. Appl. No. 13/345,194, filed Jan. 6, 2012.
Restriction Requirement (dated Mar. 13, 2012) for U.S. Appl. No. 12/751,375, filed Mar. 31, 2010.
Office Action (dated Jul. 13, 2012) for U.S. Appl. No. 12/751,375, filed Mar. 31, 2010.
Office Action (dated Apr. 12, 2013) for U.S. Appl. No. 12/751,375, filed Mar. 31, 2010.
Office Action (dated Jan. 12, 2015) for U.S. Appl. No. 12/751,375, filed Mar. 31, 2010.
Office Action (dated Jun. 3, 2015) for U.S. Appl. No. 12/751,375, filed Mar. 31, 2010.
Notice of Allowance (dated Jul. 7, 2015) for U.S. Appl. No. 12/751,375, filed Mar. 31, 2010.
Restriction Requirement (dated May 18, 2007) for U.S. Appl. No. 10/943,072, filed Sep. 14, 2004.
Office Action (dated Jul. 9, 2007) for U.S. Appl. No. 10/943,072, filed Sep. 14, 2004.
Office Action (dated Dec. 21, 2007) for U.S. Appl. No. 10/943,072, filed Sep. 14, 2004.
Hudlicka et al., "Factors involved in capillary growth in the heart", Mol. Cell. Biochem, 147:57-68 (1995) 12 pages. (NPL151).
Igarashi et al., "Techniques Supporting Angiogenesis Therapy 2: DDS Technique Supporting Regenerative Medicine." Inflamm. Immun. 10.6(2002):652-658 7 pages. (NPL152).
Illario et al., "Fibronectin-Induced Proliferation in Thyroid Cells is Mediated by $\alpha v \beta 3$ Integrin through Ras/Raf-1/MEK/ERK and Calcium/CaMKII Signals", J. Clin. Endocrinol. Metab., 90(5):2865-2873 (2005) 9 pages. (NPL153).
Ingerman-Wojenski et al., "Evaluation of electrical aggregometry: comparison with optical aggregometry, secretion of ATP, and accumulation of radiolabeled platelets", J. Lab. Clin. Med., 101(1):44-52 (1983) 10 pages. (NPL154).
Iwata et al., "A new, convenient method for the preparation of 4-[18F]fluorobenzyl halides", Applied Radiation and Isotopes, 52(1):87-92 (2000) 7 pages. (NPL155).
Jain, K.K., "Strategies and technologies for drug delivery systems", TIPS, 19:155-157 (1998) 5 pages. (NPL156).
Janssen et al., "Pathogenesis of Spinal Cord Injury and Newer Treatments—A Review", Spine, 14(1):23-32 (1989) 11 pages. (NPL157).
Jeffrey et al., "The preparation and characterisation of poly(lactide-co-glycolide) microparticles. 1. Oil-in-water emulsior solvent evaporation", Int. J. Pharm., 77:169-175 (1991) 7 pages. (NPL158).
Jonker et al., "Cetuximab for the Treatment of Colorectal Cancer", N. Engl. J. Med., 357(20):2040-2048 (2007) 9 pages. (NPL159).
Jordan et al., "Thyroid Status is a Key Modulator of Tumor Oxygenation: Implication for Radiation Therapy", Radiat. Res., 168:428-432 (2007) 5 pages. (NPL160).
Kalofonos et al., "Monoclonal Antibodies in the Management of Solid Tumors", Curr. Top. Med. Chem., 6:1687-1705 (2006) 19 pages. (NPL161).
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages. (NPL162).
Kastan et al., "A Mammalian Cell Cycle Checkpoint Pathway Utliziing P53 and GADD45 is Defective in Ataxia-Telangiectasia", Cell. 71:587-597 (1992) 11 pages. (NPL163).

Kawasuji et al., Jap. Circ. J., 63(Suppl. 1 ):65 (1999) Japanese Abstract Only. 3 pages. (NPL164).
Kerr et al., "Novel Small Molecule $\alpha v$ Integrin Antagonists: Comparative Anti-Cancer Efficacy with Known Angiogenesis Inhibitors", Anticancer Res., 19:959-968 (1999) (NPL165).
Kerr et al., "Small molecule $\alpha \sqrt{}$ integrin antagonists: novel anti-cancer agents", Exp. Opin. Invest. Drugs, 9 (6):1271-1279 (2000) 9 pages. (NPL166).
Kim et al., "Regulation of Angiogenesis in Vivo, by Ligation of Integrin $\alpha 5\beta 1$ with the Central Cell-Binding Domain of Fibronectin", Am. J. Pathol., 156(4): 1345-1362 (2000) 18 pages. (NPL167).
Kim et al., "Soluble Flt-1 gene delivery using PEI-g-PEG-RGD conjugate for anti-angiogenesis", J. Control Release, 106:224-234 (2005) 11 pages. (NPL168).
Kimelberg, H.K., "Astrocytic Edema in CNS Trauma", J. Neurotrauma, 9(Suppl. 1):S71-S81 (1992) 12 pages. (NPL169).
Kitevska et al., "Caspase-2: collroversial killer or checkpoint controller?", Apoptosis, 14:829-848(2009) 20 pages. (NPL170).
Kleczkowska et al., "Differential poly(ADP-ribose) metabolism in repair-proficient and repair-deficient murine lymphoma cells", Mut. Res., 235:93-99 (1990) 7 pages. (NPL171).
Klunk et al., "Development of Small Molecule Probes for the Beta-Amyloid Protein of Alzheimer's Disease", Neurobiol. Aging, 15(6):691-698 (1994) 8 pages. (NPL172).
Kobayashi et al., "Drug Delivery Catheter." Surg. Front. 9.1(2002):55-57 3 pages. (NPL173).
Konno et al., "Antiogenetic therapy for carcinoma", Igaku No Ayumi, 194(10): 824-828 (2000) 5 pages. (NPL174).
Koutras et al., "Antiproliferative effect of exemestane in lung cancer cells", Mol. Cancer, 8(1):109 (2009) 12 pages. (NPL175).
Koyama et al., "Recent Status and Future Perspectives in Therapeutic Angiogenesis", Prog. Med., 22(12):3070-3076 (2002) (English Abstract) 7 pages. (NPL176).
Kramer et al., "Human Microvascular Endothelial Cells Use $\beta 1$ and $\beta 3$ Integrin Receptor Complexes to Attach to Laminin", J. Cell Biol., 111:1233-1343 (1990) 11 pages. (NPL177).
Kumar et al., "Enhancing Effect of Thyroxine on Tumor Growth and Metastases in Syngeneic Mouse Tumor Systems", Cancer Res., 39:3515-3518 (1979) 4 pages. (NPL178).
Kuroki et al., "Diabetic retinopathy—The mechanisms of the ocular neovascularization of the development of anti-angiogenic drugs-", Nippon Rinsho, 57(3):584-589 (1999) (English Absliact Only) 6 pages. (NPL179).
Kwok et al., "Differences in EGF rated radiosensitisation of human squamous carcinoma cells with high and low numbers of EGF receptors", Br. J. Cancer, 64:251-254 (1991) 4 pages. (NPL180).
Lameloise et al., "Differences between the effects of thyroxine and tetraiodothyroacetic acid on TSH suppression and cardiac hypertrophy", Eur. J. Endocrinol., 144:145-154 (2001) 10 pages. (NPL181).
Lawler et al., "Cell Attachment to Thrombospondin: The Role of ARG-GLY-ASP, Calcium and Integrin Receptors", J. Cell Biol., 107(6 Pt. 1): 2351-2361 (1988) 11 pages (NPL182).
Letterio et al., "Maternal Rescue of Transforming Growth Factor-$\beta 1$ Null Mice", Science, 264:1936-1938 (1994) 4 pages. (NPL183).
Li et al., "Requirement of hypoxia-inducible factor-$1\alpha$ down-regulation in mediating the antitumor activity of the anti-epidermal growth factor receptor monoclonal antibody cetuximab", Mol. Cancer Ther., 7(5):1207-1217 (2008) 11 pages. (NPL184).
Lin et al., "Androgen-induced human breast cancer cell proliferation is mediated by discrete mechanisms in estrogen receptor-$\alpha$-positive and -negative breast cancer cells", J. Steroid Biochem. Mol. Biol., 113:182-188 (2009) 7 pages. (NPL185).
Lin et al., "Identification of the Putative MAP Kinase Docking Site in the Thyroid Hormone Receptor-$\beta 1$ DNA-Binding Domain: Functional Consequences of Mutations at the Docking Site", Biochem., 42:7571-7579 (2003) 9 pages. (NPL186).
Lin et al., "Integrin $\alpha v \beta 3$ contains a receptor site for resvelaliol", FASEB J., 20(10): 1742-1744 (2006) 3 pages. (NPL187).
Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages. (NPL188).

(56) References Cited

OTHER PUBLICATIONS

Lin et al., "Resveratrol Causes COX-2- and p53-Dependent Apoptosis in Head and Neck Squamous Cell Cancer Cells", J. Cell Biochem., 104:2131-2142 (2008) 12 pages. (NPL189).
Lin et al., "Resveratrol Induced Serine Phosphorylation of p53 Causes Apoptosis in a Mutant p53 Prostate Cancer Cell Line", J. Urol., 168:748-755 (2002) 8 pages. (NPL190).
Lin et al., "Resveratrol is pro-apoptotic and thyroid hormone is anti-apoptotic in glioma cells: both actions are integrin and ERK mediated", Carcinogenesis, 29(1):62-69 (2008) 8 pages (NPL191).
Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages. (NPL192).
Lin et al., "Thyroid hormone is a MAPK-dependent growth factor for thyroid cancer cells and is anti-apoptotic", Steroids, 72:180-187 (2007) 8 pages. (NPL193).
Liu et al., "Calcineurin Is a Common Target of Cyclophilin-Cyclosporin A and FKBP-FK506 Complexes", Cell, 66:807-815 (1991) 9 pages. (NPL194).
Lorger et al., "Activation of tumor cell integrin $\alpha v \beta 3$ controls angiogenesis and metastatic growth in the brain", Proc. Natl. Acad. Sci. U.S.A., 106(26):10666-10671 (2009) 7 pages. (NPL195).
Louie et al., "Pharmacodynamics of Levofloxacin in a Murine Pneumonia Model of Pseudomonas aeruginosa Infection Determination of Epithelial Lining Fluid Targets", Antimicrob Agents Chemother., 53(8):3325-3330 (2009) 6 pages. (NPL196).
Luidens et al., "Thyroid hormone and angiogenesis", Vascular Pharmacology, 52(3-4): 142-145 (2010) 4 pages. (NPL197).
Lyons et al., "The Expression of an N-CAM Serum Fragment is Positively Correlated with Severity of Negative Features in Type II Schizophrenia", Biol. Psychiatry, 23:769-775 (1988) 7 pages. (NPL198).
Ma, et al., "Use of Encapsulated Single Chain Antibodies for Induction of Anti-Idiotypic Humoral and Cellular Immune Responses", J. Pharm. Sci., 87:1375-1378 (1998). 4 pages. (NPL199).
Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages. (NPL200).
Bridoux et al., "Semisynthesis and pharmacological activities of Tetrac analogs: Angiogenesis modulators", Bioorg. Med. Chem. Lett., 19:3259-3263 (2009) 5 pages. (NPL051).
Bridoux et al., "Semisynthesis and pharmacological activities of thyroxine analogs: Development of new angiogenesis modulators", Bioorg. Med. Chem. Lett., 20(11):3394-3398 (2010) 5 pages. (NPL052).
Brockhoff et al., "Differential impact of Cetuximab, Pertuzumab and Trastuzumab on BT474 and SK-BR-3 breast cancer proliferation", Cell Prolif., 40:488-507 (2007) 20 pages. (NPL053).
Brooks et al., "Antintegrin $\alpha v \beta 3$ blocks human breast cancer growth and angiogenesis in human skin", J. Clin. Invest., 96(4):1815-1822 (1995) 8 pages. (NPL054).
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages. (NPL055).
Burgman et al., "Effect of Inhibitors of Poly(ADP-Ribose)Polymerase on the Radiation Response of HeLa S3 Cells", Radiat. Res., 119:380-386 (1989) 7 pages. (NPL056).
Carmeliet et al., "Molecular Basis of Angiogenesis Role of VEGF and VE-Cadherin", Ann. N.Y. Acad. Sci., 902:249-264 (2000) 16 pages. (NPL057).
Chanoine et al., "The role of transthyretin in the transport of thyroid hormone to cerebrospinal fluid and brain", Acta Medica Austriaca, 19(Suppl. 1):25-28 (1992) 5 pages. (NPL058).
Charness et al., "Ethanol Increases the Expression of Functional Delta-Opioid Receptors in Neuroblastoma x Glioma NG108-15 Hybrid Cells", J. Biol. Chem., 261(7):3164-3169 (1986) 6 pages. (NPL059).

Charo et al., "The Vitronectin Receptor $\alpha v \beta 3$ Binds Fibronectin and Acts in Concert with $\alpha 5 \beta 1$ in Promoting Cellular Attachment and Spreading on Fibronectin", J. Cell Biol., 111(6 Pt. 1): 2795-2800 (1990) 6 pages. (NPL060).
Chase et al., "Principles of Radioisotope Methodology", 2nd Ed., Minneapolis, MN. Burgess Publ. Co., 1962, pp. 68, 87-90. 7 pages. (NPL061).
Chavakis et al., "Kinetics of integrin expression in the mouse model of proliferative retinopathy and success of secondary intervention with cyclic RGD peptides", Diabetologia, 45:262-267 (2002) 6 pages. (NPL062).
Cheng et al., "Molecular Aspects of Thyroid Hormone Actions", Endocri. Rev., 31(2): 139-170 (2010) 32 pages. (NPL063).
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36): 17703-17711 (1987) 9 pages. (NPL064).
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages. (NPL065).
Chiaguri et al., "Anoikis: A necessary death program for anchorage-dependent cells", Biochem. Pharmacol., 76:1352-1364 (2008) 13 pages (NPL066).
Chinese Office Action for Application No. 2004800331846 dated Mar. 5, 2010 7 pages. (NPL067).
Chinese Office Action for Application No. 2004800331846, dated Nov. 30, 2007, cited CN 1126589. 6 pages. (NPL068).
Clifton et al., "Marked Protection by Moderate Hypothermia After Experimental Traumatic Brain Injury", J. Cereb. Blood Flow Metab., 11(1):114-121 (1991) 9 pages. (NPL069).
Cody et al., "Molecular modeling of the thyroid hormone interactions with $\alpha v \beta 3$ integrin", Steroids, 72:165-170 (2007) 6 pages. (NPL070).
Cohen-Jonathan et al., "Radioresistance Induced by the High Molecular Forms of the Basic Fibroblast Growth Factor is Associated with an increased G2 Delay and a Hyperphosphorylation of p34CDC2 in HeLa Cells", Cancer Res., 57:1364-1370 (1997) 7 pages. (NPL071).
Cohen-Jonathan et al., "$\alpha v \beta 3$ integrin pathway controls glioma radioresistance through ILK", Proc. Amer. Assoc. Cancer Res., 47:5180 (2006) (Abstract Only) 2 pages. (NPL072).
Cox et al., "The repair of potentially lethal damage in X-irradiated cultures of normal and ataxia telangiectasia human fibroblasts", Int. J. Radiat. Biol., 39(4)1357-365 (1981) 9 pages. (NPL073).
Cristofanilli et al., "Thyroid Hormone and Breast Carcinoma. Primary Hypothyroidism is Associated with a Reduced Incidence of Primary Breast Carcinoma", Cancer, 103(6)11122-1128 (2005) 7 pages. (NPL074).
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12)15694-5703 (2004) 10 pages. (NPL075).
Database BIOSIS [Online], Accession No. PREV20040016159, Abstiact, Mousa et al., "Discovery of pro-angiogenic affects of thyroid hormone and analogs", Blood, 102(11 ):77b-78b (2003) 1 page. SAME @ 221 and 365 (NPL076).
Davis et al., "Acting via a Cell Surface Receptor, Thyroid Hormone is a Growth Factor for Glioma cells," Cancer Res., 66(14)17270-7275 (2006) 6 pages. (NPL077).
Davis et al., "Cell-surface receptor for thyroid hormone and tumor cell proliferation", Expert Reviews of Endocrinology and Metabolism, 1(6)1753-761 (2006) 10 pages. (NPL078).
Davis et al., "Mechanisms of nongenomic actions of thyroid hormone", Frontiers Neuroendocrinol., 29:211-218 (2008) 3 pages. (NPL079).
Davis et al., "Proangiogenic Action of Thyroid Hormone is Fibroblast Growth Factor-Dependent and is initiated at the Cell Surface." Cir. Res., 94(2004):1500-1506 7 pages. (NPL080).
Davis et al., "Promotion by thyroid hormone of cytoplasm-to-nucleus shutting of thyroid hormone receptors", Steroids, 73:1013-1017 (2008) 5 pages. (NPL081).
Davis et al., "Thyroxine Promotes Association of Mitogen-activated Protein Kinase and Nuclear Thyroid Hormone Receptor (TR) and

(56) References Cited

OTHER PUBLICATIONS

Causes Serine Phosphorylation of TR", J. Biol. Chem., 275(48):38032-38039 (2000) 8 pages. (NPL082).
Davis et al., "Translational implications of nongenomic actions of thyroid hormone initiated at its integrin receptor", Am. J. Physiol. Endocrinol. Metab., 297:E1238-E1246 (2009) 9 pages. (NPL083).
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages. (NPL084).
Deardorff, D.L., "Isotonic Solutions", in Remington's Pharmaceutical Sciences, 15th Ed., Chapter 79, pp. 1405-1412, Mack Publishing Co., Easton (1975) 10 pages. (NPL085).
DeFesi et al., "3,5,3'-Triiodothyronine Effects on the Growth Rate and Cell Cycle of Cultured GC Cells", Endocrinol., 108(1):259-267(1981) 9 pages. (NPL086).
Demediuk et al., "Traumatic Spinal Cord Injury in Rats Causes Increases in Tissue Thromboxane But Not Peptidoleukotrienes", J. Neurosci. Res., 20:115-121 (1988) 7 pages. (NPL087).
DeRyck et al., "Neocortical localization of tactile/proprioceptive limb placing reactions in the rat", Brain Res., 573 (1):44-60 (1992) 18 pages. (NPL088).
Di Chiro et al., "Glucose utilization of cerebral gliomas measured by [18F] fluorodeoxyglucose and positron emission tomography", Neurology, 32(12): 1323-1329 (1982) 8 pages. (NPL089).
Dietrich et al., "Post-traumatic brain hypothermia reduces histopathological damage following concussive brain injury in the rat", Acta Neuropathol., 87(3):250-258 (1994) 10 pages. (NPL090).
Ding et al., "Radioprotection of Hematopoietic Tissue by Fibroblast Growth Factors in Fractionated Radiation Experiments", Acta Oncol., 36(3):337-340 (1997) 4 pages. (NPL091).
Dixon et al., "A fluid percussion model of experimental brain injury in the rat", J. Neurosurg., 67(1):110-119 (1987) 11 pages. (NPL092).
Drusano et al., "Pharmacodynamics of Abacavir in an In Vitro Hollow-Fiber Model System", Antimicrob. Agents Chemother., 46(2):464-470 (2002) 7 pages. (NPL093).
Dupont et al., "Antiangiogenic and antimetastatic properties of Neovastat (Æ941), an orally active extract derived from cartilage tissue", Clin. Experim. Metastasis, 19:145-153 (2002) 9 pages. (NPL094).
Edwards et al., "Trypsinized BHK21 cells aggregate in the presence of metabolic inhibitors and in the absence of divalent cations", J. Cell Sci., 19(3):653-667 (1975) 16 pages. (NPL095).
Elkind et al., "Radiation Response of Mammalian Cells Grown in Culture. 1. Repair of X-Ray Damage in Surviving Chinese Hamster Cells", Radiat. Res., 13:556-593 (1960) 38 pages. (NPL096).
Elvin et al., "Cell Adhesiveness and the Cell Cycle: Correlation in Synchronized Balb/c 3T3 Cells", Biol. Cell, 48:1-10 (1983) 10 pages. (NPL097).
Ely and Berne, "Protective Effects of Adenosine in Myocardial Ischemia", Circulation, 85:893-904 (1992) 13 pages. (NPL098).
Ethier et al., "Adenosine stimulates proliferation of human endothelial cells in culture", Am. J. Physiol., 265:H131-H138 (1993) 8 pages. (NPL099).
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages. (NPL100).
A.D.A.M. Medical Encyclopedia, www.ncbi.nlm.nih.gov/pubmedhealth/PMH0001308/, downloaded Jul. 12, 2012. 6 pages.
Abdollahi et al., "Inhibition of αvβ3 Integrin Survival Signaling Enhances Antiangiogenic and Antitumor Effects of Radiotherapy", Clin. Cancer Research., 11(17):6270-6279 (2005) 10 pages.
Albert et al., "Integrin αvβ3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.

Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-α in tumorigenesis: inhibition of cell growth and angiogenic factors", Cell Prolif., 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.
Almog et al., "Transcriptional Switch of Dormant Tumors to Fast-Growing Angiogenic Phenotype", Cancer Res., 69 (3):836-844 (2009).
Amirkhosravi et al., "Antimetastatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, Supplemental European Search Report dated Apr. 20, 2015. 7 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds solation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Application No. PCT/US2017/36396, International Search Report dated Sep. 1, 2017.
Application No. PCT/US2014/66154, International Search Report dated Jan. 27, 2015. 12 pages.

(56) References Cited

OTHER PUBLICATIONS

Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estiogen-dependent human breast cancers sensitive and resistant to tamoxifen", Proc. Natl, Acad. Sci. USA, 99(4):2211-2215 (2002) 5 pages.
Bergers et al., "Modes of resistance to anti-angiogenic therapy", Nat. Rev. Cancer, 8(8):592-603 (2008) 23 pages.
Bergh et al., "Integrin αvβ3 contains a cell surface receptor site for thyroid hormone that is linked to activation of mitogen-activated protein kinase and induction of angiogenesis", Endocrinology, 146 (7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.
Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bornebroek et al., "Potential for imaging cerebral amyloid deposits using 123I-labelled serum amyloid P component and SPET", Cucl. Med. Commun., 17:929-933 (1996) 6 pages.
Bozarth et al., "An improved method for the quantitation of cellular migration: Rose of αvβ3 integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Advisory Action (dated Feb. 27, 2008) for U.S. Appl. No. 10/943,072, filed Sep. 14, 2004.
Office Action (dated May 15, 2008) for U.S. Appl. No. 10/943,072, filed Sep. 14, 2004.
Office Action (dated Jan. 8, 2009) for U.S. Appl. No. 10/943,072, filed Sep. 14, 2004.
Office Action (dated Jun. 22, 2009) for U.S. Appl. No. 10/943,072, filed Sep. 14, 2004.
Notice of Allowance (dated Dec. 11, 2009) for U.S. Appl. No. 10/943,072, filed Sep. 14, 2004.
Office Action (dated Mar. 24, 2015) for U.S. Appl. No. 13/975,725, filed Aug. 26, 2013.
Final Office Action (dated Oct. 9, 2015) for U.S. Appl. No. 13/975,725, filed Aug. 26, 2013.
Advisory Action (dated Dec. 31, 2015) for U.S. Appl. No. 13/975,725, filed Aug. 26, 2013.
Office Action (dated Jun. 17, 2016) for U.S. Appl. No. 13/975,725, filed Aug. 26, 2013.
Final Office Action (dated Apr. 3, 2017) for U.S. Appl. No. 13/975,725, filed Aug. 26, 2013.
Notice of Allowance (dated Jan. 31, 2018 U.S. Appl. No. 13/975,725, filed Aug. 26, 2013.
Office Action (dated May 12, 2015) for U.S. Appl. No. 14/078,713, filed Nov. 13, 2013.
Notice of Allowance (dated Aug. 3, 2015) for U.S. Appl. No. 14/078,713, filed Nov. 13, 2013.
Restriction Requirement (dated Dec. 3, 2015) for U.S. Appl. No. 14/184,889, filed Feb. 20, 2014.
Office Action (dated May 6, 2016) for U.S. Appl. No. 14/184,889, filed Feb. 20, 2014.
Notice of Allowance (dated Oct. 13, 2016) for U.S. Appl. No. 14/184,889, filed Feb. 20, 2014.
Restriction Requirement (dated Dec. 2, 2015) for U.S. Appl. No. 14/185,010, filed Feb. 20, 2014.
Office Action (dated Sep. 9, 2016) for U.S. Appl. No. 14/185,010, filed Feb. 20, 2014.
Notice of Allowance for U.S. Appl. No. 14/185,010 (dated Apr. 4, 2017).
Office Action (dated Oct. 14, 2014) for U.S. Appl. No. 14/242,041, filed Apr. 2, 2014; (Prosecution Not Cited but Prior Art References Were).
Office Action (dated Jun. 11, 2015) for U.S. Appl. No. 14/242,041, filed Apr. 1, 2014.
Final Office Action (dated Oct. 16, 2015) for U.S. Appl. No. 14/242,041, filed Apr. 1, 2014.
Advisory Action (dated Jan. 21, 2016) for U.S. Appl. No. 14/242,041, filed Apr. 1, 2014.
Office Action (dated May 26, 2016) for U.S. Appl. No. 14/242,041, filed Apr. 2, 2014; (Prosection Not Cited but Prior Art References Were).
Notice of Allowance (dated Jul. 19, 2016) for Patent No. U.S. Appl. No. 14/242,041, filed Apr. 1, 2014.
Restriction Requirement (dated Nov. 4, 2015) for U.S. Appl. No. 14/546,440, filed Nov. 18, 2014.
Office Action (dated Mar. 24, 2016) for U.S. Appl. No. 14/546,440, filed Nov. 18, 2014.
Office Action (dated Sep. 30, 2016) for U.S. Appl. No. 14/546,440, filed Nov. 18, 2014.
Office Action (dated Oct. 4, 2017) for U.S. Appl. No. 14/546,440, filed Nov. 18, 2014.
Notice of Allowance (dated May 3, 2018) for U.S. Appl. No. 14/546,440, filed Nov. 18, 2014.
Restriction Requirement (dated Feb. 9, 2017) for U.S. Appl. No. 15/056,522, filed Feb. 29, 2016.
Office Action (dated Jun. 13, 2018) for U.S. Appl. No. 15/056,522, filed Feb. 29, 2016.
Office Action (dated Feb. 15, 2019) for U.S. Appl. No. 15/056,522, filed Feb. 29, 2016.
Office Action (dated Jun. 11, 2018) for U.S. Appl. No. 14/903,149, filed Jan. 6, 2016.
Final Office Action (dated Mar. 13, 2019) for U.S. Appl. No. 14/903,149, filed Jan. 6, 2016.
Office Action (dated Dec. 29, 2017) for U.S. Appl. No. 15/357,818, filed Nov. 21, 2016.
Office Action (dated Apr. 20, 2018) for U.S. Appl. No. 15/357,818, filed Nov. 21, 2016.
Notice of Allowance (dated Jul. 3, 2018) for U.S. Appl. No. 15/357,818, filed Nov. 21, 2016.
Office Action (dated May 10, 2018) for U.S. Appl. No. 15/616,637, filed Jun. 7, 2017.

(56) References Cited

OTHER PUBLICATIONS

Notice of Allowance (dated Sep. 2, 2018) for U.S. Appl. No. 15/616,637, filed Jun. 7, 2017.
Restriction Requirement (dated Oct. 12, 2018) for U.S. Appl. No. 15/950,870, filed Apr. 11, 2018.
Office Action (dated Nov. 28, 2018) for U.S. Appl. No. 15/950,870, filed Apr. 11, 2018.
Notice of Allowance (dated Feb. 6, 2019) for U.S. Appl. No. 15/950,870, filed Apr. 11, 2018.
Restriction Requirement (dated Sep. 11, 2019) for U.S. Appl. No. 16/223,176, filed Dec. 18, 2018.
Notice of Allowance (dated Feb. 26, 2020) for U.S. Appl. No. 16/223,176, filed Dec. 18, 2018.
Application No. PCT/US19/025489, International Search Report and the Written Opinion Opinion dated May 1, 2019. 8 pages. (53227PCT).
Kawai, "Excerpt of table 1 from Biodegration of Polyethers (Polyethylene Glycol, Polypropylene Glycol, Polytetramethylene glycol, and Others)." In: "Biopolymers : [biology, chemistry, biotechnology, applications]," Jan. 15, 2005, Wiley-VCH, Weinheim [u.a.], XP55655138.
Kawai, "Biodegradation of Polyethers (Polyethylene Glycol, Polypropylene Glycol, Polytetramethylene glycol, and Others)," Biopolymers: Part 9. Miscellaneous Biopolymers and Biodegradation of Polymers, Jan. 15, 2015, XP055655101, Retrieved from the Internet: URL:https://onlinelibrary.wiley.com/doi/full/10.1002/3527600035.bpol9012 [retrieved on Jan. 7, 2020].
Extended European Search Report in related European Patent Application No. 17810954.2, dated Jan. 30, 2020; 9 pages.

* cited by examiner

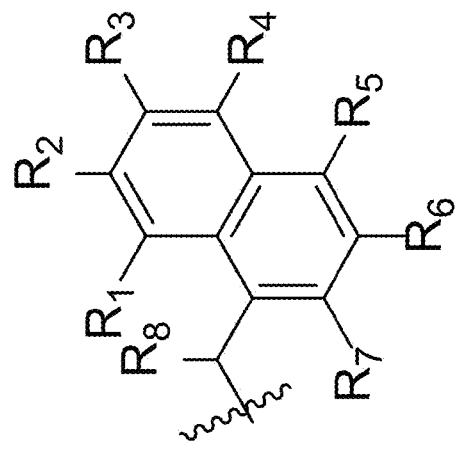
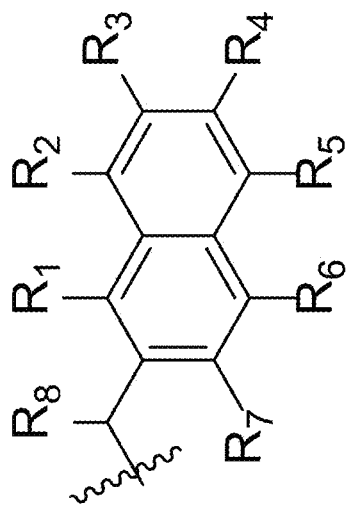
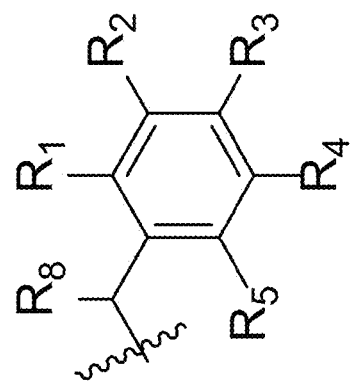
FIG. 9B
FIG. 9C
FIG. 9A

COMPOSITION OF SCALABLE THYROINTEGRIN ANTAGONISTS WITH IMPROVED RETENTION IN TUMORS

CROSS-REFERENCE TO RELATED APPLICATIONS

The present application claims priority to U.S. Nonprovisional application Ser. No. 16/862,076, filed on Apr. 29, 2020, and entitled "COMPOSITION OF SCALABLE THYROINTEGRIN ANTAGONISTS WITH IMPROVED BLOOD BRAIN BARRIER PENETRATION AND RETENTION IN BRAIN TUMORS," now U.S. Pat. No. 10,961,204 issued Mar. 30, 2021, the entire contents of which are hereby incorporated by reference.

TECHNICAL FIELD

The present disclosure relates generally to improved thyroid hormone receptor antagonists (referred to as "thyrointegrin antagonists") compounds along with compositions comprising the same, methods of using such compounds and compositions for treating conditions, and methods of synthesis. More specifically the present disclosure relates to compounds comprising alpha-V-beta-3 ($\alpha v \beta 3$) integrin-thyroid hormone receptor antagonists conjugated to a polymer, wherein the polymer is also conjugated to a further substituent or functional group. The disclosed compounds, and compositions utilizing the compounds, have improved blood brain barrier penetration and retention, improved synthesis scalability, aqueous solubility, and/or solid products or intermediates. The compounds are also subject to readily scalable purification, for example by normal phase chromatography. Due to the increased penetration across the blood brain barrier and retention into brain tumors, the disclosed compositions and compounds are especially effective for treating certain conditions, for example Glioblastoma, Gliomas, Astrocytoma, CNS Lymphoma, Medulloblastoma, Meningioma, Metastatic Brain Tumors, Pituitary Tumors, Primitive Neuroectodermal (PNET), and Other Brain-Related Conditions.

BACKGROUND

Integrins are a super-family of cell surface adhesion receptors, which control the attachment of cells with the solid extracellular environment, both to the extracellular matrix (ECM), and to other cells. Adhesion is of fundamental importance to a cell; it provides anchorage, cues for migration, and signals for growth and differentiation. Integrins are directly involved in numerous normal and pathological conditions, and as such are primary targets for therapeutic intervention. Integrins are integral transmembrane proteins, heterodimers, whose binding specificity depends on which of the 14 $\alpha$-chains are combined with which of the 8 $\beta$-chains. The integrins are classified in four overlapping subfamilies, containing the $\beta 1$, $\beta 2$, $\beta 3$ or $\alpha v$ chains. A cell may express several different integrins from each subfamily. In the last several decades, it has been shown that integrins are major receptors involved in cell adhesion, and so may be a suitable target for therapeutic intervention. Integrin $\alpha v \beta 3$ regulates cell growth and survival, since ligation of this receptor can, under some circumstances, induce apoptosis in tumor cells. Disruption of cell adhesion with anti-$\alpha v \beta 3$ antibodies, RGD peptides, and other integrin antagonists has been shown to slow tumor growth such as the cyclic peptide Cilengitide that failed in Phase 3 Glioblastoma trial because of its limited blood brain barrier permeability and brain tumor retention.

Applicant has previously disclosed compounds and compositions comprising non-cleavable polymer conjugated with $\alpha v \beta 3$ integrin thyroid antagonists as well as related methods, for example in U.S. patent application Ser. No. 15/616,637, now U.S. Pat. No. 10,201,616 and U.S. patent application Ser. No. 16/223,176, the entire contents of both of which are hereby incorporated by reference.

Further, Applicant has previously disclosed compounds, compositions and methods comprising $\alpha v \beta 3$ integrin thyroid antagonists and targets of the norepinephrine transporter or the catecholamine transporter (for example, benzyl guanidine or derivatives) as well as related methods, for example in U.S. patent application Ser. No. 15/950,870, now U.S. Pat. No. 10,328,043 and U.S. patent application Ser. No. 16/398,342, the entire contents of both of which are hereby incorporated by reference.

While the compounds, compositions and methods described in these previous applications and issued patents were improvements to the then-existing state of the art, such compounds and compositions may suffer from one or more drawbacks including low blood brain barrier permeability, poor synthesis scalability, lack of aqueous solubility, and the lack of formation of solid product or intermediate. Purification may also present difficulties. The disclosed compounds and compositions comprising these compounds include improvements in these areas and demonstrate unexpected efficacy in treating glioblastoma, other brain tumors, and similar conditions.

Blood brain barrier permeability is important for targeting certain conditions, for example gliomas, meningiomas, pituitary adenomas, vestibular schwannomas, and medulloblastomas. Glioblastoma (glioblastoma multiforme or GBM) is one specific example of such a condition that requires blood brain barrier permeability for effective treatment. It is conventional in the art that drug delivery methods having improved blood brain barrier permeability would be beneficial. See e.g., Bhowmik A, Khan R, Ghosh M K. Blood Brain Barrier: A Challenge for Effectual Therapy of Brain Tumors. BioMed Research International, Volume 2015; Upadhyay R K. Drug Delivery Systems, CNS Protection, and the Blood Brain Barrier. BioMed Research International, Volume 2014. The improved compounds, compositions, and methods described herein demonstrate improved blood brain barrier permeability and offer vastly improved efficacy for these types of conditions. Further, the improved compounds, compositions, and methods described herein demonstrate improved retention within the brain, particularly at the site of tumors located within the brain. This improved retention provides a further increased efficacy in treating such conditions. The improved compounds, compositions, and methods described herein also demonstrate improved scalability and solubility and may yield a solid product or intermediate.

A compound or composition such as those described herein comprising an $\alpha v \beta 3$ integrin-thyroid hormone receptor antagonist (thyrointegrin antagonist) and having the described improved blood brain barrier penetration and retention would be well received in the art, as would the treatment methods using such compounds and/or compositions. Further, compounds or compositions having such improved blood brain barrier penetration together with one or more of the described improved synthesis scalability, aqueous solubility, and/or formation of solid products or intermediates would likewise be well received in the art.

SUMMARY

According to one aspect, a compound comprises a thyrointegrin antagonist; a non-biodegradable polymer; a linker covalently bound to the thyrointegrin antagonist and the non-biodegradable polymer via a non-cleavable covalent bond; and a substituent A bound to the non-biodegradable polymer.

According to another aspect, a compound comprises a general formula:

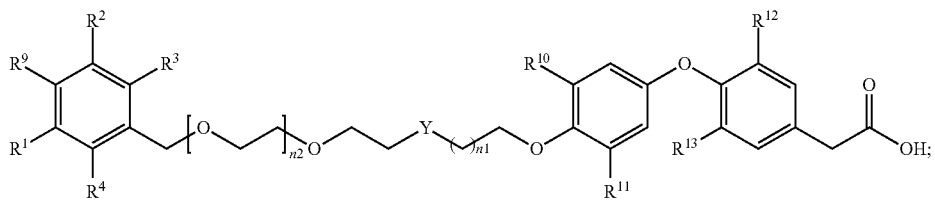

wherein n1≥0; wherein n2 is 5-200; wherein R1-R4 and R9 are independently selected from the group consisting of: H, Me, Et, iPr, nPr, nBu, iBu, secBu, tBu, $C_5$-$C_{12}$ n-alkyl, cyclopentyl, cyclohexyl, phenyl, F, Cl, Br, I, CN, $CF_3$, $OCF_3$, $CHF_2$, $OCHF_2$, $SO_2Me$, $NO_2$, —O-Alkyl, —O-Aryl, —$CH_2$—O-Alkyl, —$CH_2$—O-Aryl, Esters, and Amides; wherein R10-R13 are each independently selected from the group consisting of hydrogen, iodine, and an alkane group; and wherein Y is selected from the group consisting of:

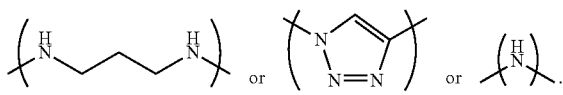

According to another aspect, a compound comprises a thyrointegrin antagonist conjugated to a polymer; and a substituted benzyl conjugated to the polymer; wherein the compound is absorbed across the blood brain barrier.

According to another aspect, a method of treating comprises providing a compound having a thyrointegrin antagonist and a substituted benzyl connected by a polymer; and administering a therapeutically effective amount of the compound to a patient in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the embodiments will be described in detail with reference made to the following figures, in which like designations denote like members, wherein:

FIG. 9A depicts an embodiment of Substitution A from FIG. 1 in accordance with an embodiment of the invention;
FIG. 9B depicts another embodiment of Substitution A from FIG. 1 in accordance with an embodiment of the invention;
FIG. 9C depicts another embodiment of Substitution A from FIG. 1 in accordance with an embodiment of the invention.

DETAILED DESCRIPTION

A detailed description of the hereinafter-described embodiments of the disclosed composition and method is presented herein by way of exemplification and not limitation with reference to the Figures. Although certain embodiments are shown and described in detail, it should be understood that various changes and modifications might be made without departing from the scope of the appended claims. The scope of the present disclosure will in no way be limited to the number of constituting components, the materials thereof, the shapes thereof, colors thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Overview

Embodiments of the present disclosure describe new chemical compounds, compositions comprising the new chemical compounds, methods of synthesis thereof, and methods of treatment using such compounds and compositions.

The compounds disclosed herein (including but not limited to the exemplary compounds such as Compound 2, Compound 3, Compound 4, and Compound 5 described in detail below, along with compositions prepared from such compounds) demonstrate improved blood brain barrier penetration and retention into brain tumors. Further, these compounds and their respective compositions show an unexpected increase in efficacy against brain tumors and other conditions, for example glioblastoma (GBM).

The unexpected increase in efficacy against these conditions may be due to a complex of factors—including active transport across the blood brain barrier, overexpression of integrin $\alpha v\beta 3$ in GBM and similar conditions, and effect of further substituents on the thyrointegrin antagonist on uptake/retention.

First, the compounds and compositions described herein comprise a thyrointegrin antagonist. Thyrointegrin antagonists such as those described herein may be subject to active transport across the blood brain barrier by thyroid binding proteins. A discussion of the transport of thyroid hormone and its analogs in the brain may be found at Wirth E K, Schwiezer U, Kohrle J. Transport of thyroid hormone in brain. Frontiers in Endocrinology. June 2014, Volume 5, Article 98. Drug delivery methods having improved blood brain barrier permeability may be difficult to achieve; however, Applicant's disclosed compounds and compositions are actively transported across the blood brain barrier and thus reach the intended target site for therapeutic activity.

Figure 19:
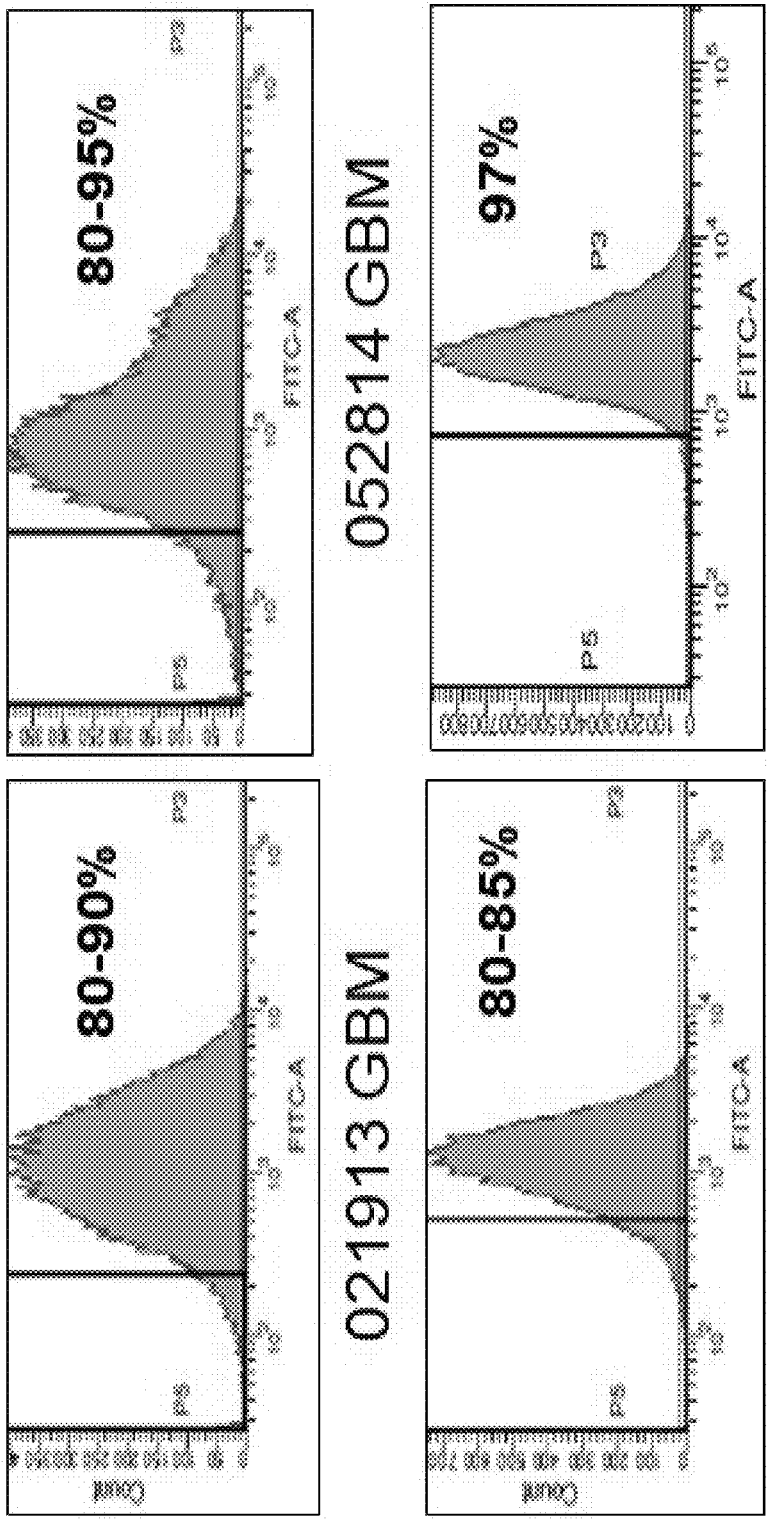
FIG. 19 depicts expression levels of integrin $\alpha v\beta 3$ in glioblastoma cancer cells analyzed by flow cytometry.

Second, the compounds and compositions described herein may be retained within the blood brain barrier due to overexpression of integrin $\alpha v\beta 3$ on GBM and similar conditions. For example, expression of $\alpha v\beta 3$ in GBM may reach levels of 80-97% as shown in FIG. 19. Like other thyrointegrin antagonists, the disclosed compounds may bind to this integrin binding site. Thus, in addition to being transported into the brain, the described compounds and compositions bind to the tumor cells and may be retained within the blood brain barrier and retained at the intended target site. Further, this reduces any unintended effect on non-tumor tissue.

Figure 20:
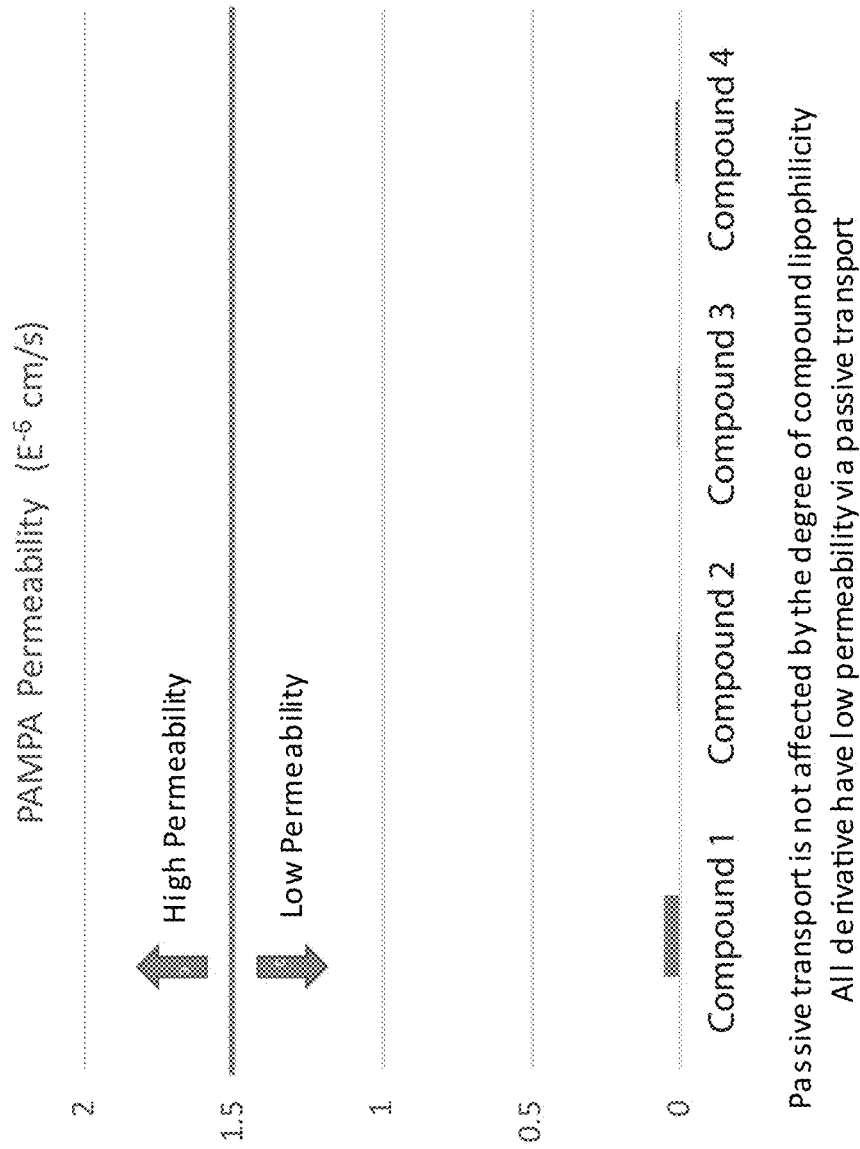
FIG. 20 depicts the results of a parallel artificial membrane permeability assay (PAMPA) for exemplary Compounds 1-4.

Third, as described in more details below, the compounds and compositions described herein include additional functional groups. These additional functional groups may also be conjugated to the polymer. For example, in embodiments having linear polymers, the additional functional group may be conjugated on the opposite side of the polymer than the thyrointegrin antagonist. Non-linear polymers may also be used. The additional functional groups may further improve blood brain barrier penetration and retention and may also improve the scalability and/or solubility. For example, the increased uptake is not via passive transport since (as shown by FIG. 20 below) analysis by passive transport parallel artificial membrane permeability assay (PAMPA) shows low permeability of all derivatives in the absence of thyroid binding proteins. Instead, the additional functional group increase active transport, for example, by making the thyrointegrin antagonist (transporter target) more accessible. PAMPA was carried out for PMT36 and related compounds 2-4 where all exhibited low permeability (less than 1.5×E-6 cm/s). Similarly, low permeability of <1.5 E-6 cm/s was shown with Compound 5 as well as P-bi-TAT (a compound discussed in U.S. patent application Ser. No. 15/616,637, now U.S. Pat. No. 10,201,616, and U.S. patent application Ser. No. 16/223,176). The results suggest that these compounds do not permeate through the blood brain barrier via passive diffusion, which clearly suggest that BBB permeability to be facilitated mainly via the active transport system using thyroid binding proteins in blood such as transthyretin (TTR), which deliver the bound complex across the blood brain barrier.

Exemplary compounds will now be discussed in more detail along with additional background information regarding potential thyrointegrin antagonists and polymers that may be used in embodiments of the invention.

As discussed in U.S. patent application Ser. No. 15/616,637, now U.S. Pat. No. 10,201,616, and U.S. patent application Ser. No. 16/223,176, incorporated by reference above, compounds or compositions comprising an αvβ3 integrin-thyroid hormone receptor antagonist may include an anti-angiogenic thyroid hormone or derivative thereof conjugated via a non-cleavable linker to a polymer, forming a single chemical entity which may considered a micro molecule or macromolecule (depending on the size of the polymer covalently bound to the thyroid hormone or derivative thereof). The size of the single chemical entity and the strength of the non-cleavable covalent bond may be advantageous for preventing the thyroid hormone or derivative thereof from entering cells comprising a cell surface receptor of the integrin αvβ3 variety. Due to the size of the attached polymer, and the inability of the surrounding environment of the cell to cleave the strong, uncleavable covalent bonds of the thyroid hormone from the polymer, the thyroid hormone portion of the described chemical entities may be unable to be internalized within the nucleus of the cells which the thyroid hormone or derivative thereof may interact. Accordingly, the thyroid hormone portion may interact with the cells non-genomically and avoid genomic interactions that may be caused by thyroid hormones or derivatives thereof entering a cell and interacting with the nuclear receptors of the cellular nucleus.

As discussed in U.S. patent application Ser. No. 15/616,637, now U.S. Pat. No. 10,201,616, and U.S. patent application Ser. No. 16/223,176, incorporated by reference above, compounds or compositions comprising an αvβ3 integrin-thyroid hormone receptor antagonist may be synthesized to include, but are not limited to entities comprising non-biodegradable polymers such as polyethylene glycol (PEG) (1,000-15,000 Daltons, for example between 4,000-8,000 Daltons), a, 3, or 7 cyclodextrins, chitosan, alginic acid or hyaluronic acid, conjugated via non-cleavable linker comprising an amine or triazole bond, without short chain of PEG (100-800 M.W.) to an αvβ3 thyroid antagonist. Embodiments of the thyroid antagonists conjugated to the polymers may include tetraiodothyroacetic acid (tetrac), triiodothyroacetic acid (triac), derivatives thereof and variations thereof. Examples of one or more variations of the thyroid hormone antagonists comprising tetrac and triac may include, in some embodiments Diaminotetrac (DAT) or Diamnotriac (DATri) (hereinafter may be referred to interchangeably as "DAT"), Monoaminotetrac (MAT) or Monoaminotriac (MATri) (hereinafter referred to interchangeable as "MAT"), Triazoletetrac (TAT) or Triazoletriac (TATri) (hereinafter referred to interchangeably as "TAT"), derivatives thereof or other thyroid antagonist known by those skilled in the art.

As discussed in U.S. patent application Ser. No. 15/616,637, now U.S. Pat. No. 10,201,616, and U.S. patent application Ser. No. 16/223,176, incorporated by reference above, compounds or compositions comprising an αvβ3 integrin-thyroid hormone receptor antagonist have been further synthesized and characterized as DAT, MAT, or TAT conjugated to different molecular weights of Polyethylene Glycol (1,000 to 15,000 Dalton). We have scaled up embodiments of the relatively most soluble, PEG-DAT (P-MonoDAT, P-bi-DAT) and PEG-TAT (P-Mono-TAT, P-bi-TAT), for biological characterization in various in vitro and in vivo biological systems. Chemical labelling of DAT or TAT and PEG-DAT or PEG-TAT as well as C-DAT and C-TAT for imaging and cellular kinetics. Data revealed that polymer conjugation to DAT or TAT resulted in the restriction of cell nuclear uptake of those polymers conjugated DAT or TAT versus intense cell nuclear uptake of DAT or TAT. The result of this unique cellular distribution lead to the lack of genomic action of the polymer conjugated DAT, MAT or TAT versus the non-conjugated ones. Other Polymers such as Hyaluronic, Alginic acid, Chitosan conjugated to DAT, MAT or TAT with or without short chain short chain PEG (100-1,000 Dalton) are described. Additional Polymer conjugation to DAT, MAT or TAT were synthesized using bi-functional or tetra-function PEG may include, but it could also include other branched PEG up to 8 chains.

As discussed in U.S. patent application Ser. No. 15/616,637, now U.S. Pat. No. 10,201,616, and U.S. patent application Ser. No. 16/223,176, incorporated by reference above, compounds or compositions comprising an αvβ3 integrin-thyroid hormone receptor antagonist may have multiple types of utility for treating a plurality of different diseases modulated by angiogenesis or the inhibition thereof. The compositions, in view of presence of the thyroid antagonist present in the described compositions, may each have an affinity for targeting the integrin receptor αvβ3 located on numerous types of cells found throughout the human body and various animal bodies. For example, compositions may be useful for treating angiogenesis-mediated disorders such as Cancer (Solid tumors and Liquid tumors) in humans or mammals. Cancers may include Glioblastoma, pancreatic, ovarian, breast, prostate, bladder, lung and liver cancer. Liquid tumors may also include acute myeloid leukemia, multiple myeloma, Lymphoma and chronic lymphocytic leukemia. The compositions may further treat ocular disorders (Diabetic Retinopathy and Age-related Macular Degeneration), inflammatory disorders (arthritis, osteoarthritis), atherosclerosis lesions, and dermatology (Rosacea, Psoriasis, skin cancer) which may each be mediated or dependent upon the generation of new blood cells via angiogenesis to persist and the treatment thereof may be dependent antagonizing the formation of new blood vessel to slow or eliminate the angiogenic pathways.

The compounds and compositions disclosed herein improve upon Applicant's previously disclosed compounds and compositions in that they may achieve one or more of effective blood brain barrier penetration and retention, good synthesis scalability, good aqueous solubility, and yield a solid product amenable to scalable purification.

Reference may be made herein to specific thyrointegrin compounds, for example, tetrac, triac, etc. These phrases include derivatives of such compounds in accordance with the full teachings of this disclosure, even where such derivatives are not specifically listed.

Figure 1:
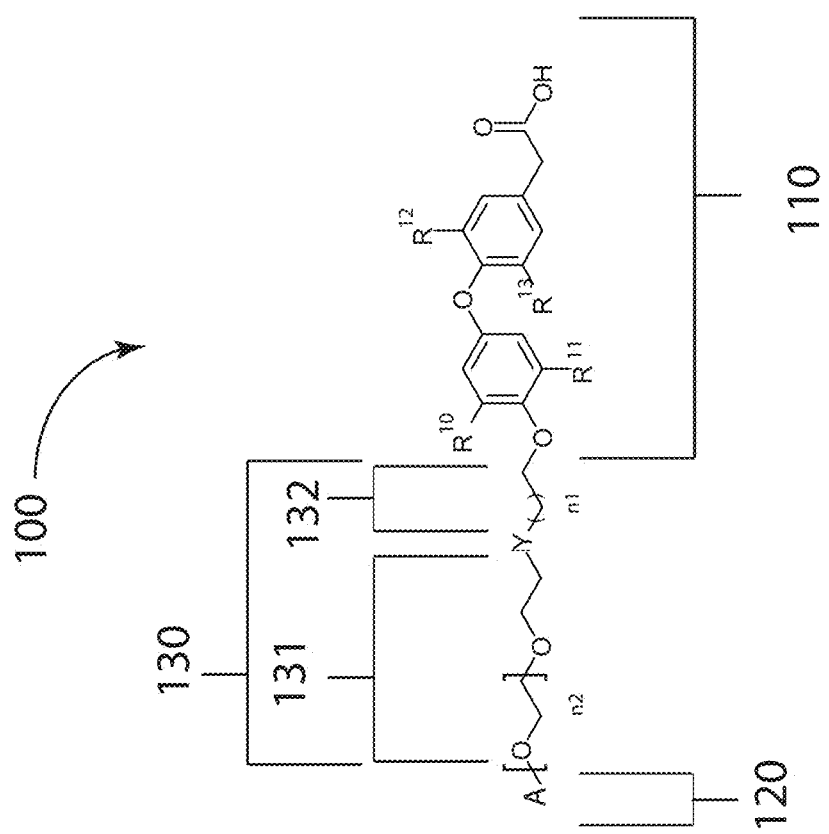
FIG. 1 depicts a general formula of an exemplary compound in accordance with an embodiment of the invention.

Referring to the drawings, FIG. 1 depicts an embodiment of a general formula 100 comprising a thyrointegrin antagonist 110 joined to a substituent 120 (depicted generally as "A"), via a linker 130. Hereinafter, the substituent may be referred to as substituent A, substituent 120, or as substituent A 120. FIG. 1 depicts a carboxylic acid form of the general formula 100, as may other Figures present in this application. As would be apparent to one skilled in the art, a salt (e.g. a sodium salt) of the general formula 100 may also be used.

In the depicted embodiment, the linker 130 comprises a spacer 132 and a polymer 131. The linker 130 resists biodegradation such that the linker remains uncleaved under physiological conditions. In one embodiment, the spacer 132 comprises a $CH_2$ unit and an adjacent repeating linkage of methylene ($CH_2$) units which may be defined by n1 repeats wherein n1 is an integer that is ≥0. In other embodiments, n1 may be ≥1, ≥2 or ≥3. The linker 130 further comprises a moiety "Y." Embodiments of the moiety "Y", may in some instances be may be an amine. For example, the moiety Y of the general formula may be a divalent alkane having one amine group or a divalent alkane having two amine groups as known from Applicant's previous applications. In another embodiment, the moiety Y may be a triazole as shown by the example of general formula 102 shown in FIG. 3. The polymer 131 may comprise a polyether such as polyethylene glycol (PEG). Other polymers may be used, including chitosan, alginic acid, hyaluronic acid, and other polymers. In embodiments using PEG as the polymer 131, the polymer may have a molecular weight between 200 and 4,000 g per mole.

The term thyrointegrin antagonist describes a compound that has the ability to inhibit or antagonize one or more thyroid hormone receptors known by a person skilled in the art, for example the integrin family of thyroid hormone receptors, such as the thyroid hormone cell surface receptor αvβ3. The thyrointegrin antagonist 110 may be an anti-angiogenic thyroid hormone or a thyroid hormone receptor antagonist. For example, the thyrointegrin antagonist 110 may be an alpha-V-beta-3 (αvβ3) integrin-thyroid hormone receptor antagonist.

Specific embodiments of the thyrointegrin antagonist 110 may include tetraiodothyroacetic acid (tetrac), triiodothyroacetic acid (triac), derivatives thereof and variations thereof. Examples of one or more variations of the thyrointegrin antagonist comprising tetrac and triac may include, in some embodiments Diaminotetrac (DAT) or Diaminotriac (DATri) (hereinafter may be referred to interchangeably as "DAT"), Monoaminotetrac (MAT) or Monoaminotriac (MATri) (hereinafter referred to interchangeable as "MAT"), Triazoletetrac (TAT) or Triazoletriac (TATri) (hereinafter referred to interchangeable as "TAT"), derivatives thereof or other thyroid antagonist known by those skilled in the art. Thyrointegrin antagonists may be of the types described in U.S. patent application Ser. No. 15/616,637 now U.S. Pat. No. 10,201,616 and U.S. patent application Ser. No. 16/223, 176, the entire contents of both of which are hereby incorporated by reference and/or in U.S. patent application Ser. No. 15/950,870 now U.S. Pat. No. 10,328,043 and U.S. patent application Ser. No. 16/398,342, the entire contents of both of which have been incorporated by reference. As described in those documents, in some embodiments of the thyrointegrin antagonist 110, the variables depicted as R10, R11, R12, and R13 may each independently be substituted for molecules such as hydrogen, iodine, and alkanes. In some embodiments, the alkanes have four or fewer carbons.

In embodiments of the invention, the substituent A 120 may be or comprise an aryl group and/or an aromatic group. For example, in embodiments, the substituent A 120 may comprise a benzyl group, a phenyl group, and the like. In some embodiments the substituent A 120 may comprise a substituted benzyl group. In further embodiments, a heterobenzyl group may be used. Still further, 5 membered ring heteroaryls, fused heteroaryls, qinolines, and indoles may also be used. The heteroaryls may comprise heteroarylmethyls. In further embodiments the substituent A 120 may comprise esters and amides.

Figure 2:
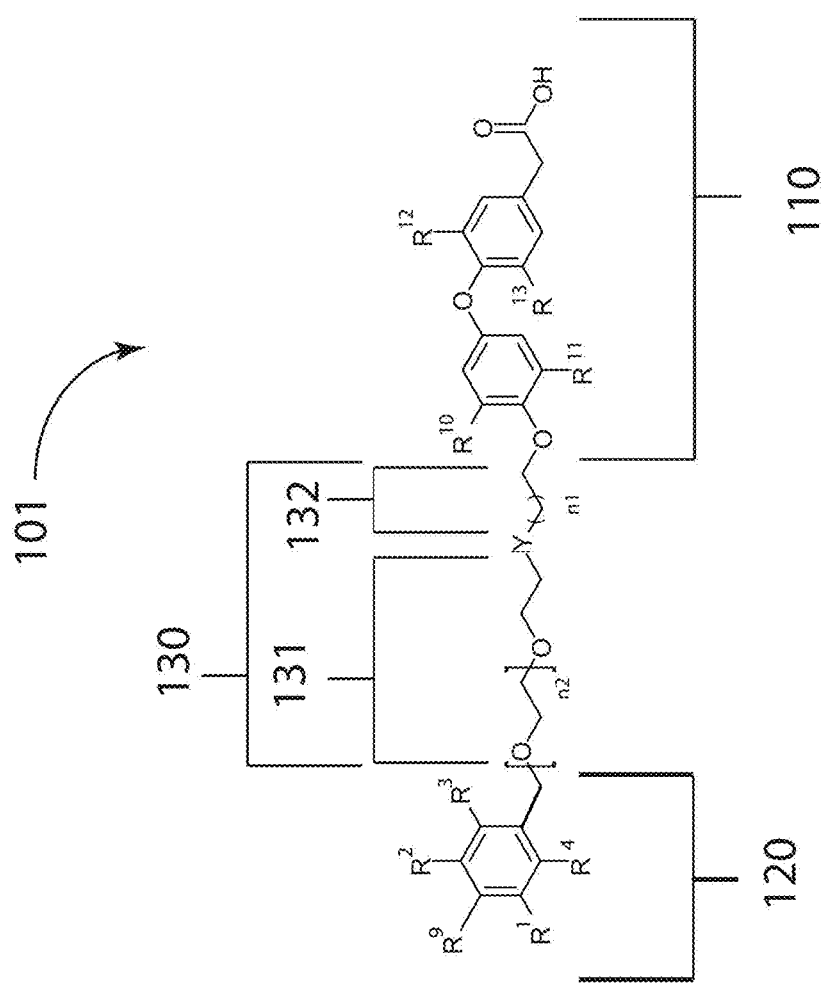
FIG. 2 depicts a further detailed general formula of an exemplary compound in accordance with an embodiment of the invention.

FIG. 2 depicts a general formula 101 in which the substituent A 120 is depicted as comprising an aromatic ring according to embodiments. The substituent A 120 comprising the aromatic ring may be, for example, a substituted benzyl group. In embodiments, the substituent A 120 comprising the aromatic ring may be substituted at one or more of R1, R2, R3, R4, and R9. In some embodiments of the substituent A 120 comprising the aromatic ring, the variables depicted as R1, R2, R3, R4, and R9 may be each independently be substituted for molecules such as hydrogen, iodine, fluorine, bromine, a methoxy group, a nitro group, an amine group, and a nitrile group. For example, in some embodiments of the substituent A 120 comprising the aromatic ring, the variables depicted as R1, R2, R3, R4, and R9 may be each independently be substituted for molecules of hydrogen, iodine, fluorine, bromine, a methoxy group, a nitro group, an amine group, and a nitrile group as described in Table 2 of U.S. patent application Ser. No. 15/950,870 now U.S. Pat. No. 10,328,043 and U.S. patent application Ser. No. 16/398,342. Still further, the variables depicted as R1, R2, R3, R4, and R9 may be substituted with alkyls, aryls, halos, amides, and the like.

Figure 3:
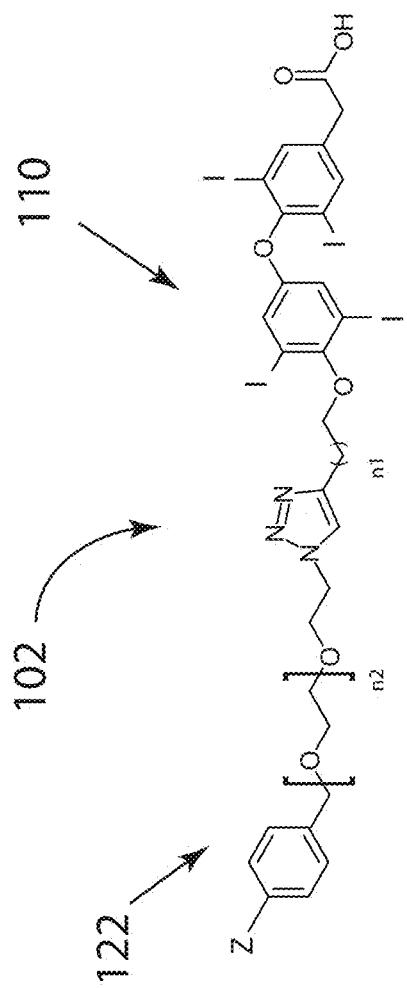
FIG. 3 depicts a further detailed general formula of an exemplary compound in accordance with an embodiment of the invention.
Figure 6:
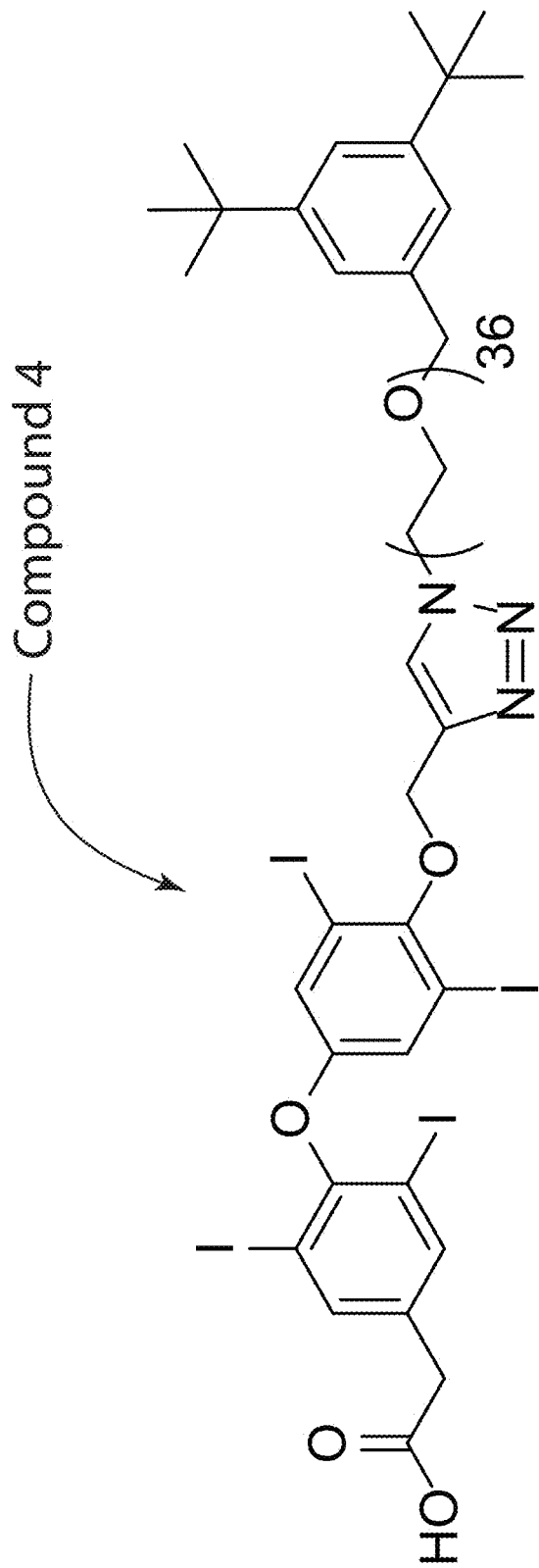
FIG. 6 depicts exemplary Compound 4.

As shown in FIG. 3, in some embodiments including the depicted general formula 102, the variables R1, R2, R3, R4 may be substituted for molecules of hydrogen while R9 may be substituted for a different molecule or group, "Z" in the depicted embodiment. Thus, the substituent A 120 may comprise an aromatic ring as discussed above, and may more specifically comprise a substituted benzyl group 122 in which the molecule or group Z has been substituted for hydrogen at R9. Alternatively, as shown in FIG. 6, in some embodiments, variables R1 and R2 or other variables may be substituted instead of R9.

Each of the exemplary Compounds shown in FIGS. 3-8 (including exemplary Compounds 1-5) comprises tetrac as the pertinent thyrointegrin αvβ3 receptor antagonist, polyethylene glycol as the pertinent linker, and a triazole as the included Y moiety.

Figure 4:
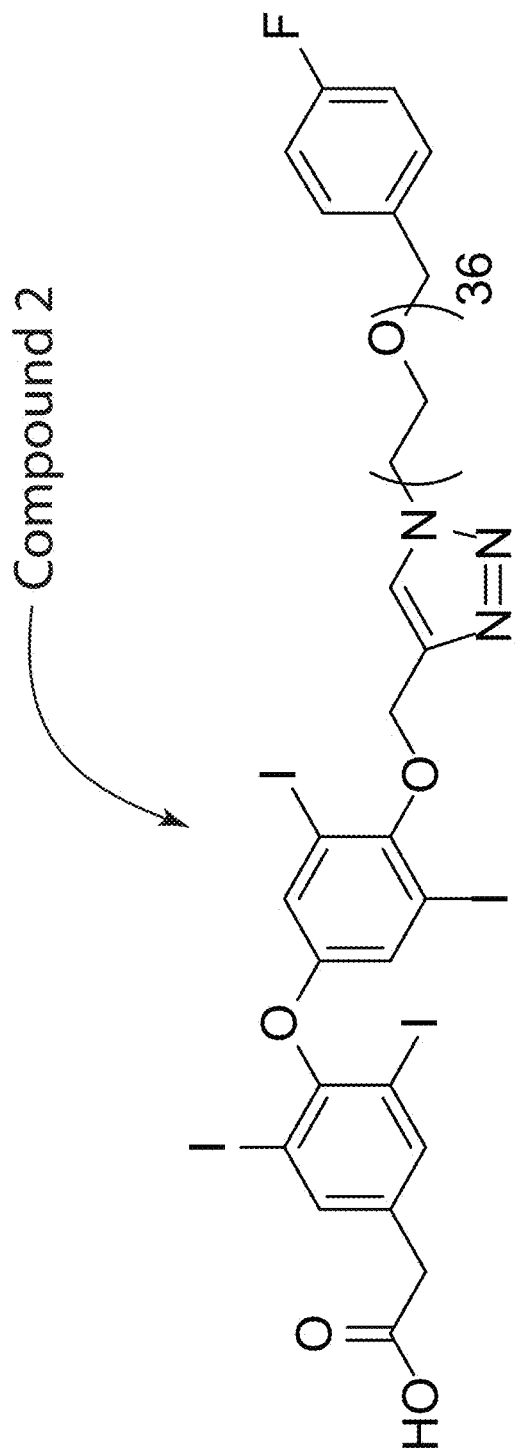
FIG. 4 depicts exemplary Compound 2.
Figure 5:
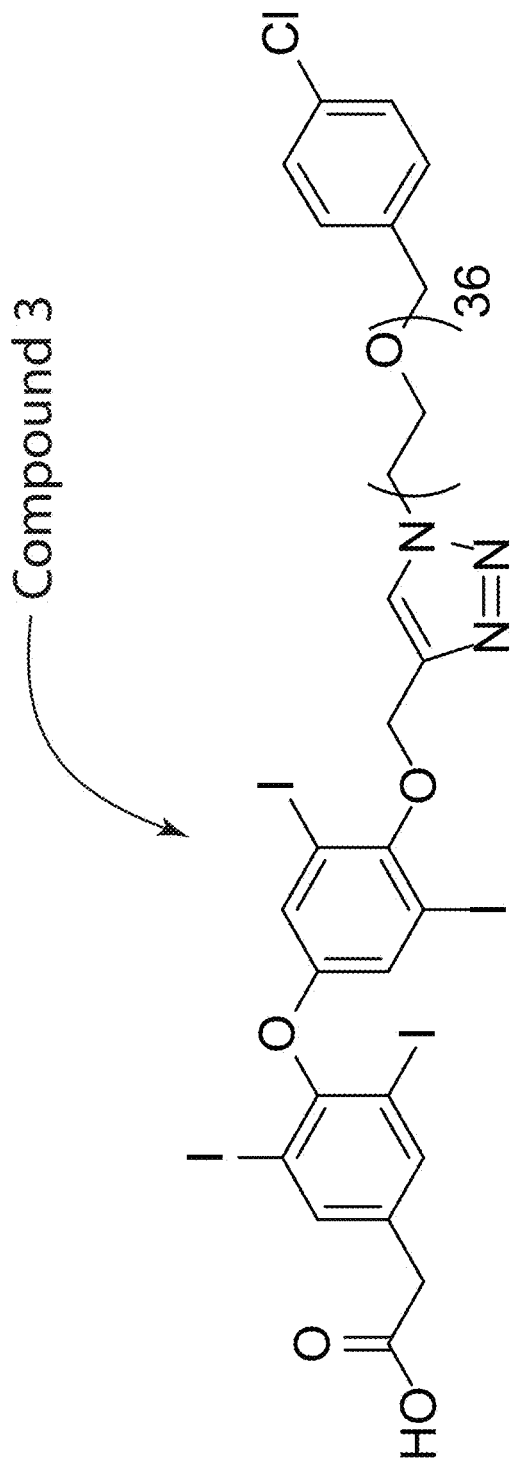
FIG. 5 depicts exemplary Compound 3.

Turning more specifically to exemplary Compounds 2-5, these may be broadly referred to as X-PTAT, wherein the substituent A 120 is now specified as a substituted benzyl group (such as the substituted benzyl group 122 shown in FIG. 3, fluorobenzyl or chlorobenzyl as shown in FIGS. 4 and 5, respectively, or a different substituted benzyl group such as that shown in FIG. 6) and referred to as X, P is the polymer or polyethylene glycol, and TAT refers to triazole tetrac. Further, they may be referred to as X-PMTAT, wherein the substituent A 120 is now specified as the substituted benzyl group and referred to as X, P is the polymer or polyethylene glycol, and MTAT refers to monotriazole tetrac. Still further, they may be referred to as X-PMT, wherein the substituent A is now specified as the substituted benzyl group and referred to as X, P is the polymer or polyethylene glycol, and MT again refers to monotriazole tetrac.

Figure 7:
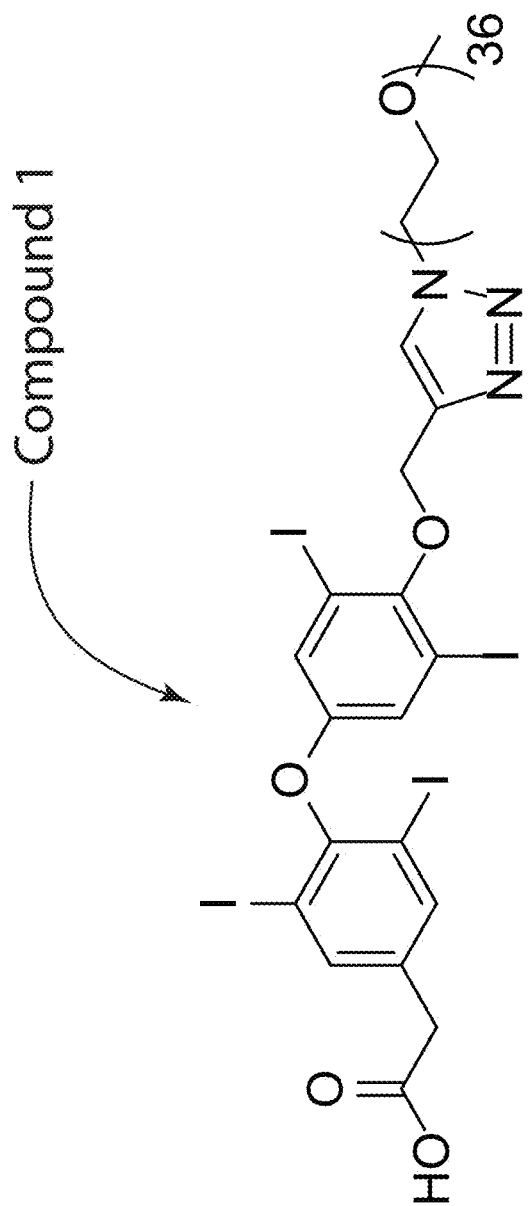
FIG. 7 depicts exemplary Compound 1.

These designations are in contrast to the compound depicted in FIG. 7, namely Compound 1. This Compound 1 comprises a specific embodiment of a thyrointegrin antagonist conjugated to a polymer such as is described in U.S. patent application Ser. No. 15/616,637 now U.S. Pat. No. 10,201,616 and U.S. patent application Ser. No. 16/223,176. This compound may be referred to as Compound 1 and also as PTAT, PMT, or PMTAT. As discussed above, these designations indicate the inclusion of polymer conjugated to (mono)triazole tetrac, in this case conjugated only to a methyl group, and without conjugation to a functional group such as substituent A 120 described above (or the more specific examples such as the substituted benzyl group).

Turning back to embodiments of the currently disclosed invention, such as those shown in FIGS. 4 and 5, the variable R9 may be substituted for a halogen. For example, R9 may be substituted for a fluorine molecule as shown in FIG. 4. This structure is referred to as Compound 2 and may also be referred to as fluorobenzyl conjugated to triazole tetrac by polyethylene glycol or alternatively as fb-PTAT, fb-PMTAT, or fb-PMT. In another embodiment, R9 may be substituted for a chlorine molecule as shown in FIG. 5. This structure is referred to as Compound 3 and may also be referred to as chlorobenzyl conjugated to triazole tetrac by polyethylene glycol or alternatively as cb-PTAT, cb-PMTAT, or cb-PMT.

In still further embodiments such as that shown in FIG. 6, the variables R1 and R2 may be substituted. For example, R1 and R2 may be substituted for tert-butyl groups. This structure is referred to as Compound 4 and may also be referred to as di-tbutylbenzyl conjugated to triazole tetrac by polyethylene glycol or alternatively as Dtbb-PTAT, Dtbb-PMTAT, or Dtbb-PMT.

Figure 8:
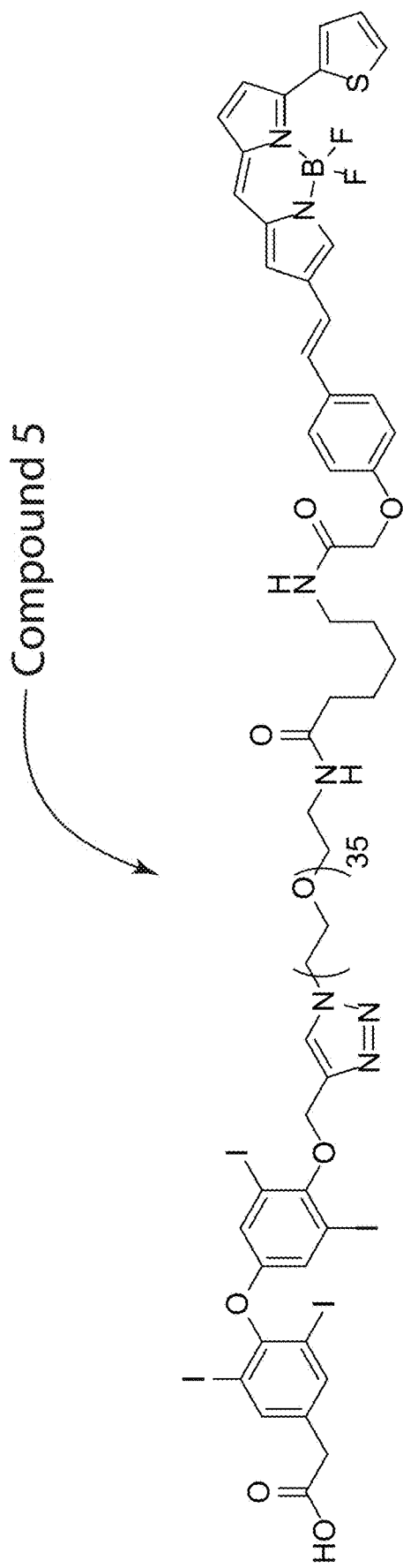
FIG. 8 depicts exemplary Compound 5.

Additional embodiments may include a dye, marker, label, or the like, for example, for imaging purposes. The dye, marker, or label may be on the substituted benzyl in some embodiments. For example, FIG. 8 depicts a labeled polymer conjugated monotetrac (PMT) derivative referred to as Compound 5. In this example, substituent A 120 comprises a dye marker, for example BODIPY. Compound 5 may also be referred to as BODIPY-PMT.

As discussed above, additional embodiments of the substituent A 120 are also contemplated. For example, as shown in FIGS. 9A, 9B, and 9C, additional ring structures are disclosed for substituent A 120. In these examples, R8 may be equal to H, Me, Et, and the like. R1-R7 may be independently selected from H, Me, Et, iPr, nPr, nBu, iBu, secBu, tBu, $C_5$-$C_{12}$ n-alkyl, cyclopentyl, cyclohexyl, phenyl, F, Cl, Br, I, CN, $CF_3$, $OCF_3$, $CHF_2$, $OCHF_2$, $SO_2Me$, $NO_2$, —O-Alkyl, —O-Aryl, —$CH_2$—O-Alkyl, —$CH_2$—O-Aryl, esters, amides, and the like. Ester substitution may be selected from the following:

-continued

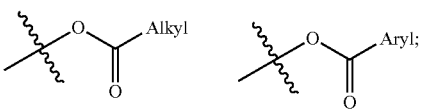

and amide substitution may be selected from the following:

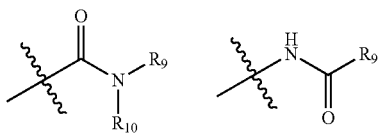

wherein R9 and R10 are independently selected from H, Alkyl, Aryl, and the like.

Figure 10B:
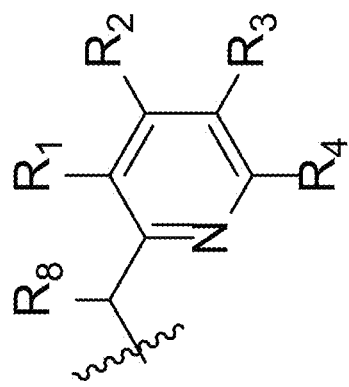
FIG. 10B depicts another embodiment of Substitution A from FIG. 1 in accordance with an embodiment of the invention.
Figure 10C:
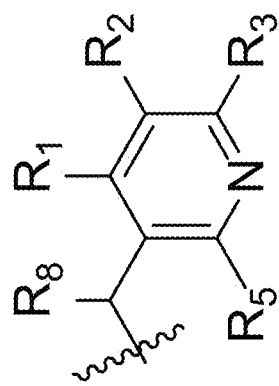
FIG. 10C depicts another embodiment of Substitution A from FIG. 1 in accordance with an embodiment of the invention.
Figure 10A:
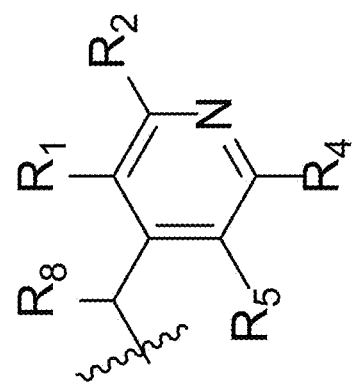
FIG. 10A depicts another embodiment of Substitution A from FIG. 1 in accordance with an embodiment of the invention.

Still further, as discussed above, additional embodiments of the substituent A 120 may include heterobenzyls such as those shown in FIGS. 10A through 10C. Moreover, 5-membered ring heteroaryls, fused heteroaryls, quinolines, indoles, and the like may also be used. R1-R5 and R8 may be substituted as described above.

Figure 11:
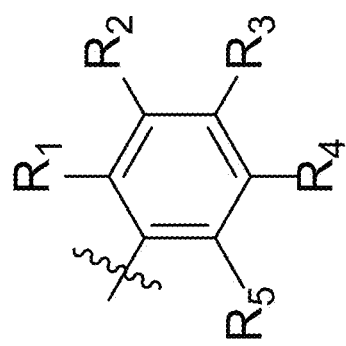
FIG. 11 depicts another embodiment of Substitution A from FIG. 1 in accordance with an embodiment of the invention.

Phenoxy groups such as that shown in FIG. 11 may also be used as embodiments of substituent A 120. Again, R1-R5 may be substituted as described above.

Figure 12B:
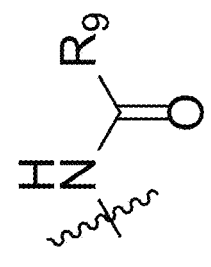
FIG. 12B depicts another embodiment of Substitution A from FIG. 1 in accordance with an embodiment of the invention.
Figure 12A:
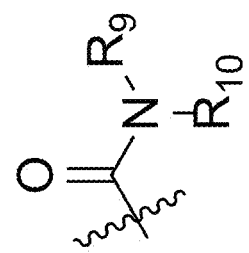
FIG. 12A depicts another embodiment of Substitution A from FIG. 1 in accordance with an embodiment of the invention.
Figure 13D:
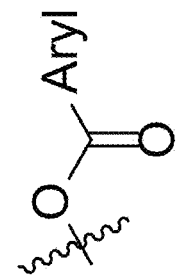
FIG. 13D depicts another embodiment of Substitution A from FIG. 1 in accordance with an embodiment of the invention.
Figure 13B:
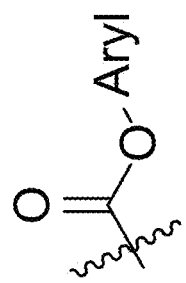
FIG. 13B depicts another embodiment of Substitution A from FIG. 1 in accordance with an embodiment of the invention.
Figure 13C:
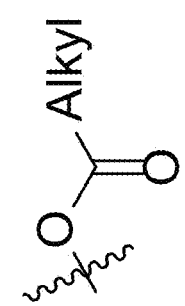
FIG. 13C depicts another embodiment of Substitution A from FIG. 1 in accordance with an embodiment of the invention.
Figure 13A:
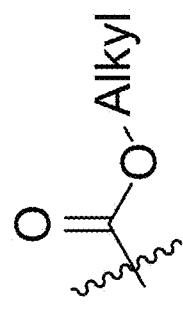
FIG. 13A depicts another embodiment of Substitution A from FIG. 1 in accordance with an embodiment of the invention.

In additional embodiments, substituent A 120 may comprise an amide such as those depicted in FIGS. 12A and 12B. R9 and R10 may be substituted.

Esters may also be used as substituent A 120 in embodiments. For example, esters such as those depicted in FIGS. 13A-13D may be used.

As described above, in embodiments varying types of polymer may be used, as well as various molecular weights of polymer. In embodiments, monodisperse polymers may be used to increase ease of analysis and scalability relative to polydisperse polymers. Further, as shown in exemplary Compounds 2-4, embodiments may include a relatively large polymer such as PEG36. Large monodisperse polymers such as monodisperse PEG36 may contribute to solubility and analysis of the exemplary compounds. Further, such large monodisperse polymers may increase scalability by yielding a relatively large solid product amenable to purification. Thus, embodiments comprising PEG36 conjugated to mono triazole tetrac may have simplified synthesis and scalability when compared with other embodiments. In some embodiments, the polymer may have a molecular weight of approximately 4,000 Daltons, for example, 4,000±10%. Still further, these large monodisperse polymers may contribute to the increased active transport of the compound, for example, by making the thyrointegrin antagonist (transporter target) more accessible.

Synthesis of the specific exemplary compounds described herein (Compounds 1-5) is demonstrated below. The synthesis description is provided only as examples and is not intended to limit the disclosure. These example uses propargylated tetrac (PGT). Preparation of PGT or a derivative thereof from tetrac is described in U.S. patent application Ser. No. 15/616,637 now U.S. Pat. No. 10,201,616.

Example 1: Synthesis of Compound 1 (PMT)

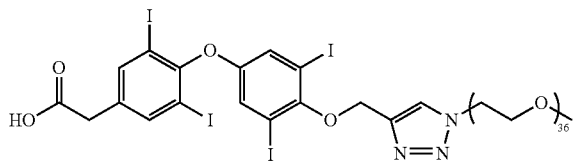

Figure 14:
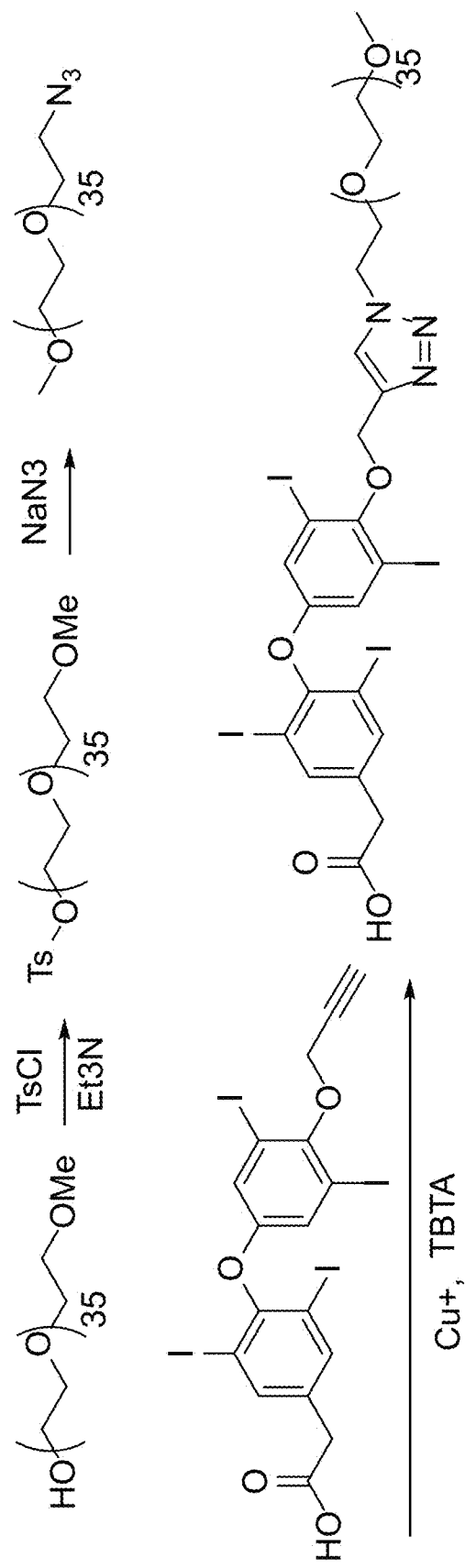
FIG. 14 depicts an exemplary synthetic pathway for Compound 1 in accordance with an embodiment of the invention.

Compound 1 and similar compounds/compositions were described in U.S. patent application Ser. No. 15/616,637 now U.S. Pat. No. 10,201,616 (see, for example, FIGS. 7c and 8 (compound 730)), and may be prepared as described therein. However, Applicant also provides the following sample method:

FIG. 14 depicts an overview of a synthetic pathway for Compound 1. The individual steps of the scheme of synthesis of Compound 1 will be described in more detail below.

Step 1: 1 g (0.625 mmol) of monodisperse MeoPEG$_{36}$OH (PurePEG, San Diego Calif.) and 0.285 ml (4 eq.) TEA were dissolved in 10 ml DCM. 238 mg (2 eq.) of TosCl was added portionwise over 10 min with stirring, and stirred overnight. 10 mL of DCM was added, and the mixture washed 2× with 5 mL of saturated ammonium chloride, 2× with 5 mL of saturated sodium bicarbonate, 1× with 5 mL of saturated brine, and the solvent was stripped under vacuum. The solid was dissolved in 10 mL hot THF add an equally volume of hot hexane was added. The liquid was decanted from a small amount of insoluble material and the product was allowed to precipitate at −20 C overnight. The product was filtered, washed with hexane, and dried under vacuum yielding 995 mg (90%) of product.

Step 2: 990 mg MeOPEG$_{36}$OTs (0.565 mM) was dissolved in 5 ml CH$_3$CN. 110 mg (3 eq) of sodium azide was added, and the mixture was heated at 70 C overnight with stirring. The reaction was then cooled and most of the acetonitrile was removed under reduced pressure, and the residue was partitioned between 10 mL each of DCM and water. The aqueous layer was extracted 3× with 5 mL portions of DCM, and the combined organic layers were washed with 5 ml each of water and saturated brine. The solvent was stripped under reduced pressure, and the material was precipitated from THF/hexane in a procedure similar to the previous step yielding 832 mg (89%) of product.

Step 3: 830 mg (505 mmol) MeO-PEG$_{36}$-N$_3$, 474 mg (4-{3,5-Diiodo-4-[(2-prop-2-yn-1-yl)oxy]-phenoxy]-3,5-diiodophenyl)acetic acid (1.2 eq), and 13.7 mg TBTA (5%) were dissolved in 20 ml THF. Dissolve 12.6 mg (0.1 eq) copper sulfate hydrate and 60 mg (0.6 eq) sodium ascorbate in 5 ml of water and add to the THF solution. Stir under N$_2$ for 16 h, then decant the liquid from the small amount of blue solids on the bottom of the flask. Strip the THF from the solution under reduced pressure, add 10 ml of water, acidify to pH 3 with dilute HCl, and extract 3×40 mL with DCM. Wash the combined organic layers 3× with 5 mL of saturated EDTA solution, then 5 mL of saturated brine. Strip the DCM under reduced pressure, and dissolve the remainder in 20 ml of warm THF. Add 20 ml of hot hexane, and warm until almost everything is dissolved. Cool to room temperature, then decant the liquid from the small amount of solid and oil on the bottom of the vial. Allow the mixture to precipitate at −20 C overnight, filter off the solids, and wash with cold hexane. Dry the remaining white solid under reduced pressure, 685 mg. Dissolve in 6.5 mL H2O with 2.5 mL of 1M NaOH and 1 mL of saturated sodium chloride. Wash 2×25 mL with 3:2 hexane:DCM. Add 1 ml more of saturated NaCl and wash with another 2×25 mL of 3:2 Hexane:DCM. The aqueous layer was acidified to pH 2.0 with dilute HCl and extracted 3×25 mL with DCM. The combined organic layers were washed with saturated sodium chloride, and the solvent was removed under reduced pressure. The residue was precipitated from 20 mL of THF and 20 mL of hexane, yielding 491 mg of product. $^1$H NMR (600 MHz, DMSO D$_6$) d (PPM): 8.258 (s, 1H), 7.850 (s, 2H), 7.195 (s, 2H), 5.015 (s, 2H), 4.581 (br. s, 2H), 3.851 (br. s, 2H), 3.6-3.3 (m, 144H), 3.239 (S, 3H). MS m/z 2452.2 (M+Na), 1215.4 (M+2H), 810.2 (M+3H), 608.2 (M+4H).

Example 2: Synthesis of Compound 2 (fb-PMT)

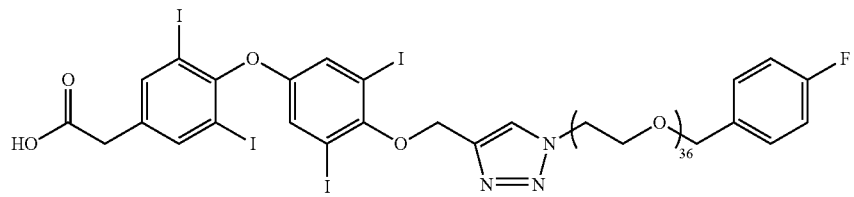

Figure 15:
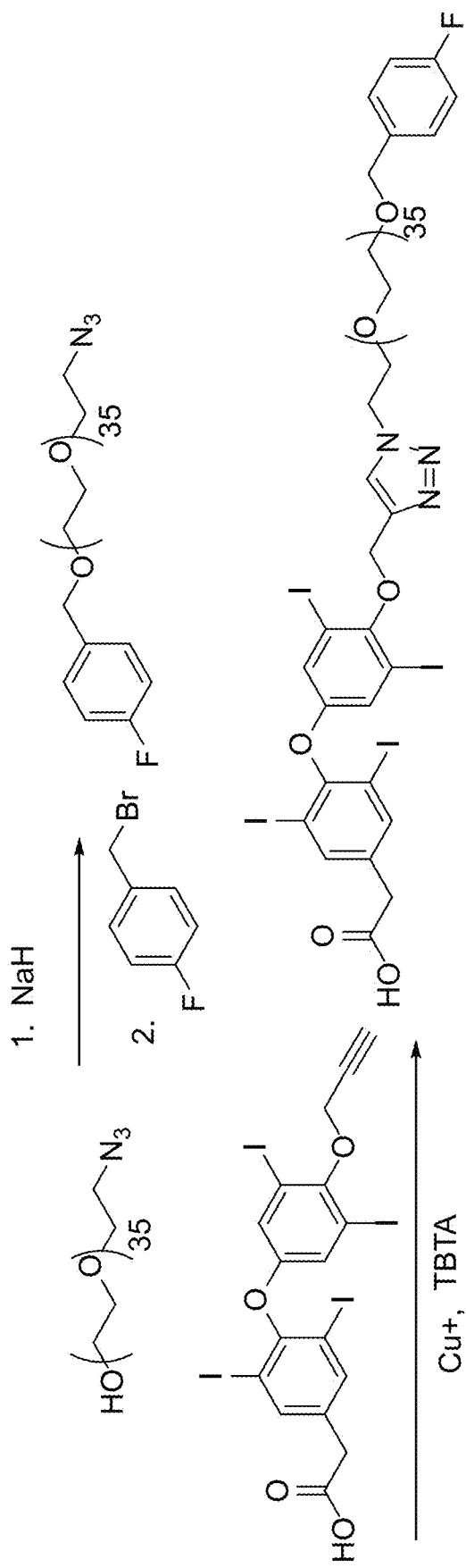
FIG. 15 depicts an exemplary synthetic pathway for exemplary Compound 2 in accordance with an embodiment of the invention.

FIG. 15 depicts an overview of a synthetic pathway for Compound 2. The individual steps of the scheme of synthesis of Compound 2 will be described in more detail below.

Step 1: 250 mg HO-PEG36-azide (0.155 mmol, PurePEG, San Diego Calif.) was added to 19 mg 60% NaH (3 eq) in 5 ml of THF. The mixture was stirred for 30 min, then 58 uL of 4-(fluorobenzyl)bromide (Aldrich) (3 eq.) in 2 mL of THF was added dropwise. The mixture was stirred 18 h, then 2 mL of saturated sodium bicarb was added. The THF was stripped off under vacuum, 10 mL of saturated brine was added, the mixture was extracted 3× with 15 ml portions of DCM. The combined organic layers were washed with 5 ml of saturated brine and the solvent was stripped off under vacuum. The material was then chromatographed on 24 g of silica with 0-10% MeOH in DCM yielding 170 mg of material, >99% pure by HPLC.

Step 2: 170 mg (0.147 mmol) of 4-fluorobenzylPEGazide, 138 mg (0.176 mmol) (4-{3,5-Diiodo-4-[(2-prop-2-yn-1-yl)oxy]-phenoxy]-3,5-diiodophenyl)acetic acid, and 3 mg of TBTA were dissolved in 8 mL of THF. Add 3 mg CuSO4 hydrate and 23 mg Na ascorbate in 2 mL water and stir 4 h under N2. Strip off the THF under vacuum, then add 5 ml saturated brine and 0.5 ml of 1M HCl. Extract 3×10 mL with DCM, wash 3×5 mL with saturated EDTA, once with 5 mL of saturated brine, and strip the solvent under vacuum. Dissolve the residue in 10 mL of warm THF, then add hexane until it just starts to turn cloudy. Allow the product to precipitate overnight at −20 C. Filter off the solid to get 180 mg of product. $^1$H NMR (600 MHz, DMSO D$_6$) d (PPM): 8.246 (s, 1H), 7.879 (s, 2H), 7.361 (dd, 2H), 7.167 (m, 4H), 5.013 (s, 2H), 4.575 (m, 2H), 4.466 (s, 2H), 3.847 (m, 2H), 3.640 (s, 2H), 3.55-3.4 (m, 144H). MS m/z 1262.8 (M+2H), 842.5 (M+3H), 632.2 (M+4H). The product can be further purified by chromatography on normal phase silica gel.

Example 3: Synthesis of Compound 3 (cb-PMT)

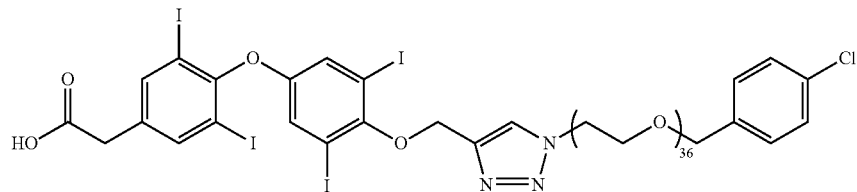

Figure 16:
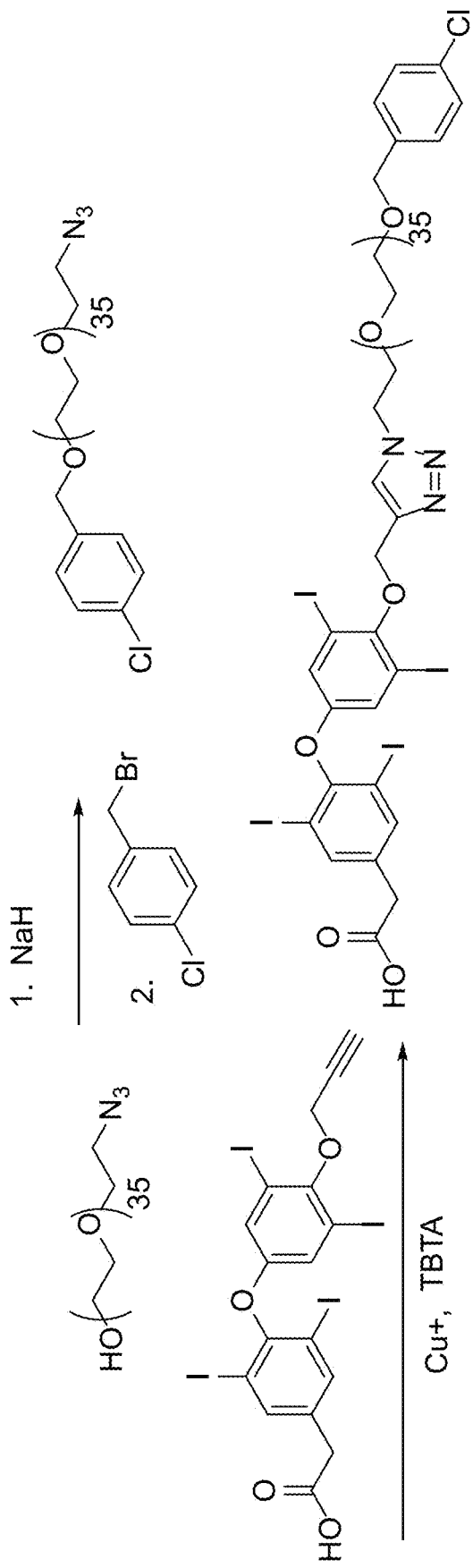
FIG. 16 depicts an exemplary synthetic pathway for exemplary Compound 3 in accordance with an embodiment of the invention.

FIG. 16 depicts an overview of a synthetic pathway for Compound 3. The individual steps of the scheme of synthesis of Compound 3 will be described in more detail below.

Step 1: 250 mg PEGazide (0.155 mmol) added to 19 mg 60% NaH (3 eq) in 5 ml THF. Stir 30 min, then add 95.5 mg 4-chlorobenzylbromide (Aldrich) (3 eq.) in THF dropwise. Stir 18 h, add saturated sodium bicarbonate solution, strip off the THF under vacuum, add 10 mL sat brine, extract 3× with 15 ml portions of DCM, wash the combined organic layers with saturated brine, and strip off the solvent under vacuum. Chromatograph with 0-10% MeOH in DCM on silica gel. 190 mg.

Step 2: Dissolve 190 mg (0.111 mmol) chlorobenzylPEGazide, 131 mg (4-{3,5-Diiodo-4-[(2-prop-2-yn-1-yl)oxy]-phenoxy]-3,5-diiodophenyl)acetic acid (1.5 eq), and 3 mg TBTA in 8 mL THF. Add 3 mg CuSO4 hydrate and 23 mg Na ascorbate in 2 mL water, and stir 4 h. Strip off the THF under vacuum, then add 5 of saturated brine and 0.5 ml of 1M HCl. Extract 3× with DCM, wash 3× with saturated EDTA, once with brine, and strip the solvent under vacuum. Dissolve in 10 mL of warm THF, then add hexane until it just starts to turn cloudy. Precipitate the material in −20 freezer, 180 mg product. $^1$H NMR (800 MHz, D$_2$O) d (PPM): 8.369 (s, 0.3H), 8.147 (s, 0.7H) 7.758 (s, 2H), 7.261 (m, 6H), 4.993 (s, 2H), 4.541 (m, 2H), 4.451 (s, 2H), 3.849 (m, 2H), 3.640 (s, 2H), 3.65-3.54 (m, 142H), 3.346 (s, 2H). MS m/z 1281.2 (M+2H), 854.9 (M+3H), 641.4 (M+4H). The product can be further purified by chromatography on normal phase silica gel.

Example 4: Synthesis of Compound 4 (Dtbb-PMT)

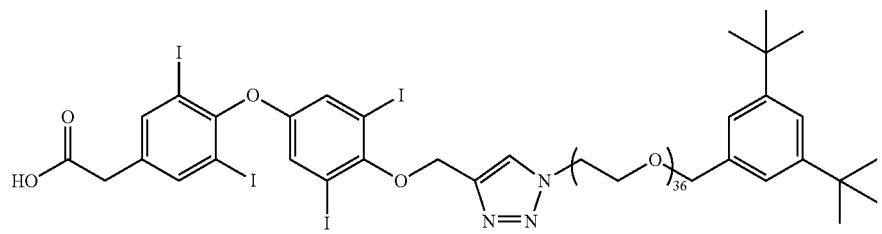

Figure 17:
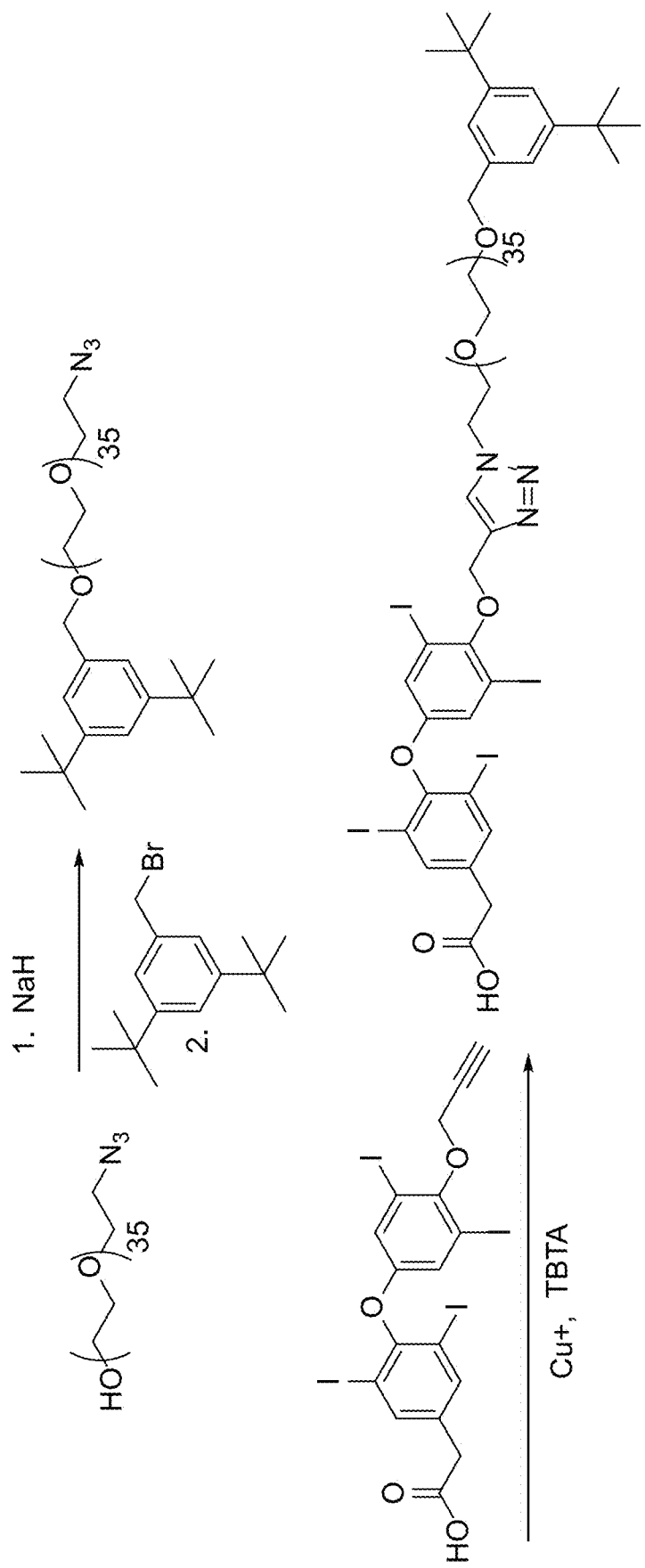
FIG. 17 depicts an exemplary synthetic pathway for exemplary Compound 4 in accordance with an embodiment of the invention.

FIG. 17 depicts an overview of a synthetic pathway for Compound 4. The individual steps of the scheme of synthesis of Compound 4 will be described in more detail below.

Step 1: 250 mg HO-PEG36azide (0.155 mmol) was added to 19 mg 60% NaH (3 eq) in 5 ml THF. Stir 30 min, then add 131 mg bromide (Aldrich) (3 eq.) in THF dropwise. Stir 18 h, add saturated sodium bicarbonate, strip off the THF under vacuum, add 10 mL sat brine, extract 3× with 15 ml portions of DCM, wash the combined organic layers with saturated brine, and strip off the solvent under vacuum. Chromatograph with 0-20% MeOH in DCM on silica gel. 270 mg.

Step 2: 270 mg (0.147 mmol) of di-tbutylbenzylPEGazide, 171 mg (4-{3,5-Diiodo-4-[(2-prop-2-yn-1-yl)oxy]-phenoxy]-3,5-diiodophenyl)acetic acid, and 4 mg TBTA were dissolved in 8 mL THF. Add 4 mg CuSO4 hydrate and 34 mg Na ascorbate in 2 mL water, and stir 4 h. Strip off the THF under vacuum, then add 5 ml saturated brine and 0.5 ml of 1M HCl. Extract 3× with DCM, wash 3× with saturated EDTA, once with brine, and strip the solvent under vacuum. Chromatograph with 0-10% MeOH in DCM on silica gel. 310 mg. $^1$H NMR (600 MHz, DMSO D$_6$, d (PPM): 8.248 (s, 1H), 7.842 (s, 2H), 7.300 (s, 1H), 7.188 (s, 2H), 7.130 (s, 2H), 5.007 (s, 2H), 4.564 (m, 2H), 4.455 (s, 2H), 3.843 (m, 2H), 3.6-3.3 (m, 144H), 1.274 (s, 18H). MS m/z 1309.3 (M+2H), 873.4 (M+3H), 655.8 (M+4H).

Example 5: Synthesis of Compound 5 (BODIPY-PMT)

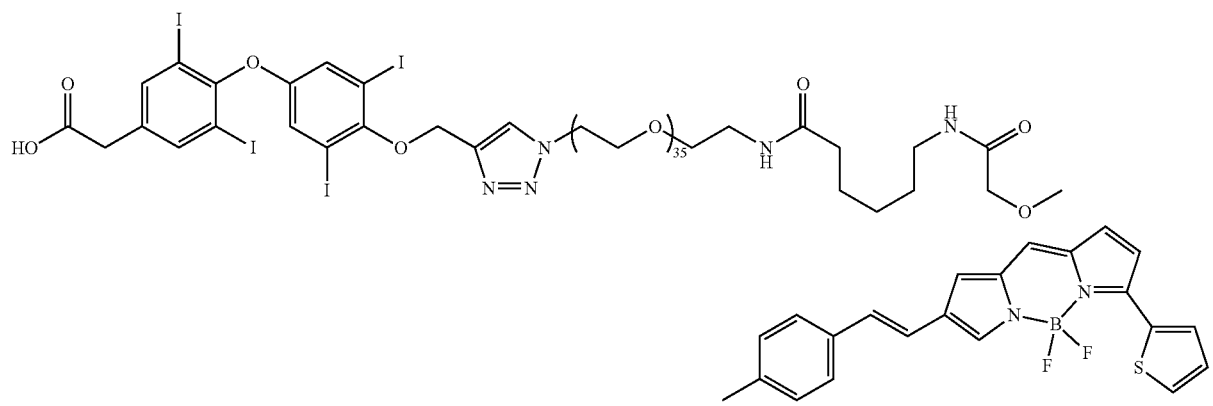

Figure 18:
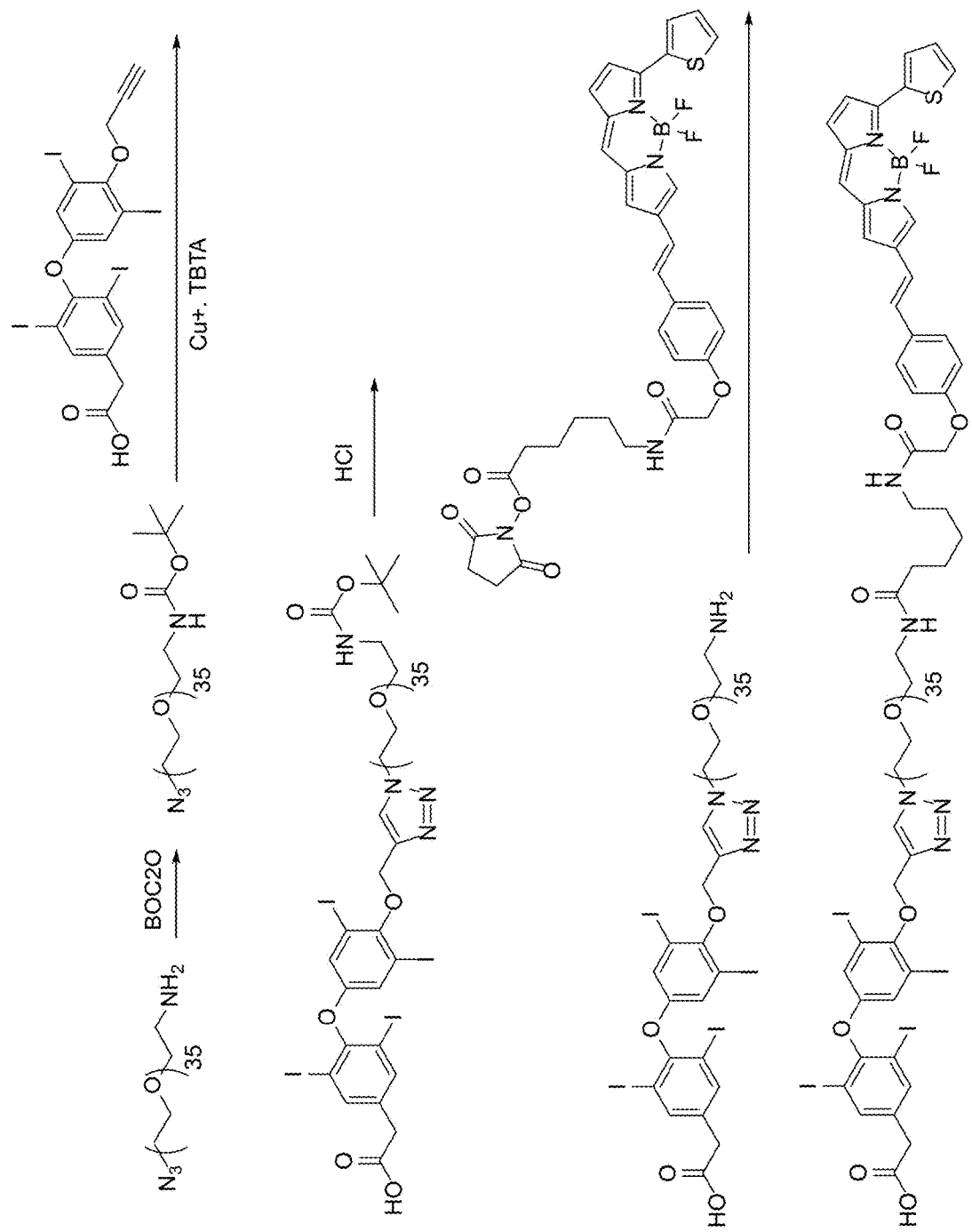
FIG. 18 depicts an exemplary synthetic pathway for exemplary Compound 5 in accordance with an embodiment of the invention.

FIG. 18 depicts an overview of a synthetic pathway for Compound 5. The individual steps of the scheme of synthesis of Compound 5 will be described in more detail below.

Step 1: 250 mg of NH2-PEG36-N3 were treated with 1.5 equivalents of BOC anhydride and 3 eq of triethyl amine in 5 mL of DCM. After stirring for 18 h at room temperature the mixture was diluted with 20 ml of DCM and washed with 0.1M HCl followed by saturated sodium bicarbonate and saturated brine. The solvent was removed under reduced pressure, the residue was dissolved in 5 mL of warm THF, and hexane was added until the mixture started to turn cloudy. The mixture was allowed to stand overnight before filtering and washing with hexane. 240 mg of product was recovered.

Step 2: 235 mg of the step 1 product, 171 mg (4-{3,5-Diiodo-4-[(2-prop-2-yn-1-yl)oxy]-phenoxy]-3,5-diiodophenyl)acetic acid, and 4 mg TBTA were dissolved in 8 mL THF. Add 4 mg CuSO4 hydrate and 34 mg Na ascorbate in 2 mL water, and stir 18 h. Strip off the THF under vacuum, then add 5 ml saturated brine and 0.5 ml of 1M HCl. Extract 3× with DCM, wash 3× with saturated EDTA, once with brine, and strip the solvent under vacuum. The residue was dissolved in 5 mL of warm THF, and hexane was added until the mixture started to turn cloudy. The mixture was allowed to stand overnight before filtering and washing with hexane. 220 mg of product was recovered.

Step 3: 215 mg of step 2 product was dissolved in 2 mL of DCM, and 2 mL of 5M HCl in dioxane was added. The mixture was stirred for 18 h, the solvent was removed under reduced pressure, and the product was used as is for the next step.

Step 4: 18 mg of product from the last step (0.0076 mmol) was dissolved in 1 ml of DCM with 10 uL of triethyl amine. 5 mg of BODIPY 630/650 NHS ester (Thermo Fisher) dissolved in 100 ul of DCM was added. The mixture was shaken for 18 hours, the solvent was removed under reduced pressure, and the residue was chromatographed with on silica gel with 0-20% methanol in DCM. 4.5 mg were recovered. $^1$H NMR (800 MHz, CDCl3) d (PPM): 8.221 (s, 1H), 8.058 (s, 1H), 7.850 (s, 2H), 7.642 (m, 3H), 7.513 (d, 1H), 7.237 (m, 3H) 7.075 (m, 1H), 7.021 (m, 1H), 6.993 (m, 3H), 6.828 (m, 1H), 6.729 (m, 1H), 5.218 (s, 2H), 4.619 (m, 2H), 4.570 (s, 2H), 3.836 (m, 2H), 3.75-3.6 (m, 140H), 3.545 (m, 2H), 3.416 (m, 2H), 3.310 (m, 2H), 2.223 (m, 2H), 1.688 (m, 2H), 1.603 (m, 2H), 1.359 (m, 2H). The product had a retention time of 34.05 minutes on HPLC system 1: Pursuit XRs 3 C18 column, Mobile phase A (water with 0.1% formic acid and 5% acetonitrile) and methanol (B). Flow rate was 1.0 mL/min, gradient was linear from 50% B at 0 min to 95% B at 40-45 min, column temperature 25 C.

Again, other synthetic pathways in addition to those described above may be used to produce the exemplary compounds. Further, additional compounds may be generated using the techniques described above, modified as needed for the respective substitutions.

Methods of Use/Treating

As discussed above, the compounds and compositions described herein have increased uptake across the blood brain barrier and into the brain. Table 1 below demonstrates this increased uptake by showing average brain concentration for each of the exemplary Compounds 1-4. Concentrations are shown as recorded 3 h following administration.

TABLE 1

Brain penetration data

| Compound | Chemical Structure | Average Brain Concentration (ng/g), 3 hour |
|---|---|---|
| m-PMT (1) | 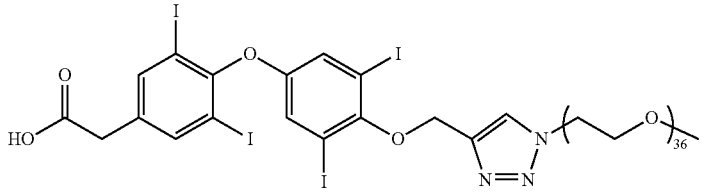 | 55.1 |
| fb-PMT (2) | 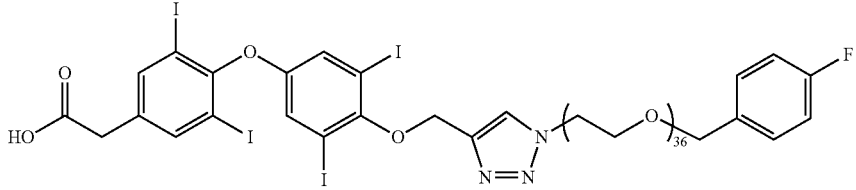 | 228 |
| cb-PMT (3) | 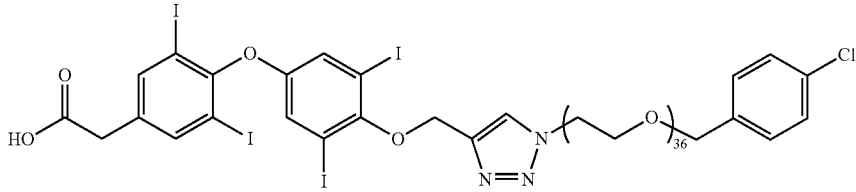 | 266 |
| Dtbb-PMT (4) | 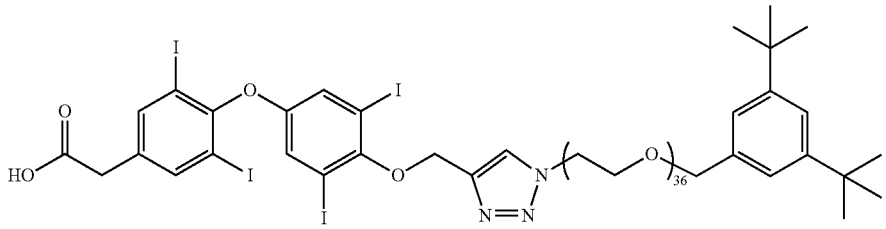 | 922 |
| BG-P-TAT | 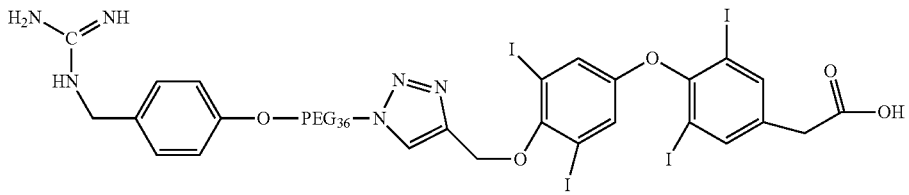 | 0.00 |

The data in Table 1 was generated using the following study: Compositions 1-4 were administered to C57BL/6 mice subcutaneously at 10 mg/Kg. Each group contained 4 mice. The mice were then sacrificed 3 hours post dosing and brain tissues were excised for bio analytical measurement of Compounds 1-4 in the brain. Average concentrations are shown above and each of Compounds 2-4 demonstrated increased uptake compared with Compound 1.

Further, each of Compounds 2-4 also demonstrate increased uptake compared with BG-P-TAT. BG-P-TAT refers to benzyl guanidine conjugated to tetrac via polymer PEG and was described, along with other compounds and compositions comprising αvβ3 integrin thyroid antagonists and targets of the norepinephrine transporter or the catecholamine transporter, in U.S. patent application Ser. No. 15/950,870 now U.S. Pat. No. 10,328,043 and U.S. patent application Ser. No. 16/398,342. The tested embodiment of BG-P-TAT used PEG36. As can be seen, BG-P-TAT does not penetrate the blood brain barrier and there is no detectable level in the brain 3 h after administration. Again, this is in sharp contrast to the currently-disclosed compounds such as exemplary Compounds 2-4 which demonstrate high levels of concentration in the brain.

Increased uptake of the presently disclosed compounds was determined to be due to active transport rather than to passive permeability. For example, as shown in FIG. 20, analysis by passive transport parallel artificial membrane permeability assay (PAMPA) showed low permeability of each of Compounds 1-4. Thus, very little blood brain barrier permeability is achieved without the presence of thyroid binding proteins. Because passive permeability is unaffected and each of Compounds 1-4 have the same transporter recognition element (the thyrointegrin antagonist, triazole tetrac), it would be expected that each of these compounds would be a substrate for thyroid hormone transporters and would likewise have the same or similar uptake into the brain.

However, as demonstrated in Table 1 above, exemplary Compounds 2-4 show a marked and unexpected increase in brain concentration levels over both Compound 1 and BG-P-TAT. Further, as is discussed in more detail below, this unexpected increase in brain uptake and concentration results in similarly unexpected enhanced efficacy in treating conditions requiring blood brain permeability, including, for example, glioblastoma.

Figure 21:
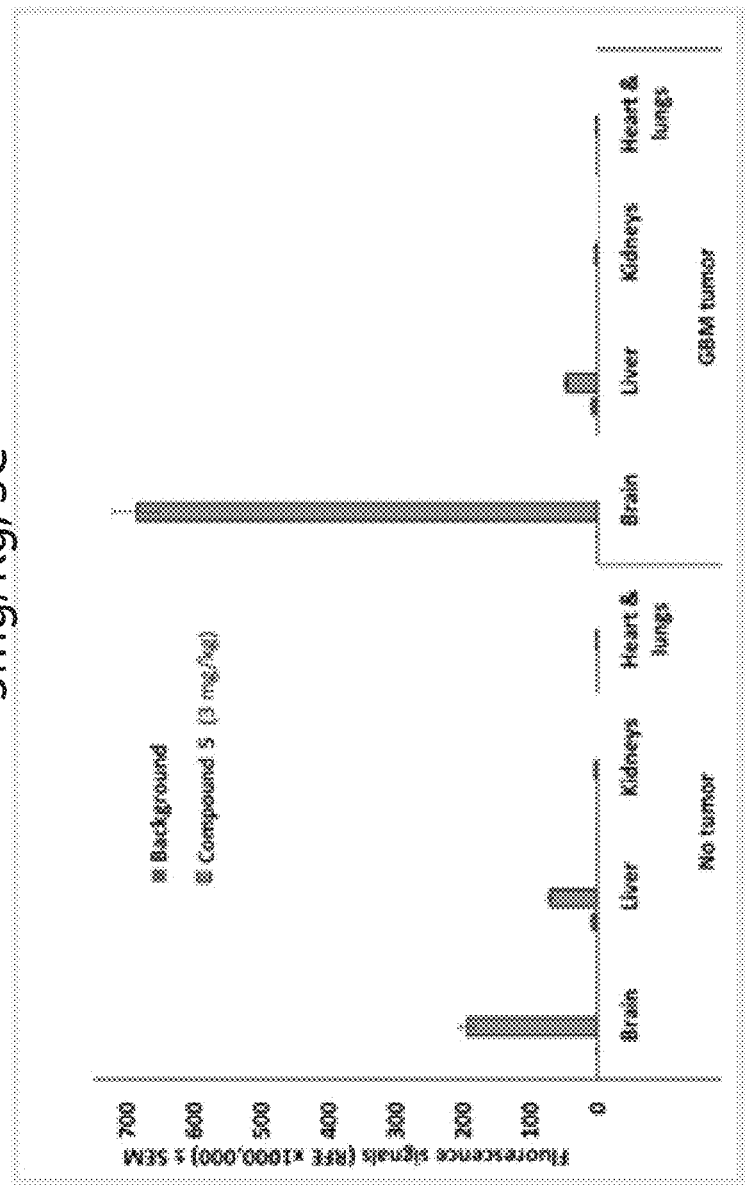
FIG. 21 depicts fluorescence intensity of exemplary Compound 5 in different organs and brain with and without glioblastoma.

Further, as shown in FIG. 21, uptake increases substantially when tumor is present in the brain. As discussed above, this is due, at least in part, to the binding of the compound/composition to the high expression of $\alpha v \beta 3$ by GBM tumors. Further, uptake is predominantly concentrated in the brain to the exclusion of other organs as shown. In the data shown in FIG. 21, uptake was measured using Compound 5 (BODIPY-PMT).

Figure 22:
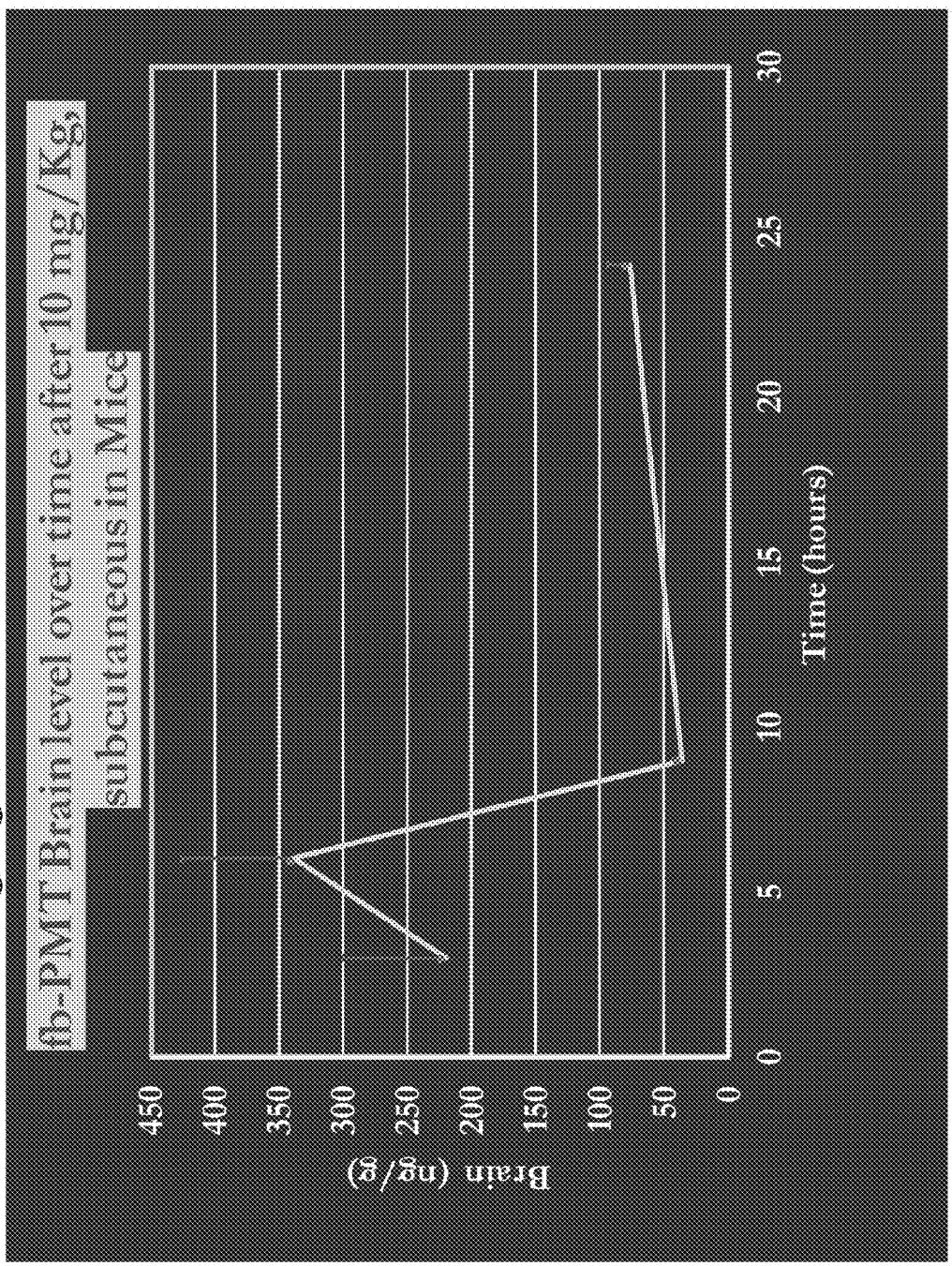
FIG. 22 depicts levels of exemplary Compound 2 present in brain tissue over time following subcutaneous administration in mice.

FIG. 22 also depicts this initial uptake into the brain. As shown, exemplary Compound 2 (fb-PMT) demonstrates uptake and retention over a 24 hour period. Again, a single subcutaneous injection was used in mice. The administered dose was 10 mg/Kg. The brain tissue in this example does not include tumor cells.

Figure 23:
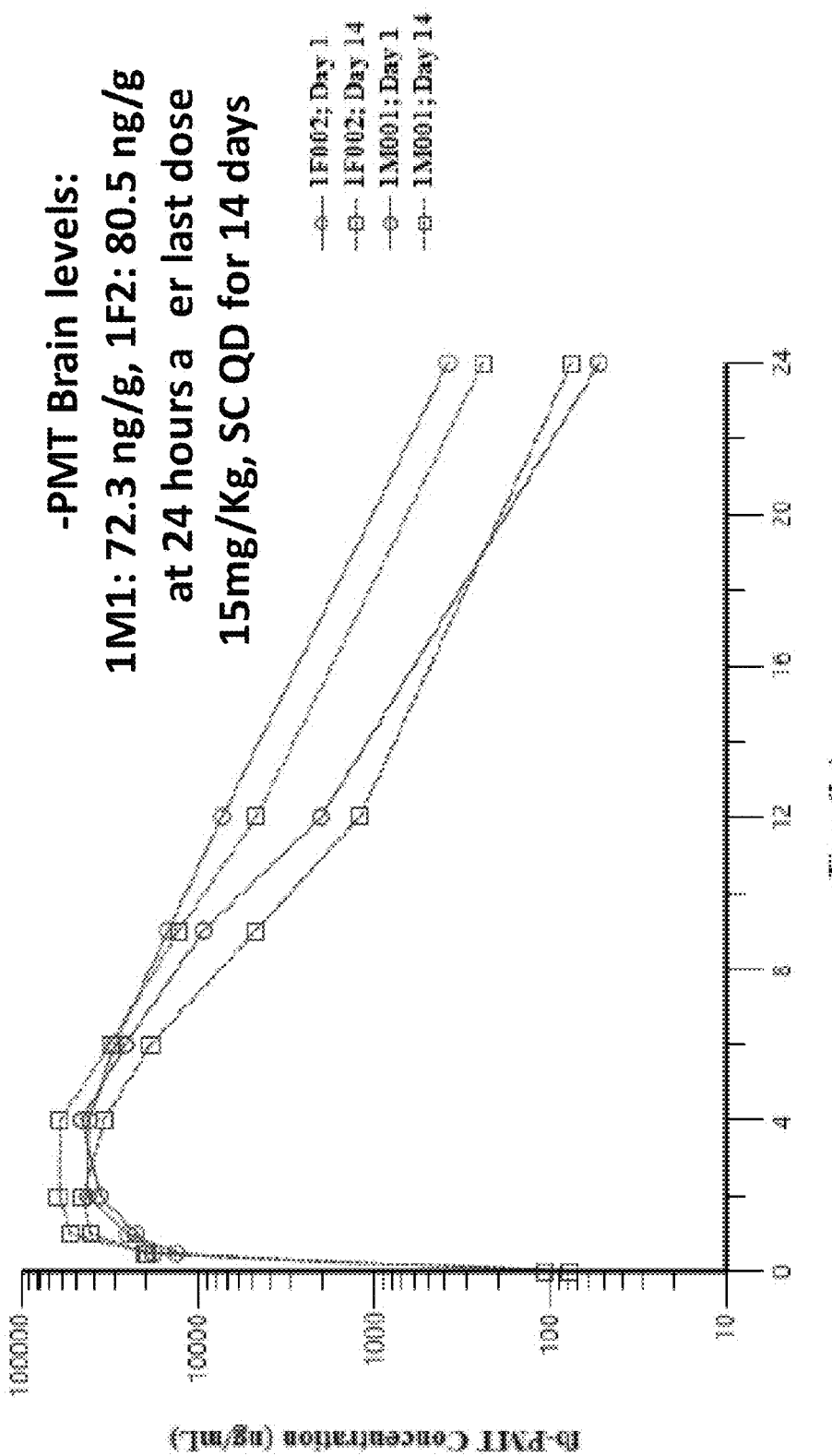
FIG. 23 depicts plasma and brain levels of exemplary Compound 2 over time following subcutaneous administration in cynomolgus monkeys at 15 mg/Kg, s.c. daily for 14 days where brain tissues excised, and blood samples withdrawn for analysis by LC/MS/MS.

Plasma concentrations and brain levels for exemplary Compound 2 (fb-PMT) in cynomolgus monkeys are depicted in FIG. 23. As can be seen, plasma concentration peaks between 1 and 4 hours. Brain levels are also included and Compound 2 is present at 72.3 ng/g and 80.5 ng/g (male and female cynomolgus monkey, respectively) 24 hours after the final dose of a 14 day treatment regimen (15 mg/Kg, SC QD for 14 days) as measured using validated LC/MS/MS method.

Figure 24:
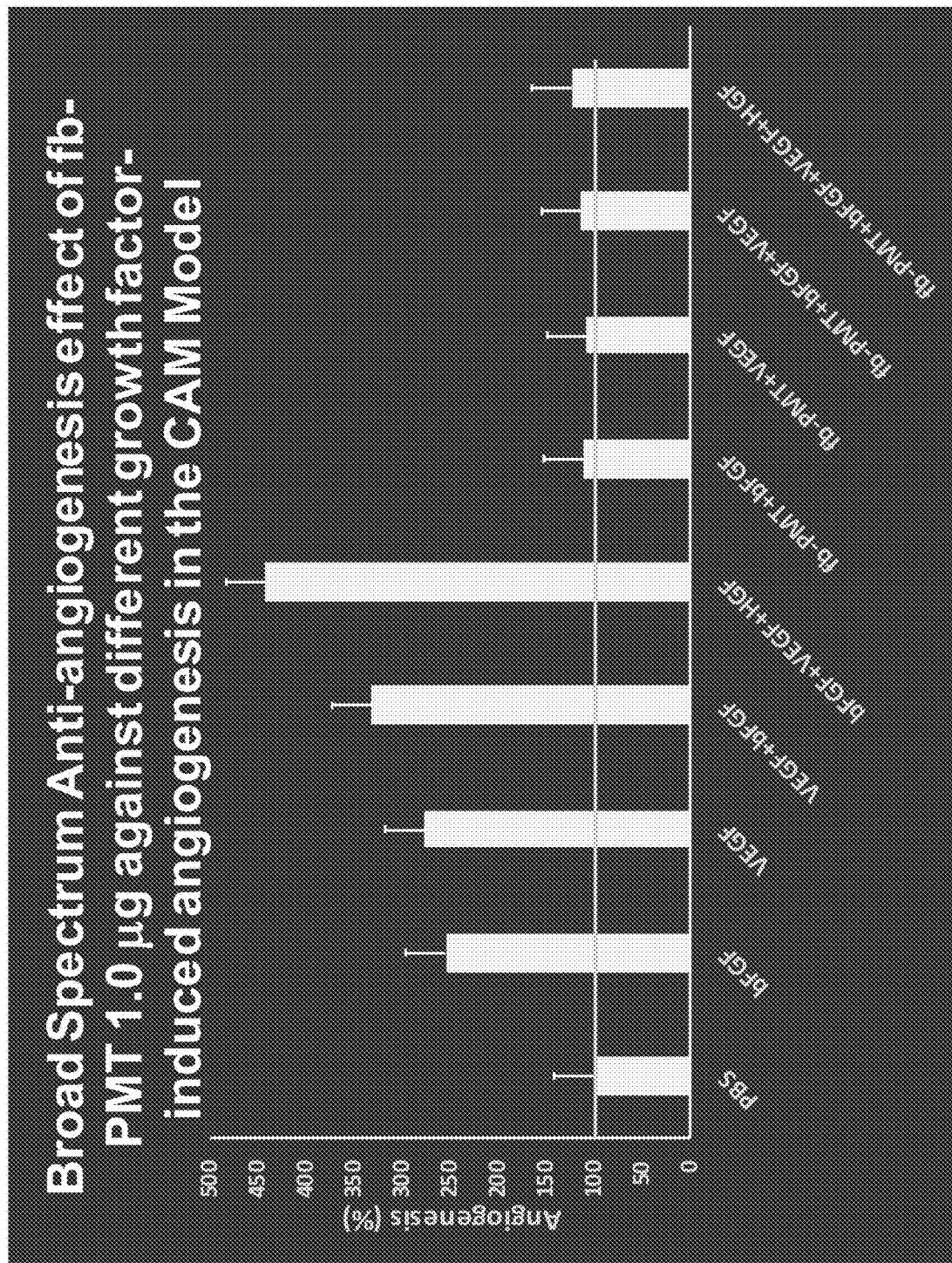
FIG. 24 depicts the antiangiogenic effect of exemplary Compound 2 in the presence of various growth factors.

In addition to good initial uptake, the disclosed compounds also have good anti-angiogenic effect. For example, Exemplary Compound 2 (fb-PMT) demonstrates broad spectrum anti-angiogenic affect against different growth factors as shown in FIG. 24. Specifically, Compound 2 is effective at reducing the percentage of angiogenesis present in CAM Models, when administered in the presence of the following growth factors: bFGF, VEGF, VEGF+bFGF, and bFGF+VEGF+HGF. Each of these growth factors produces a 250% or greater increase in angiogenesis in the CAM Model; however, administration of Compound 2 (fb-PMT) at 1.0 µg drastically reduces this increase to only slightly above baseline.

Figure 25:
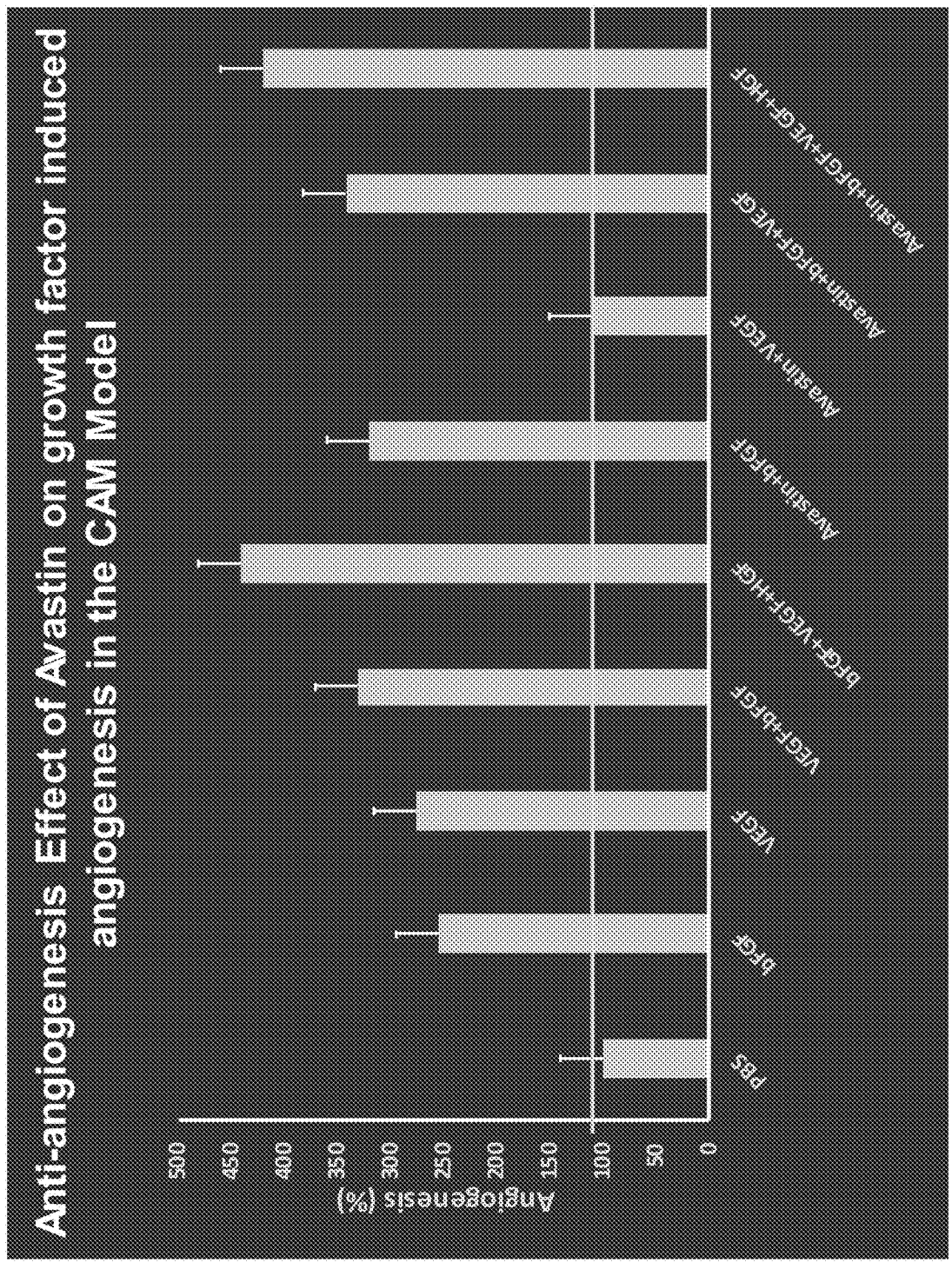
FIG. 25 depicts the antiangiogenic effect only against VEGF, and lack thereof against other growth factors, of known compound Avastin® in the presence of various growth factors.

This broad spectrum anti-angiogenic effect is in contrast to existing therapeutic compounds/compositions such as AVASTIN® (bevacizumab). As shown in FIG. 25, AVASTIN® is primarily effective against VEGF alone, but does not meaningfully reduce the percent of angiogenesis for bFGF or HGF. Further, AVASTIN® does not demonstrate good effect when bFGF or bFGF and HGF are present along with VEGF. Referring back to FIG. 24, exemplary Compound 2 (fb-PMT) demonstrates inhibition of angiogenesis against all three growth factors, both alone and in combination.

Referring again to FIG. 21, exemplary Compound 5 (BODIPY-PMT) shows substantially increased uptake when tumor (GBM) is present in the brain. Further, uptake is predominantly concentrated in the brain to the exclusion of other organs as shown. The study protocol will now be further described.

Athymic female mice were used, with and without GBM in the brain. Mice with GBM received brain orthotopic implantation of U87-luc cells (1 million cells). Compound 5 (BODIPY-PMT) (far-red fluorescence dye) was injected subcutaneously at 3 mg/Kg, s.c. Fluorescence signals were detected (Ex/Em 630 nm/650 nm). The following table shows the full treatment groups:

TABLE 2

Fluorescence Protocol

| Treatment | Mice (No Tumor) | Mice (U87-luc tumor) |
|---|---|---|
| Control | 4 | 4 |
| Compound 5 (BODIPY-PMT) (3 mg/kg, s.c.) | 4 | 4 |
| L-T4* (20 µg/kg, s.c.) | 4 | 4 |
| L-T4 (20 µg/kg) + Compound 5 (3 mg/kg, s.c.) | 4 | 4 |
| Phenytoin* (1 mg/kg, s.c.) | 4 | 4 |
| Phenytoin (1 mg/kg, s.c.) + Compound 5 (3 mg/kg, s.c.) | 4 | 4 |

*L-T4 (thyroxine for hypothyroidism) and Phenytoin (antiseizure) bind to thyroid binding proteins Fluorescence signals of Compound 5 were imaged after 1 h, 2 h, 6 h, and 24 h. After termination, ex vivo fluorescence signals were imaged in the brain and organs. Following the post-termination imaging, luciferase substrate was added to detect tumor luminescent signals in the brain.

Figure 26:
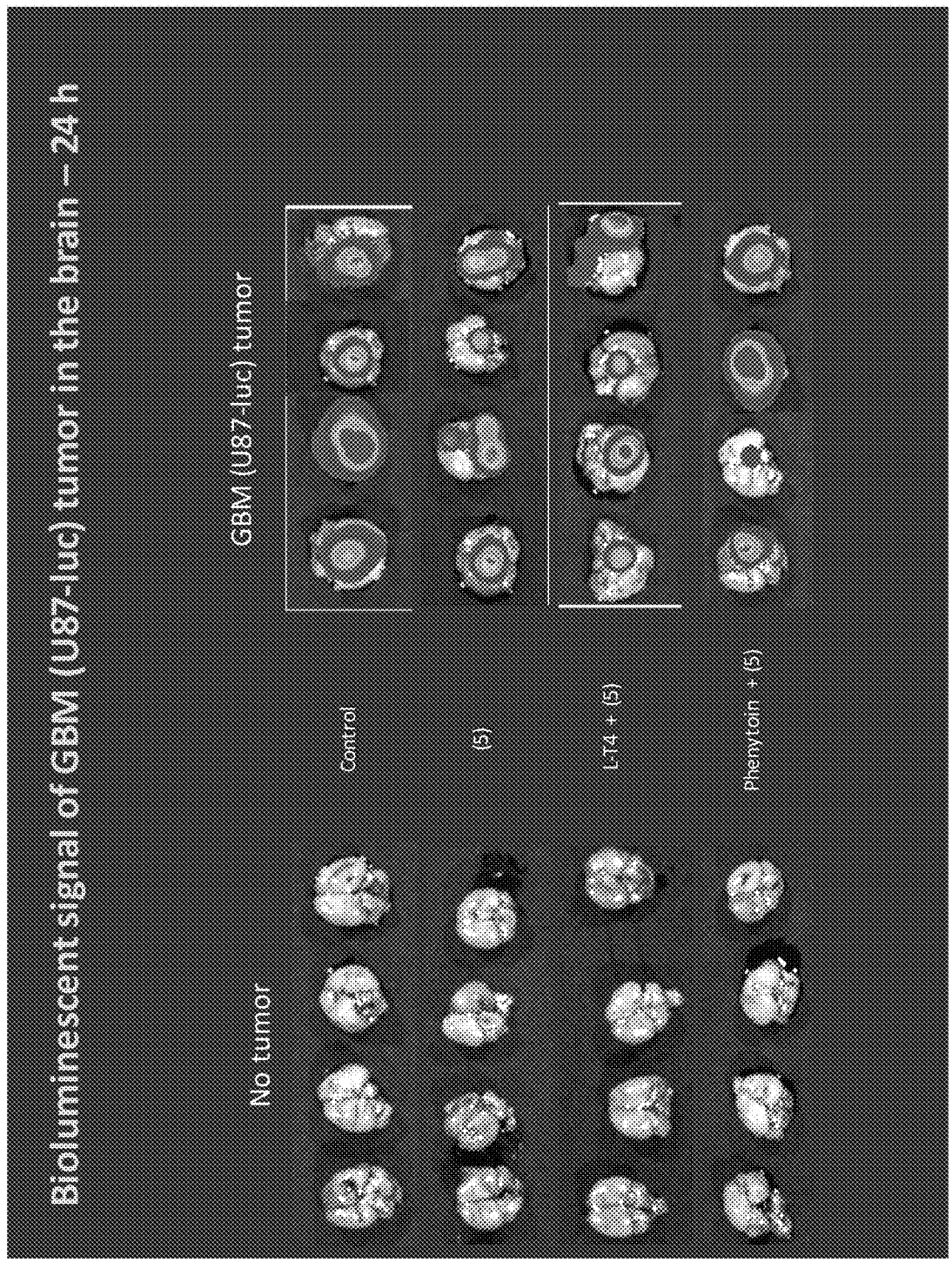
FIG. 26 depicts bioluminescent signals of GBM tumors in the brain.

FIG. 26 shows the bioluminescent signal of GBM (U870-luc) tumor in the brain for the different treatment groups.

Figure 27:
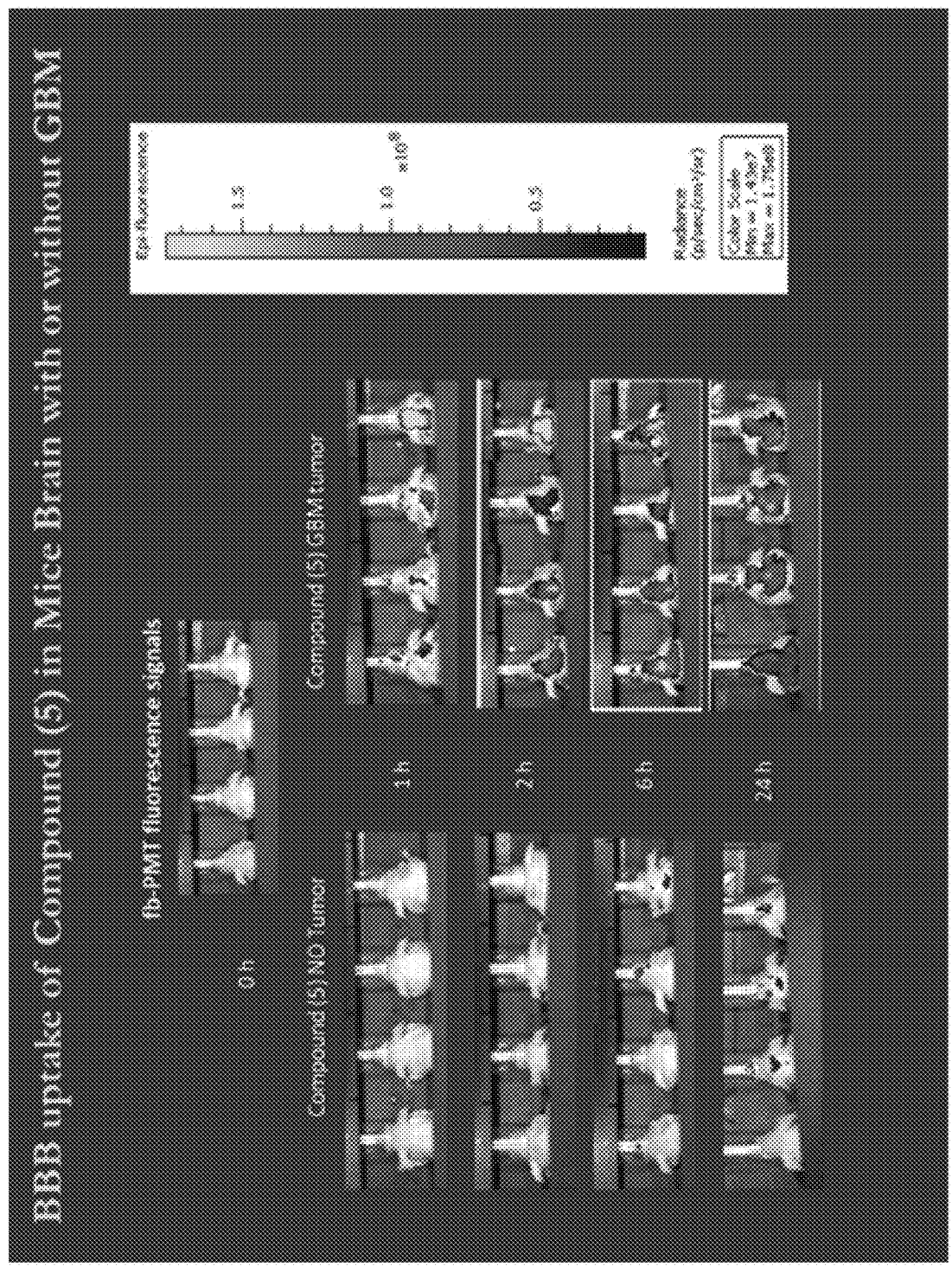
FIG. 27 depicts blood brain barrier uptake of exemplary Compound 5 in the brain in mice with and without GBM tumor.

FIG. 27 shows the presence of Compound 5 (administered at 3 mg/Kg, s.c.) in the brain at the 1 h, 2 h, 6 h, and 24 h intervals. As shown, Compound 5 undergoes uptake into the blood brain barrier and is retained at all intervals. Further, as shown Compound 5 is present at substantially higher levels in the animals with GBM tumors, further evidencing uptake across the blood brain barrier and retention into the tumor site.

Figure 28A:
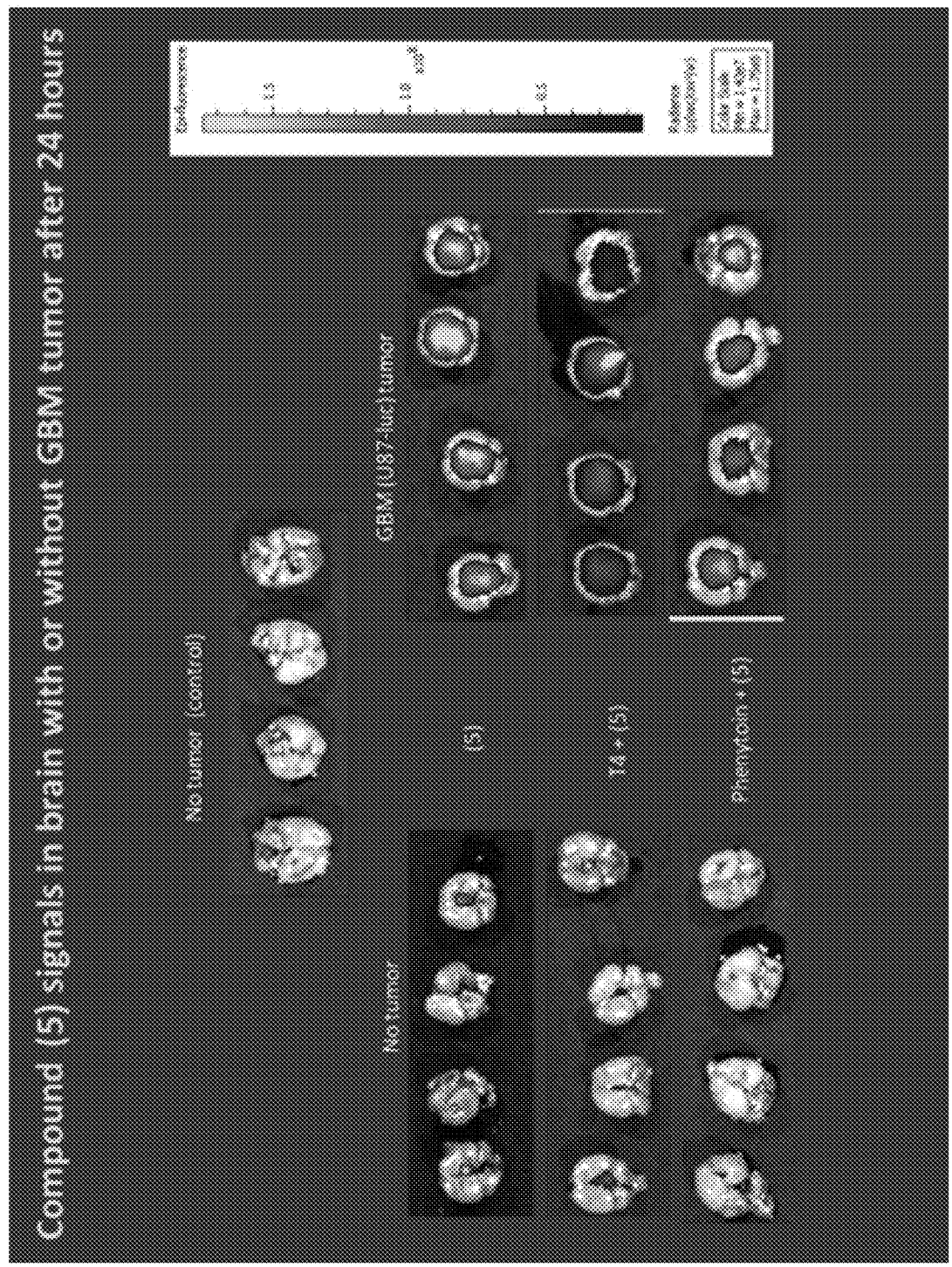
FIG. 28A depicts blood brain barrier uptake of exemplary Compound 5 in the brain in mice with and without GBM tumor, wherein exemplary Compound 5 is administered along with compounds that are used in humans and may potentially compete for uptake and retention.

FIG. 28A shows the blood brain barrier uptake and retention of exemplary Compound 5 (3 mg/Kg) after 24 h. Again, Compound 5 is present at substantially higher levels in the animals with GBM, further evidencing uptake across the blood brain barrier and retention at the tumor site. Compound 5 is present and retained when administered alone and also when administered with other drugs crossing the blood brain barrier, such as thyroid hormone L-T4 and Phenytoin. Thus, the disclosed compounds/compositions demonstrate good uptake and retention within the brain even in the presence of drugs that may compete for uptake/binding.

Figure 28B:
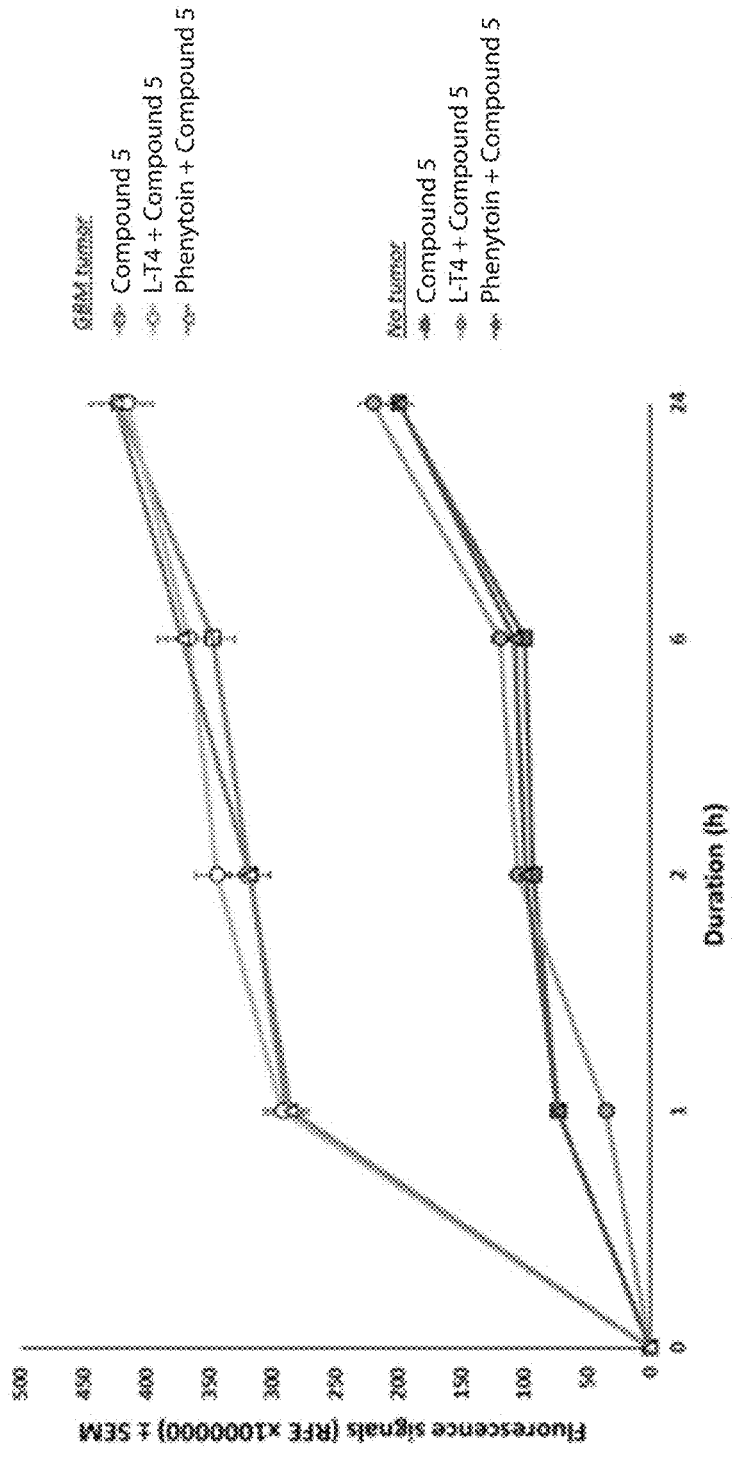
FIG. 28B also depicts blood brain barrier uptake of exemplary Compound 5 in the brain region with and without GBM tumor, wherein exemplary Compound 5 is administered along with compounds that are used in humans that may potentially compete for uptake and retention.

FIG. 28B also shows fluorescence signal intensity of Compound 5 in the brain region with and without GBM tumor. Again, Compound 5 was administered alone and in the presence of L-T4 and Phenytoin. As can be seen, uptake is substantially increased when tumor is present. Further, the increase in uptake is not diminished by the presence of L-T4 nor Phenytoin. Thus, the disclosed compounds demonstrate good uptake into the brain as well as high affinity binding and retention at the tumor site.

Figure 29:
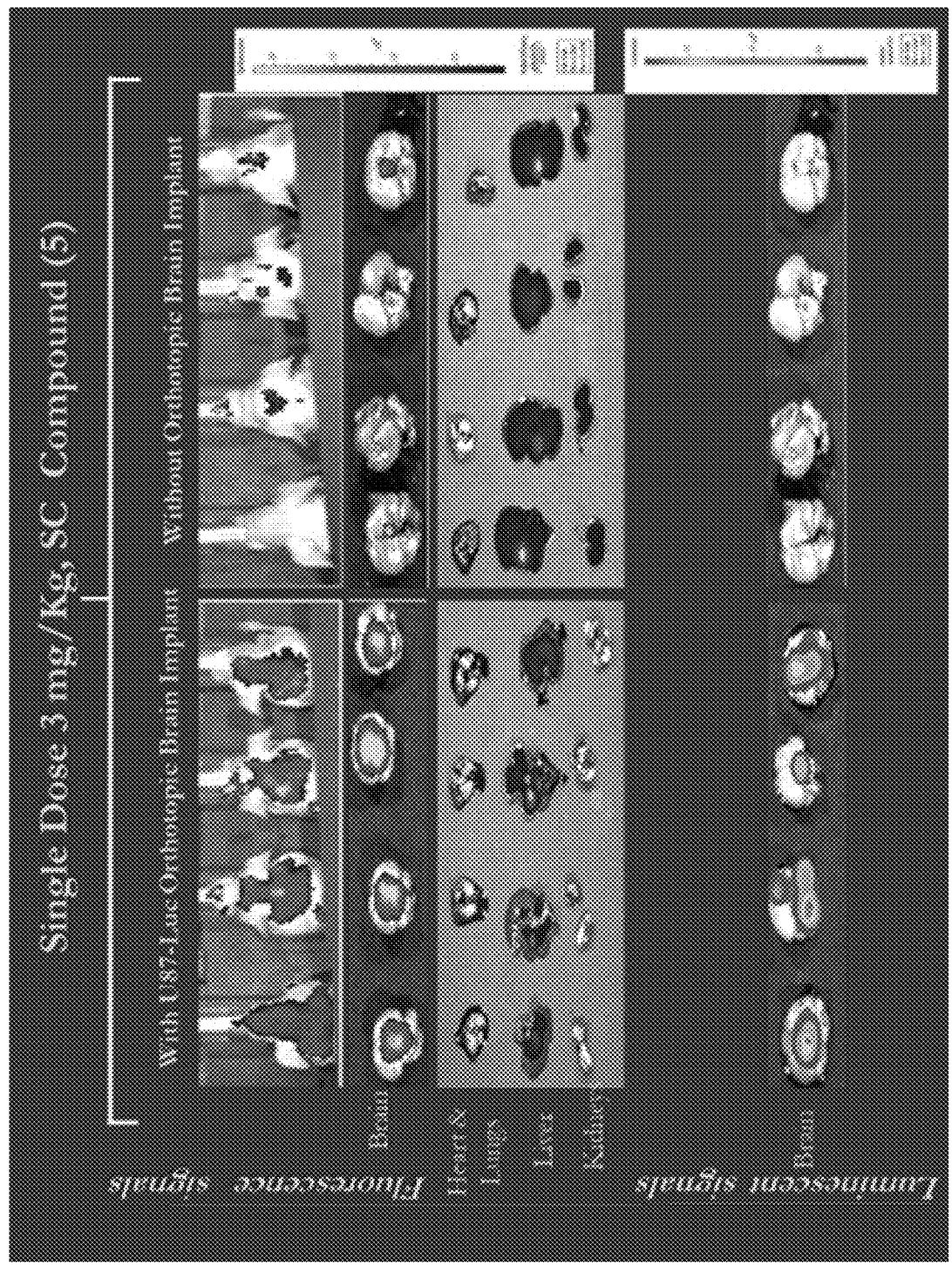
FIG. 29 depicts uptake of exemplary Compound 5 in brain in mice with and without tumor, as well as drug accumulation, or lack thereof, in other organs.

FIG. 29 shows the brain uptake of a single dose (3 mg/Kg, SC) of exemplary Compound 5 (fb-PMT) in mice with and without tumor. As can be seen, animals with implanted tumors demonstrate substantially increased levels of uptake into the brain. Further, FIG. 29 also shows accumulation levels within other organs, including heart and lungs, liver, and kidneys. Drug accumulation is present in the liver in both test groups; however, animals with tumor do not demonstrate accumulation in the kidneys while animals without tumor do demonstrate accumulation in the kidneys. This is further evidence for retention at the tumor site. FIG.

29 also shows luminescent signals of the GBM in the animals with tumor compared to no signal in animals without tumor.

The foregoing FIGS. 21-29 demonstrate the increased blood brain barrier uptake and retention of the exemplary compounds. Thus, the disclosed compounds and compositions comprising these compounds may be delivered across the blood brain barrier and specifically to tumor sites located within the brain. Further, the compounds may be used to target such tumors while minimizing effect on healthy tissue.

The efficacy of these compounds/compositions with respect to GBM tumors will now be described with reference to FIGS. 30-33. The study protocol is as follows: Nude mice having U87-luc xenografts were treated with varying dosages of Compound 2 (fb-PMT) for 3 weeks. Efficacy was determined by tumor weight and luminescent signal intensity compared with a control group. Further, treatment efficacy was also evaluated in comparison with known potential treatment Cilengitide. Efficacy was also determined again after an additional 3 week period with no additional treatment.

Figure 30:
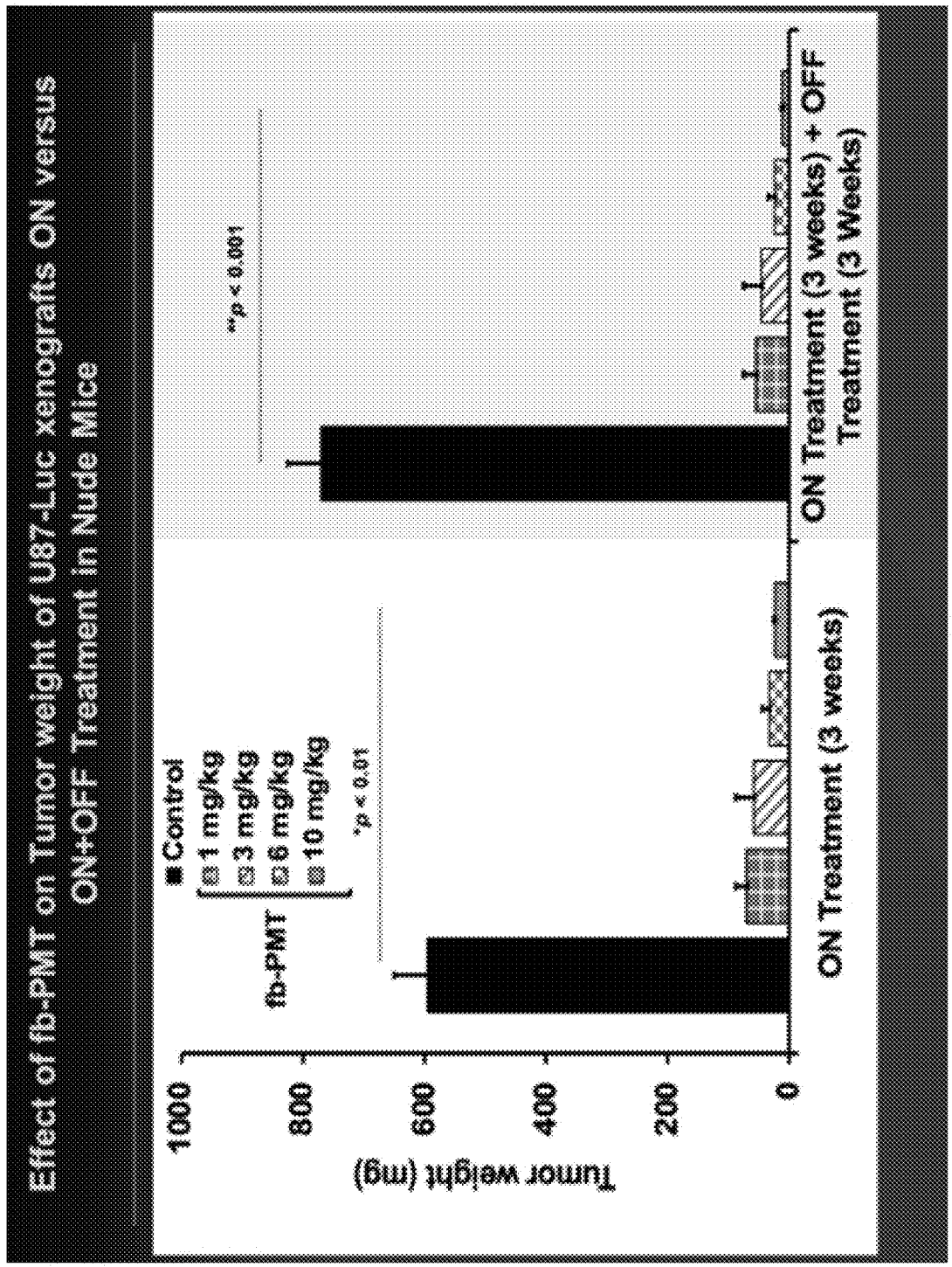
FIG. 30 depicts the effect of varying dosages of exemplary Compound 2 on tumor weight in mice with GBM xenografts.

FIG. 30 shows the effect of exemplary Compound 2 (fb-PMT) on tumor weight after 3 weeks of treatment as well as after 3 weeks of treatment followed by 3 weeks off treatment. Results are shown for doses of 1 mg/kg, 3 mg/kg, 6 mg/kg, and 10 mg/kg versus a control group. Tumor weight for the control group after 3 weeks was approximately 600 mg. All treatment groups showed a dosage dependent reduction of tumor weight to under 100 mg.

Tumor weights were also compared after 6 weeks-3 weeks of treatment followed by a 3 week period with no additional treatment. The control group showed an increased tumor weight of approximately 750 mg. All treatment groups showed a further and additional reduction of tumor weight over the 3 weeks without treatment.

Figure 31:
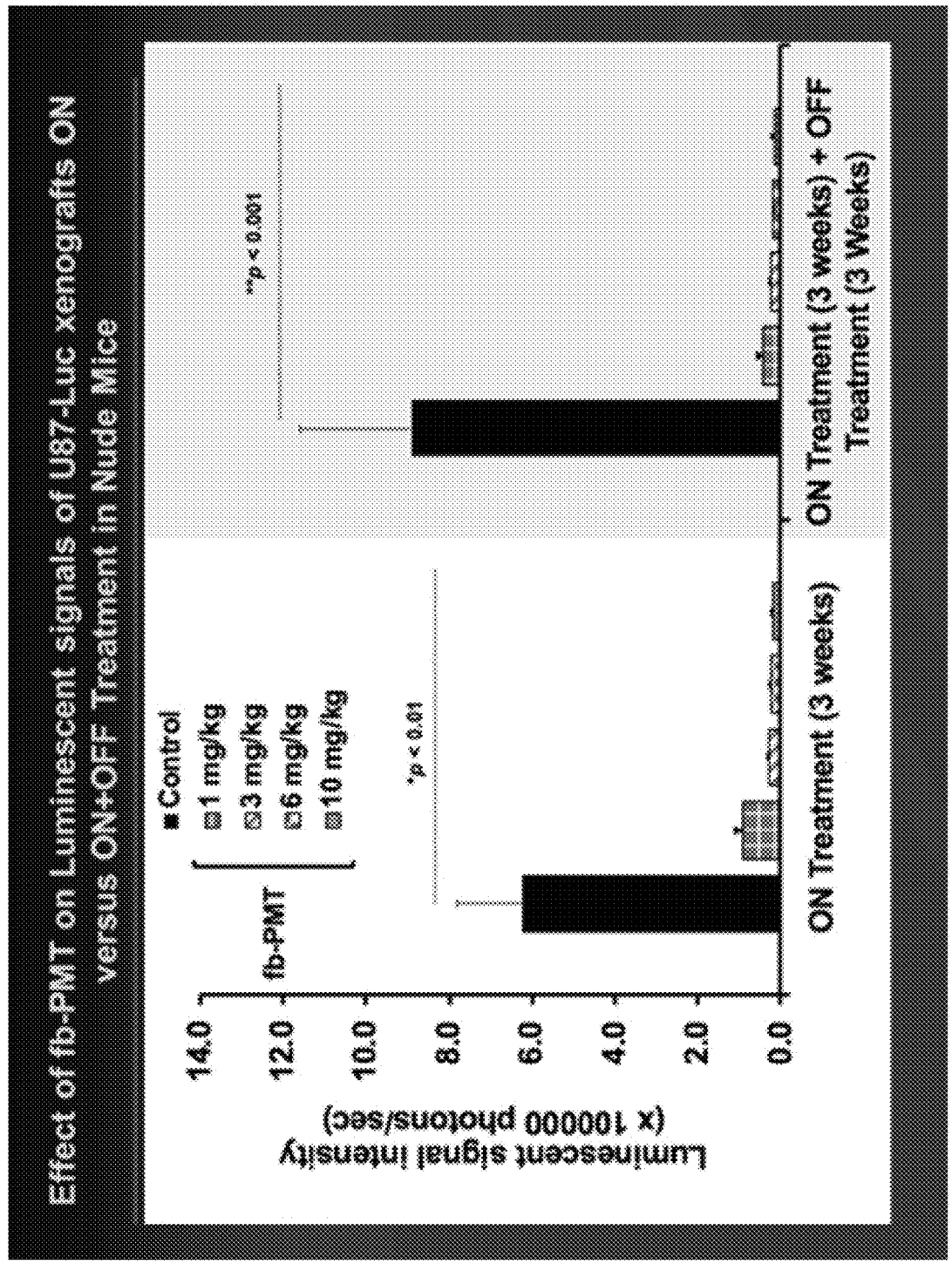
FIG. 31 depicts the effect of varying dosages of exemplary Compound 2 on tumor cell luminescent signal intensity in mice with GBM xenografts.

FIG. 31 shows the effect of Compound 2 (fb-PMT) on luminescent signal intensity after 3 weeks of treatment as well as after 3 weeks of treatment followed by 3 weeks off treatment. Results are shown for doses of 1 mg/kg, 3 mg/kg, 6 mg/kg, and 10 mg/kg versus a control group. Luminescent signal intensity for the control group after 3 weeks was approximately 600,000p/s. All treatment groups showed dosage dependent reduction of luminescent signal intensity to under 100,000p/s.

Signal intensity was also compared after 6 weeks-3 weeks of treatment followed by a 3 week period with no additional treatment. The control group showed an increased signal intensity to over 800,000p/s. All treatment groups showed a further and additional reduction of luminescent signal intensity after the 3 weeks without treatment.

Figure 32:
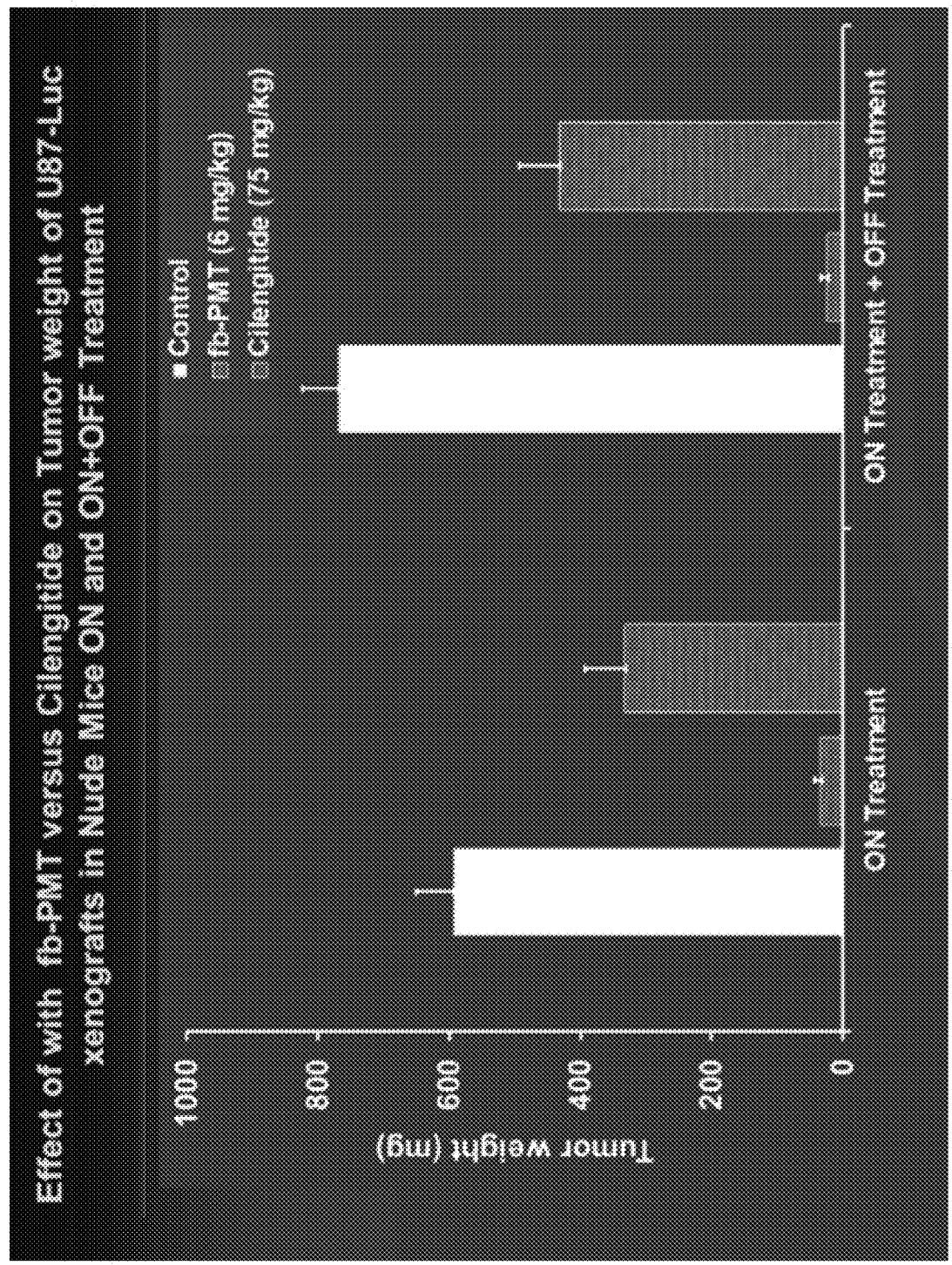
FIG. 32 depicts the effect of a 6 mg/kg dose of exemplary Compound 2 on tumor weight compared with a 75 mg/kg dose of known compound Cilengitide in mice with GBM xenografts.

FIG. 32 shows the effect of Compound 2 (fb-PMT) on tumor weight after 3 weeks of treatment as well as after 3 weeks of treatment followed by 3 weeks off treatment. Results are shown for the 6 mg/kg dose and compared with both a control group and a group treated with Cilengitide at 75 mg/kg. Again, tumor weight for the control group after 3 weeks was approximately 600 mg. Both treatment groups showed reduction of tumor weight after 3 weeks of treatment. However, the group treated with Compound 2 showed substantially increased reduction when compared with the group treated with Cilengitide. For example, as can be seen, the group treated with Cilengitide showed tumor weight reduction to approximately 300 mg, while the group treated with Compound 2 showed reduction to under 50 mg.

Tumor weights were also compared after 6 weeks—3 weeks of treatment followed by a 3 week period with no additional treatment. Again, the control group showed an increased tumor weight of approximately 750 mg after the three weeks without treatment. Further, after three weeks without treatment, the Cilengitide group showed increased tumor weight when compared with the 3 weeks of treatment, with a final tumor weight over 400 mg. Thus, even following 3 weeks of treatment at 75 mg/kg, the tumor was active and growing for the Cilengitide group. Conversely, the Compound 2 group showed further reduction in tumor weight even after 3 weeks without treatment.

Figure 33:
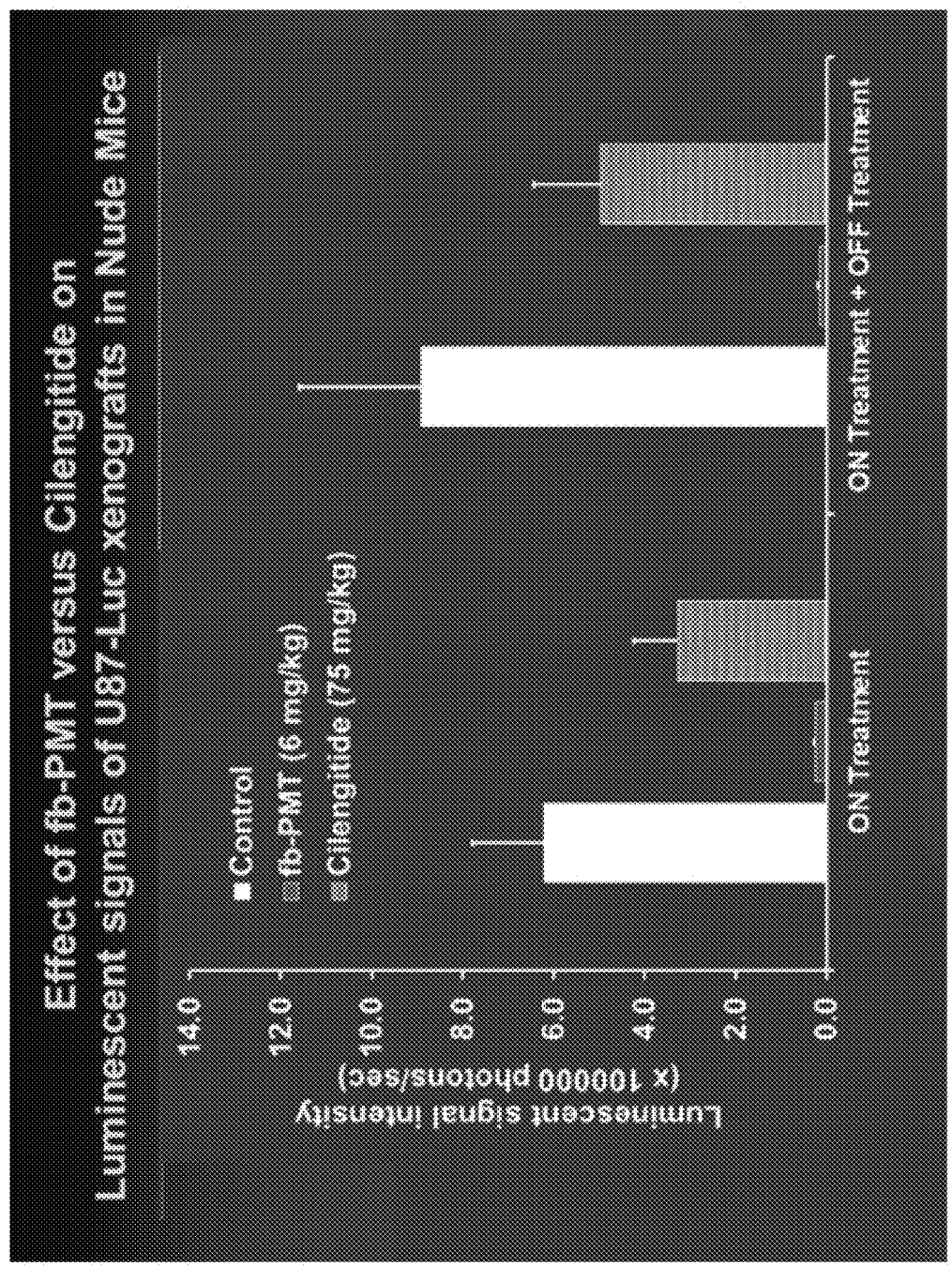
FIG. 33 depicts the effect of a 6 mg/kg dose of exemplary Compound 2 on tumor cell luminescent signal intensity compared with a 75 mg/kg dose of known compound Cilengitide in mice with GBM xenografts.

FIG. 33 shows the effect of Compound 2 on luminescent signal intensity after 3 weeks of treatment as well as after 3 weeks of treatment followed by 3 weeks off treatment. Results are shown for the 6 mg/kg dose of Compound 2 (fb-PMT) and compared with both a control group and a group treated with Cilengitide at 75 mg/kg. Again, luminescent signal intensity for the control group after 3 weeks was approximately 600,000p/s. Both treatment groups showed reduction of signal intensity after 3 weeks of treatment. However, the group treated with Compound 2 showed substantially increased reduction when compared with the group treated with Cilengitide. For example, as can be seen, the group treated with Cilengitide showed signal intensity reduction to approximately 300,000p/s, while the group treated with Compound 2 showed reduction to negligible levels.

Signal intensity was also compared after 6 weeks—3 weeks of treatment followed by a 3 week period with no additional treatment. Again, the control group showed an increased signal intensity to over 800,000p/s. Further, after three weeks without treatment, the Cilengitide group showed increased signal intensity when compared with the 3 weeks of treatment, with a final signal intensity over 500,000p/s. Thus, even following 3 weeks of treatment at 75 mg/kg, the tumor was active and growing for the Cilengitide group. Conversely, the Compound 2 group showed even further reduction in luminescent signal activity even after the additional 3 weeks without treatment.

As demonstrated in this study and shown in these Figures, the described compounds have increased therapeutic effect against glioblastoma (GBM) when compared with both control groups and known treatment compounds/composition that have limited blood brain barrier permeability. As discussed above, the increased therapeutic effect may be attributable to a complex of factors including, active transport across the blood brain barrier due to the thyrointegrin antagonist portion of the compound, retention within the brain and specifically in the location of the tumor due to binding of the thyrointegrin antagonist portion of the compound to integrin $\alpha v\beta 3$ which is present and overexpressed in brain tumors such as GBM, and the effect of the substituent A on the uptake across the blood brain barrier, for example, by an increased accessibility of the transporter target in some embodiments. These features contribute to an increased initial uptake and increased retention within the brain and at the desired treatment location, resulting in increased therapeutic effect.

Still further, the compounds disclosed may have increased scalability, solubility, and yield solid products or intermediates. Synthesis scalability enables efficient and cost-effective manufacturing of the compounds and compositions for patient use. Further, compounds and compositions must be synthesized at sufficient levels of purity in order to be used for treatment. The existence of a compound or composition in the form of a solid product provides improves options for purification. This is contrast to other compounds such as P-Bi-TAT described above, which yields an oil product. The solid exemplary compounds described herein are also readily purified by normal phase chromatography on silica gel, which is not viable for many other PEGylated molecules, including P-Bi-TAT. For example, P-Bi-TAT requires reverse phase chromatography which is not readily scalable. Likewise, aqueous solubility facilitates certain avenues of administration, for example, injection methods such as subcutaneous injection. Thus, these features are often important for realization of production of a compound/composition and also for realization of effective treatment using the compound/composition. The disclosed compounds may be particularly useful as potential treatments options for glioblastoma and other conditions and may be produced in quantities sufficient for treatment dosages.

The compounds may also be prepared as compositions comprising the disclosed compounds. Further, the compounds and/or the compositions may be used to treat conditions such as GBM by administering a therapeutically effective amount of the compound and/or composition to a patient in need thereof, for example, a patient suffering from the condition.

The compositions may also be used for imaging of cancer cell/tumors. For example, the compositions described herein may be used to image tumors within the brain such as glioblastoma. Imaging may be desirable for diagnosis and/or for treatment monitoring. Moreover, the compositions may be used for simultaneous treatment and imaging. For example, the compositions may demonstrate increased retention in the targeted cancer cells/tumors, allowing for enhanced treatment.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of treating cancer, comprising:
   providing a compound having a thyrointegrin antagonist; and
   administering a therapeutically effective amount of the compound to a patient in need thereof, wherein the compound has a general formula:

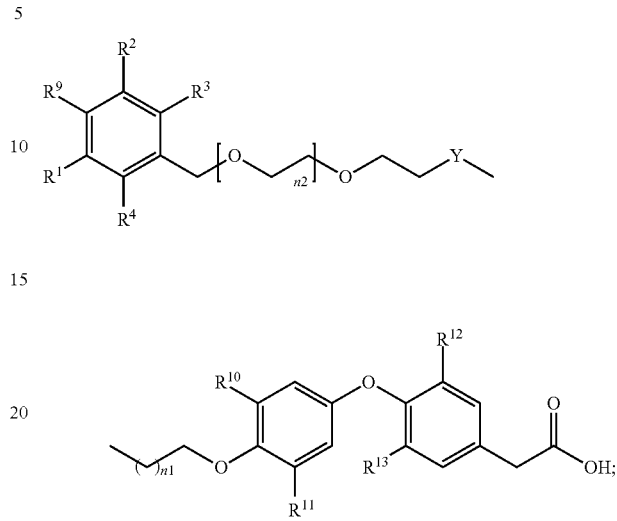

wherein n1≥0;
wherein n2 is 5-200;
wherein R1-R4 and R9 are independently selected from the group consisting of: H, Me, Et, iPr, nPr, nBu, iBu, secBu, tBu, $C_5$-$C_{12}$ n-alkyl, cyclopentyl, cyclohexyl, phenyl, F, Cl, Br, I, CN, $CF_3$, $OCF_3$, $CHF_2$, $OCHF_2$, $SO_2Me$, $NO_2$, —O-Alkyl, —O-Aryl, —$CH_2$—O-Alkyl, —$CH_2$—O-Aryl, Esters, and Amides;
wherein R10-R13 are each independently selected from the group consisting of hydrogen, iodine, and an alkane group; and
wherein Y is selected from the group consisting of:

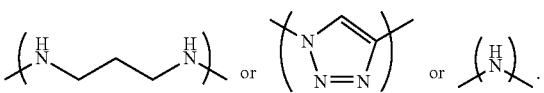

2. The method of claim 1, wherein the cancer is one of gastric cancer, colon cancer, small lung cancer, bladder cancer, breast cancer, ovarian cancer, and skin cancer.

3. The method of claim 1, wherein the compound has a general formula of:

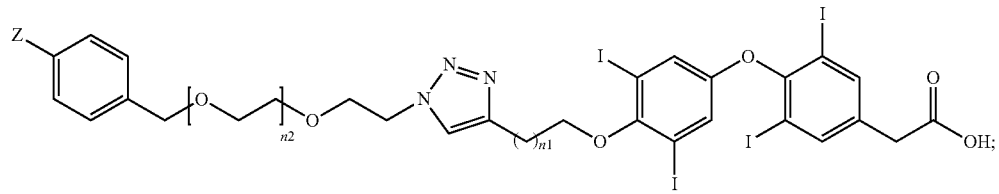

wherein n1≥0;
wherein n2 is 5-200; and
wherein Z is a halogen.

4. The method of claim 1, wherein the compound has a general formula of:

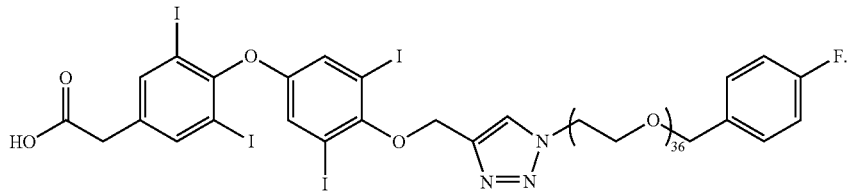

5. A compound having a general formula:

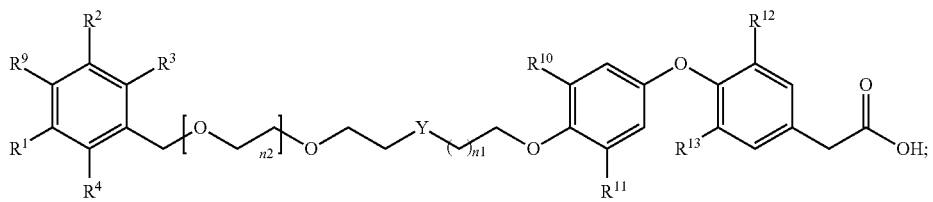

wherein n1≥0;
wherein n2 is 5-200;
wherein R1-R4 and R9 are independently selected from the group consisting of H, Me, Et, iPr, nPr, nBu, iBu, secBu, tBu, $C_5$-$C_{12}$ n-alkyl, cyclopentyl, cyclohexyl, phenyl, F, Cl, Br, I, CN, $CF_3$, $OCF_3$, $CHF_2$, $OCHF_2$, $SO_2Me$, $NO_2$, —O-Alkyl, —O-Aryl, —$CH_2$—O-Alkyl, —$CH_2$—O-Aryl, Esters, and Amides;
wherein R10-R13 are each independently selected from the group consisting of hydrogen, iodine, and an alkane group; and
wherein Y is selected from the group consisting of:

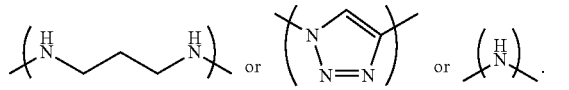

6. A compound consisting of:
a thyrointegrin antagonist selected from the group consisting of: triiodothyroacetic acid and tetraiodothyroacetic acid;
a non-biodegradable polymer;
a linker covalently bound to the thyrointegrin antagonist and the non-biodegradable polymer via a non-cleavable covalent bond; and
a substituent A bound to the non-biodegradable polymer;
wherein the linker is selected from the group consisting of:

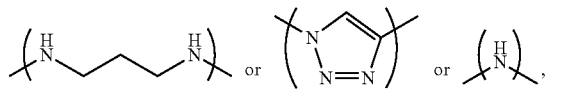

and
wherein the substituent A is selected from:
a) the group consisting of:

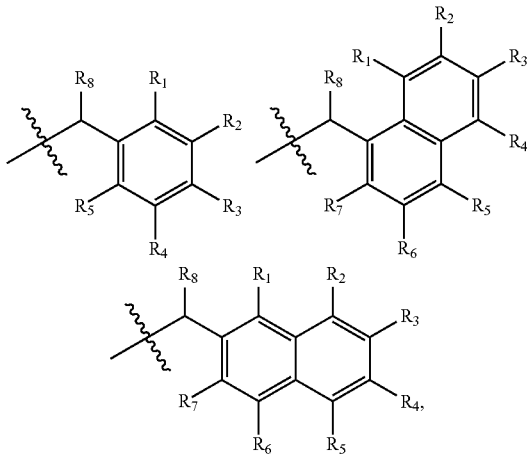

wherein R1-R7 are independently selected from the group consisting of: H, Me, Et, iPr, nPr, nBu, iBu, secBu, tBu, $C_5$-$C_{12}$ n-alkyl, cyclopentyl, cyclohexyl, phenyl, F, Cl, Br, I, CN, $CF_3$, $OCF_3$, $CHF_2$, $OCHF_2$, $SO_2Me$, $NO_2$, —O-Alkyl, —O-Aryl, —$CH_2$—O-Alkyl, —$CH_2$—O-Aryl, Esters, and Amides;
b) the group consisting of:

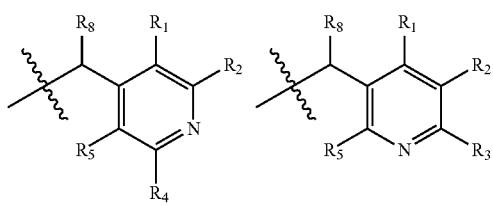

-continued

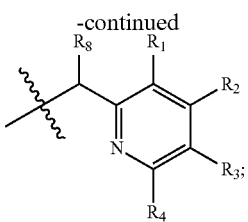

c) the group consisting of:

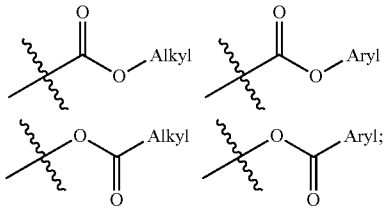

d) the group consisting of:

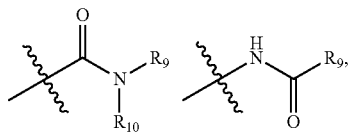

wherein R9 and R9 are independently selected from at least one of H, Alkyl, and Aryl;
e) a 5-membered ring heteroaryl, a fused heteroaryl, a quinoline, and an indole;
f) a phenoxy; and
g) a substituted benzyl.

7. The compound of claim 6, wherein the Alkyl is selected from the group consisting of: Me, Et, iPr, nPr, nBu, iBu, secBu, tBu, $C_5$-$C_{12}$ n-alkyl, cyclopentyl, and cyclohexyl.

8. The compound of claim 6, wherein the Aryl is selected from the group consisting of: phenyl and phenyl substituted with one of alkyl, F, Cl, Br, I, CN, $CF_3$, $OCF_3$, $CHF_2$, $OCHF_2$, $SO_2Me$, and $NO_2$.

9. The compound of claim 6, wherein the Ester is selected from the group consisting of:

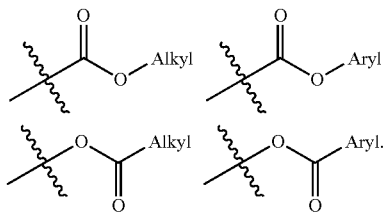

10. The compound of claim 6, wherein the Amide is selected from the group consisting of:

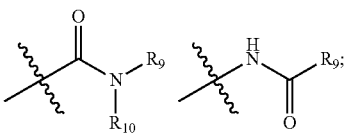

wherein R9 and R9 are independently selected from at least one of H, Alkyl, and Aryl.

11. The compound of claim 6, wherein the polymer is polyethylene glycol (PEG).

12. The compound of claim 6, wherein the substituted benzyl comprises a halogen.

* * * * *